(12) United States Patent
Schunk et al.

(10) Patent No.: US 10,100,041 B2
(45) Date of Patent: *Oct. 16, 2018

(54) PYRAZOLYL SUBSTITUTED TETRAHYDROPYRANYLSULFONES

(71) Applicant: GRÜNENTHAL GMBH, Aachen (DE)

(72) Inventors: Stefan Schunk, Aachen (DE); Melanie Reich, Aachen (DE); René Michael Koenigs, Erkelenz (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/288,009

(22) Filed: Oct. 7, 2016

(65) Prior Publication Data

US 2017/0101398 A1 Apr. 13, 2017

(30) Foreign Application Priority Data

Oct. 8, 2015 (EP) .................................... 15002880

(51) Int. Cl.
*C07D 405/04* (2006.01)
*C07D 405/14* (2006.01)
*C07D 409/14* (2006.01)

(52) U.S. Cl.
CPC ......... *C07D 405/04* (2013.01); *C07D 405/14* (2013.01); *C07D 409/14* (2013.01)

(58) Field of Classification Search
None
See application file for complete search history.

(56) References Cited

U.S. PATENT DOCUMENTS

2015/0291572 A1  10/2015  Schunk et al.
2015/0291573 A1* 10/2015  Schunk ................ C07D 413/04
                                                       514/336
2017/0101397 A1   4/2017  Schunk et al.

FOREIGN PATENT DOCUMENTS

WO  2007 125398 A2  11/2007
WO  2010 007072 A1   1/2010
WO  2011 035159 A1   3/2011

OTHER PUBLICATIONS

Barbasiewicz, et al., "New reactions of γ-halocarbanions: underestimated reactive intermediates in organic synthesis"; Russian Chemical Bulletin, International Edition, vol. 53, No. 9, pp. 1846-1858, Sep. 2004.

Bennett et al., "A Peripheral Mononeuropathy in rat that produces disorders of pain sensation like those seen in man": Pain, Elsevier Sciences Publishers B.V., No. 33, pp. 87-107, 1998.
Brandt, et al., "Synthesis of substituted tetrahydrofurans via intermolecular reactions of γ-chlorocarbanions of 3-substituted 3-chloropropylphenyl sulfones with aldehydes", Tetrahedron 66, pp. 3378-3385, 2010.
Craig et al., "Stereoselective Synthesis of 3-(Phenylsulphonyl)-2,5 Disubstituted Tetrahydrofurans via 5-Endo-trig Ring-Closure Reactions"; Tetrahedron Letters, vol. 33, No. 5, pp. 695-698, 1992.
Craig et al., "Stereoselective Synthesis of 2,5-Dialky-3-(phenylsulfonyl) Tetrahydrofurans via Cyclisation of Z-Sulfonyl-substituted Homoallylic Alcohols", Tetrahedron Letters, vol. 36, No. 4, pp. 7531-7534, 1995.
Craig, et al., "Stereoselective Synthesis of Substituted Tetrahydrofurans Using 5-Endo-trig Cyclisation Reactions"; Tetrahedron 55, pp. 13471-13494, 1999.
D'Amour et al., "A Method for Determining Loss of Pain Sensation", The Biologic Research Laboratory, University of Denver, pp. 74-79, Jan. 27, 1941.
Dubuisson et al., "The Formalin Test: A Quantitative Study of the Analgesic Effects of Morphine, Meperidine, and Brain Stem Stimulation in Rats and Cat"; Elsevier/North-Holland Biomedical Press, Pain, No. 4 pp. 161-174, 1977.
Kim et al., "An Experimental Model for Peripheral Neuropathy Produced by Segmental Spinal Nerve Ligation in the Rat", Pain, Elsevier Sciences Publishers B.V., No. 50, pp. 355-363, 1992.
Makosza et al., "New Reactions of γ-Halocarbanions: Simple Synthesis of Substituted Tetrahydrofurans"; Chem. Eur. J., vol. 8, No. 18, pp. 4234-4240, 2002.
Makosza et al., "Diastereoselective Synthesis of Tetrahydrofurans via Reaction of γ,σ-Eposycarbanions with Aldehydes", Organic Letters, vol. 7, No. 14, pp. 2945-2948, 2005.
Makosza et al. (2009): STN International HCAPLUS database, Columbus (OH) Accession No. 2009:371746.
Makoszaet al., "γ-Diphenylphosphinoxy Carbanions: Slow Reacting Analogues of γ-Halocarbanions", Phosphorus, Sulfur, and Silicon, No. 184, pp. 857-864, 2009.
G.P. Miljanich,"Ziconotide: Neuronal Calcium Channel Blocker for Treating Severe Chronic Pain", Current Medicinal Chemistry, No. 11, pp. 3029-3040, 2004.
Rauck et al., "Intrathecal Ziconotide for Neuropathic Pain: A Review", Pain Practice, vol. 9, Issue 5, pp. 327-337, 2009.
Staats et al., "Intrathecal Ziconotide in the Treatment of Refractory Pain in Patients With Cancer or AIDS A Randomized Controlled Trial", American Medical Association, vol. 291, No. 1, pp. 63-70, 2004.
Yamamoto, et al; "Recent Updates of N-Type Calcium Channel Blockers with Therapeutic Potential for Neuropathic Pain . . . " Current Topics in Medicinal Chemistry, 2009, 9, 377-395.

* cited by examiner

*Primary Examiner* — Kamal A Saeed
(74) *Attorney, Agent, or Firm* — Norris McLaughlin & Marcus, P.A.

(57) ABSTRACT

The invention relates to pyrazolyl substituted tetrahydropyranylsulfones as voltage gated calcium channel blockers, to pharmaceutical compositions containing these compounds and also to these compounds for use in the treatment and/or prophylaxis of pain and further diseases and/or disorders.

15 Claims, No Drawings

PYRAZOLYL SUBSTITUTED TETRAHYDROPYRANYLSULFONES

PRIORITY CLAIM

This application claims priority of European Patent Application No. 15002880.1, filed Oct. 8, 2015, the disclosure of which patent application is incorporated herein by reference.

FIELD OF THE INVENTION

The invention relates to pyrazolyl-substituted tetrahydropyranylsulfones as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

SUMMARY OF THE INVENTION

The present invention describes small molecule CaV2.2 channel blockers. Sulfonamide based CaV2.2 channel modulatros are known from WO 2007/125398.

It was therefore an object of the invention to provide novel compounds, preferably having advantages over the prior-art compounds. The compounds should be suitable in particular as pharmacological active ingredients in pharmaceutical compositions, preferably in pharmaceutical compositions for use in the treatment and/or prophylaxis of disorders or diseases which are at least partially mediated by CaV2.2 calcium channels.

This object is achieved by the subject matter described herein.

The present invention therefore relates to a compound of general formula (I),

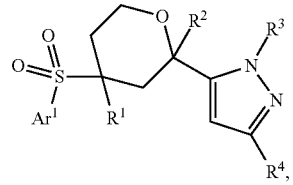

wherein
$R^1$ is selected from the group consisting of H or $C_{1-6}$-alkyl;
$R^2$ is selected from the group consisting of H or $C_{1-6}$-alkyl;
$R^3$ represents $L'-R^{3a}$,
  wherein L' is bond or $CH_2$ and
  $R^{3a}$ is selected from the group consisting of substituted $C_{1-6}$-alkyl, $C_{3-6}$-cycloalkyl or 3 to 7 membered heterocyclyl,
  wherein said substituted $C_{1-6}$-alkyl is substituted by one or two substituents independently selected from the group consisting of OH, $OCH_3$, $S(=O)_2CH_3$, $N(CH_3)_2$, $C(=O)NH_2$, $C(=O)NH(CH_3)$ and $C(=O)N(CH_3)_2$;
  wherein said $C_{3-6}$-cycloalkyl and said 3 to 7 membered heterocyclyl is unsubstituted or substituted by one or two substituents independently selected from the group consisting of OH, =O, $OCH_3$, $S(=O)_2CH_3$, $NH_2$, $NH(CH_3)$, $N(CH_3)_2$, $C(=O)OH$, $C(=O)NH_2$, $C(=O)NH(CH_3)$ and $C(=O)N(CH_3)_2$;
  and wherein said 3 to 7 membered heterocyclyl contains one or two heteroatoms or heteroatom groups selected from O, NH, $N(CH_3)$, $S(=O)$ and $S(=O)_2$;
$R^4$ represents $L-R^5$,
  wherein L is bond, $CH_2$, $C(CH_3)_2$, O or $S(=O)_2$ and
  $R^5$ is selected from the group consisting of $C_{1-6}$-alkyl, $C_{3-6}$-cycloalkyl or 3 to 7 membered heterocyclyl,
  wherein said 3 to 7 membered heterocyclyl is characterized that it contains one heteroatom or heteroatom group, selected from O, NH, $N(CH_3)$, $S(=O)$ and $S(=O)_2$;
  wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
  and
  wherein said $C_{3-6}$-cycloalkyl or said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
$Ar^1$ represents aryl or heteroaryl, wherein said aryl or said heteroaryl is substituted by zero or one or two or three substituents $R^7$, wherein each $R^7$ is independently selected from the group consisting of F; Cl; Br; I; $NO_2$; CN; $C_{1-6}$-alkyl; $CF_3$; $CF_2H$; $CFH_2$; $CF_2Cl$; $CFCl_2$; C(O)—H; C(O)—$C_{1-6}$-alkyl; C(O)—OH; C(O)—O—$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—S(O)$_2$—$C_{1-6}$-alkyl; O—S(O)$_2$—OH; O—S(O)$_2$—O—$C_{1-6}$-alkyl; O—S(O)$_2$—$NH_2$; O—S(O)$_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N($R^{13}$)—C(O)—$C_{1-6}$-alkyl; N($R^{13}$)—C(O)—O—$C_{1-6}$-alkyl; N($R^{13}$)—C(O)—$NH_2$; N($R^{13}$)—C(O)—N(H)($C_{1-6}$-alkyl); N($R^{13}$)—C(O)—N($C_{1-6}$-alkyl)$_2$; N($R^{13}$)—S(O)$_2$OH; N($R^{13}$)—S(O)$_2$—$C_{1-6}$-alkyl; N($R^{13}$)—S(O)$_2$—O—$C_{1-6}$-alkyl; N($R^{13}$)—S(O)$_2$—$NH_2$; N($R^{13}$)—S(O)$_2$—N(H)($C_{1-6}$-alkyl); N($R^{13}$)—S(O)$_2$N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 7 membered heterocyclyl; aryl; heteroaryl; O—$C_{3-6}$-cycloalkyl; O-(3 to 7 membered heterocyclyl); O-aryl; O-heteroaryl; N($R^{13}$)—$C_{3-6}$-cycloalkyl; N($R^{13}$)-(3 to 7 membered heterocyclyl); N($R^{13}$)-aryl; N($R^{13}$)-heteroaryl; C(O)—$C_{3-6}$-cycloalkyl; C(O)-(3 to 7 membered heterocyclyl); C(O)-aryl; C(O)-heteroaryl; S(O)$_2$—$C_{3-6}$-cycloalkyl; S(O)$_2$-(3 to 7 membered heterocyclyl); S(O)$_2$-aryl; S(O)$_2$-heteroaryl; S(O)N($R^{13}$)—$C_{3-6}$-cycloalkyl; S(O)N($R^{13}$)-(3 to 7 membered heterocyclyl); S(O)N($R^{13}$)-aryl and S(O)N($R^{13}$)-heteroaryl, wherein $R^{13}$ represents H or $C_{1-6}$-alkyl;

with the proviso that the compound of general formula (I) is not 1-(2-Methoxyethyl)-5-(4-methyl-4-((3-(trifluoromethyl)phenyl)sulfonyl)tetrahydro-2H-pyran-2-yl)-3-(trifluoromethyl)-1H-pyrazole [$R^1$=$CH_3$, $R^2$=H, $R^3$=$CH_2CH_2OCH_3$, $R^4$=$CF_3$, $Ar^1$=3-trifluoromethyl-phenyl]; optionally in the form of an individual stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The compounds according to general formula (I) possess at least 2 stereogenic carbon atoms: the carbon atom bearing $R^1$ and the carbon atom bearing $R^2$.

The compounds according to formula (I) may be stereochemically differentiated according to their relative structural orientation. The compounds wherein the residues $R^1$ and $R^2$ have the same relative orientation, for instance both up ("bold wedge") or both down ("broken wedge") are referred within the scope of the present invention as the "cis" diastereomer (scheme 1). The compounds wherein the residues $R^1$ and $R^2$ have a differented relative orientation, for instance $R^1$ up ("bold wedge") and $R^2$ down ("broken wedge") or vice versa are referred within the scope of the present invention as the "trans" diastereomer (scheme 2).

Diastereoisomers differ with respect to their physical and chemical properties. Methods to determine the diastereomeric ratio (dr) are well known to the person skilled in the art and include, but are not limited to, NMR-methods.

A diastereomerically pure compound or a diastereomer according to the present invention refers to a stereoisomer, having a diastereomeric ratio of >90:10, particularily >92:8, preferably >95:5, more preferably >98:2 and even more preferably >99:1.

For both diastereomers, two enantiomers are possible. An enantiomerically pure compound or an enantionmer according to the present invention refers to a stereoisomer, having an enatiomeric excess of >90% ee, particularily >92% ee, preferably >95% ee, more preferably >98% ee and even more prepferably >98% ee. A racemic mixture or a racemate refers to an equal mixture of two corresponding enantiomers.

Methods to determine the enatiomeric excess are well known to the person skilled in the art and include, but are not limited to, optical rotary dispersion, circular dichroism, NMR-methods using chiral auxiliaries ("shift reagents") or separation via chiral HPLC (high performance liquid chromatography, using a chiral stationary phase), chiral GLC (gas-liquid chromatography, using a chiral stationary phase phase) or chiral SFC (supercritical fluid chromatography using a chiral stationary phase).

Determination of the absolute stereochemical structure is well known to the person skilled in the art and includes, but are not limited to, x-ray diffractometry.

The stereogenic information of the compounds of the present invention is described according to their relative chemical structure as as detailed below:

1) A cis racemic compound (cis-rac) refers to a racemic mixture of two enantiomers as depicted in scheme 1.

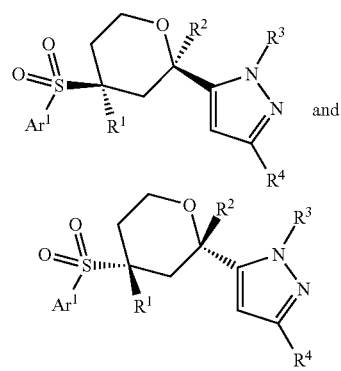

(Scheme 1).

and

2) A trans racemic compound (trans-rac) refers to a racemic mixture of two enantiomers as depicted in scheme 2.

(Scheme 2).

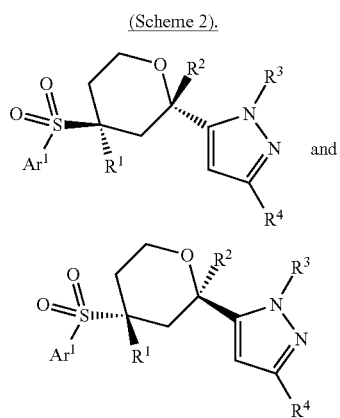

and

3) A cis enantiomer 1 compound (cis-EN1) refers to one single enantiomer as depicted in scheme 3.

(Scheme 3).

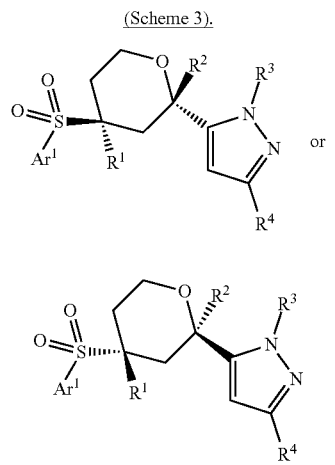

or

4) A cis enantiomer 2 compound (cis-EN2) refers to the other single enantiomer, which is not cis-EN1 as depicted in scheme 3.

(Scheme 3).

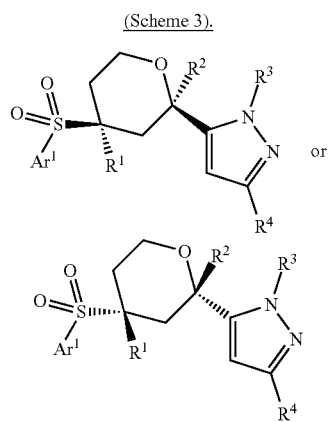

or

5) A trans enantiomer 1 compound (trans-EN1) refers to one single enantiomer as depicted in scheme 4.

(Scheme 4).

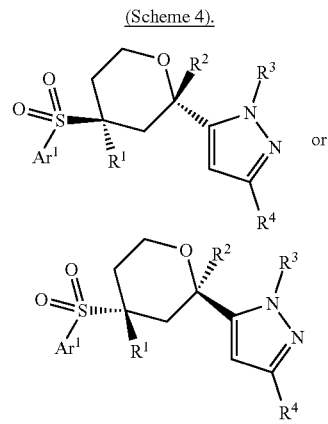

or

6) A trans enantiomer 2 compound (trans-EN2) refers to the other single enantiomer, which is not trans-EN1 as depicted in scheme 4.

(Scheme 4).

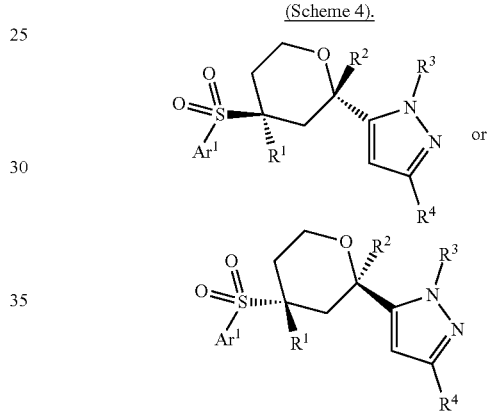

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The invention also includes all suitable isotopic variations of a compound of the invention, wherein at least one random or specific atom of the compound is partly or fully replaced by one or more certain isotopes of the respective element, being different from the naturally occurring isotopic distribution for this element. Preferred isotopes are $^2$H (deuterium), $^3$H (tritium), $^{13}$C and $^{14}$C. Isotopic variations of a compound of the invention can be prepared by conventional procedures known by a person skilled in the art.

The term "$C_{1-6}$-alkyl" comprise in the sense of this invention acyclic saturated aliphatic hydrocarbon residues, which can be respectively branched or unbranched and which contain 1 to 6 carbon atoms, i.e. 1, 2, 3, 4, 5 or 6 carbon atoms. Preferred $C_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl, and n-hexyl.

In relation to the term "$C_{1-6}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of $CH(OH)CHF_2$. The multiple substitution can be carried out using the same or using different substituents.

The term "$C_{3-6}$-cycloalkyl" mean for the purposes of this invention cyclic aliphatic hydrocarbons containing 3, 4, 5 or 6 carbon atoms, respectively, wherein the hydrocarbons in each case can be saturated or unsaturated (but not aromatic). The cycloalkyl group can be bound to the respective superordinate general structure via any desired and possible ring member of the cycloalkyl group. The $C_{3-6}$-cycloalkyl can also be condensed with further saturated, (partially) unsaturated, (hetero)cyclic, aromatic or heteroaromatic ring systems, i.e. with cycloalkyl, heterocyclyl, aryl or heteroaryl residues. $C_{3-6}$-cycloalkyls can furthermore be singly or multiply bridged such as, for example, in the case of adamantyl, bicyclo[2.2.1]heptyl or bicyclo[2.2.2]octyl. Preferred $C_{3-6}$-cycloalkyl groups are selected from the group consisting of cyclopropyl, cyclobutyl, cyclopentyl, cyclohexyl, adamantly, cyclopentenyl, cyclohexenyl, cycloheptenyl, cyclooctenyl,

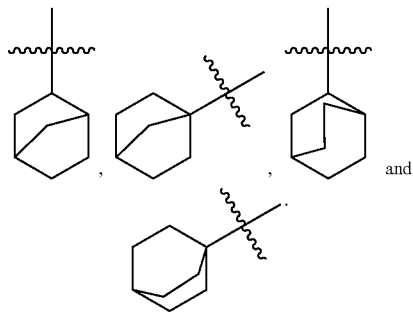

Particularly preferred $C_{3-6}$-cycloalkyl groups are $C_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic saturated or unsaturated (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S($=$O), S($=$O)$_2$, N, NH and N($C_{1-6}$-alkyl) such as N($CH_3$). The cycloalkyl groups can also be condensed with further saturated or partially) unsaturated cycloalkyl or heterocyclyl, aromatic or heteroaromatic ring systems. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further sat. or (partially) unsat. cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further sat. or (partially) unsat. cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

Within the scope of the present invention, the symbols

used in the formulae denotes a link of a corresponding residue to the respective superordinate general structure.

In one embodiment of the first aspect of the invention, the compound according to general formula (I) is characterized in that $R^2$ represents H, $CH_3$, $C_2H_5$, $CH_2CH_2CH_3$ or $CH(CH_3)_2$. Preferably, $R^2$ represents H.

In another embodiment of the first aspect of the invention, the compound according to general formula (I) is characterized in that $R^1$ represents H, $CH_3$, $C_2H_5$, $CH_2CH_2CH_3$ or $CH(CH_3)_2$. Preferably, $R^1$ represents $CH_3$.

In another preferred embodiment of the first aspect of the invention, the compound according to general formula (I) is characterized in that R$^1$ represents CH$_3$ and R$^2$ represents H, so the compound is represented by general formula (II),

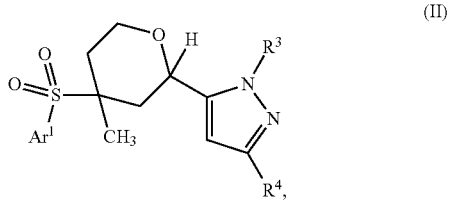

(II)

wherein Ar$^1$, R$^3$ and R$^4$ are defined as herein.

In another embodiment of the first aspect of the invention, the compound according to the invention is one diastereomer. Preferably, the compound according to the invention is the cis-diastereomer. Still preferably, the compound according to the invention is the trans-diastereomer.

Thus, one preferred embodiment of the first aspect of the invention is characterized in that the compound of general formula (I) or (II) is one diastereomer.

The cis-diastereomer or the trans-diastereomer may be in the form of a single enantiomer or in the form of an enantiomeric mixture, preferably of a racemate.

In yet another embodiment of the first aspect of the invention, the compound according to the invention is in only one enantiomeric form. Preferably, the compound according to the invention is the racemate of the cis-diastereomer (cis-rac) or a single enantiomer of the cis-diastereomer (cis-EN1 or cis-EN2). Still preferably, the compound according to the invention is the racemate of the trans-diastereomer (trans-rac) or a single enantiomer of the trans-diastereomer (trans-EN1 or trans-EN2).

Thus, one preferred embodiment of the first aspect of the invention is characterized in that the compound of general formula (I) or (II) is one enantiomer.

In one preferred embodiment of the first aspect of the invention is characterized in that the compound of general formula (I) or (II) is the enantiomer, which exhibits at room temperature and a wavelength of 589 nm (Na-D-line) a positive optical rotation in dichloromethane or methanol.

In another preferred embodiment of the first aspect of the invention is characterized in that the compound of general formula (I) or (II) is the enantiomer, which exhibits at room temperature and a wavelength of 589 nm (Na-D-line) a negative optical rotation in dichloromethane or methanol.

In another embodiment of the first aspect of the invention, the compound according to general formula (I) is characterized in that Ar$^1$ represents phenyl or pyridinyl, substituted by zero or one or two or three substituents R$^7$.

In preferred embodiment of the first aspect of the invention, the compound according to general formula (I) is characterized in that Ar$^1$ represents phenyl or pyridinyl, substituted by zero, one or two substituents R$^7$, wherein each R$^7$ is independently selected from the group consisting of F; Cl; CN; C$_{1-6}$-alkyl; CF$_3$; CF$_2$H; CFH$_2$; C(O)—C$_{1-6}$-alkyl; C(O)OH; C(O)—O—C$_{1-6}$-alkyl; C(O)—N(H)(OH); C(O)—NH$_2$; C(O)—N(H)C$_{1-6}$-alkyl); C(O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(C$_{1-6}$-alkyl)-C(O)—C$_{1-6}$-alkyl; N(H)—S(O)$_2$—C$_{1-6}$-alkyl; SCF$_3$; S—C$_{1-6}$-alkyl; S(O)—C$_{1-6}$-alkyl; S(O)$_2$—C$_{1-6}$-alkyl; S(O)$_2$—NH$_2$; S(O)$_2$—N(H)(C$_{1-6}$-alkyl); S(O)$_2$—N(C$_{1-6}$-alkyl)$_2$; C$_{3-6}$-cycloalkyl; 3 to 7 membered heterocyclyl; O—C$_{3-6}$-cycloalkyl and O-(3 to 7 membered heterocyclyl).

Preferably, R$^7$ is independently selected from the group consisting of F; Cl; CN; C$_{1-6}$-alkyl; CF$_3$; CF$_2$H; CFH$_2$; C(=O)—C$_{1-6}$-alkyl; C(=O)—OH; C(=O)—O—C$_{1-6}$-alkyl; C(=O)—N(H)(OH); C(=O)—NH$_2$; C(=O)—N(F)(C$_{1-6}$-alkyl); C(=O)—N(C$_{1-6}$-alkyl)$_2$; OH; OCF$_3$; OCF$_2$H; OCFH$_2$; OCF$_2$Cl; OCFCl$_2$; O—C$_{1-6}$-alkyl; NH$_2$; N(H)(C$_{1-6}$-alkyl); N(C$_{1-6}$-alkyl)$_2$; N(H)—C(=O)—C$_{1-6}$-alkyl; N(C$_{1-6}$-alkyl)-C(=O)—C$_{1-6}$-alkyl; N(H)—S(=O)$_2$—C$_{1-6}$-alkyl; SCF$_3$; S—C$_{1-6}$-alkyl; S(=O)—C$_{1-6}$-alkyl; S(=O)$_2$—C$_{1-6}$-alkyl; S(=O)$_2$—NH$_2$; S(=O)$_2$—N(H)(C$_{1-6}$-alkyl); S(=O)$_2$—N(C$_{1-6}$-alkyl)$_2$; C$_{3-6}$-cycloalkyl; 3 to 7 membered heterocyclyl; O—C$_{3-6}$-cycloalkyl and O-(3 to 7 membered heterocyclyl).

In yet another embodiment of the first aspect of the invention, the compound according to general formula (I) or (II) is characterized in that Ar$^1$ is selected from the group consisting of 3-trifluoromethyl-phenyl; 3-difluoromethyl-phenyl; 3-fluoromethyl-phenyl; 3-trifluoromethoxy-phenyl; 3-difluoromethoxy-phenyl; 3-fluoromethoxy-phenyl; 3-fluoro-phenyl; 3-cyanophenyl; 6-trifluoromethyl-pyridin-2-yl; 3-difluoromethyl-pyridin-2-yl; 3-fluoromethyl-pyridin-2-yl; 3-trifluoromethoxy-pyridin-2-yl; 3-difluoromethoxy-pyridin-2-yl; 3-fluoromethoxy-pyridin-2-yl; 3-fluoro-pyridin-2-yl or 3-cyano-pyridin-2-yl. Particularly preferred compounds according to the present invention are characterized in that Ar$^1$ represents of 3-trifluoromethyl-phenyl.

In yet another embodiment of the first aspect of the invention, the compound according to general formula (I) or (II) is characterized in that
R$^3$ represents L'-R$^{3a}$,
wherein L' is bond or CH$_2$ and
R$^{3a}$ is selected from the group consisting of substituted C$_{1-6}$-alkyl, C$_{3-6}$-cycloalkyl or 3 to 7 membered heterocyclyl,
wherein said substituted C$_{1-6}$-alkyl is substituted by one or two substituents independently selected from the group consisting of F, Cl, OH, OCH$_3$, OCFH$_2$, OCHF$_2$, OCF$_3$, S(=O)$_2$CH$_3$, S(=O)$_2$CHF$_2$, S(=O)$_2$CF$_3$, N(CH$_3$)$_2$, C(=O)NH$_2$ C(=O)NH(CH$_3$) and C(=O)N(CH$_3$)$_2$;
wherein said C$_{3-6}$-cycloalkyl and said 3 to 7 membered heterocyclyl is unsubstituted or substituted by one or two substituents independently selected from the group consisting of F, Cl, CH$_3$, CFH$_2$, CHF$_2$, CF$_3$, OH, OCH$_3$, CH$_2$OH, CH$_2$OCH$_3$, OCFH$_2$, OCHF$_2$, OCF$_3$, S(=O)$_2$CH$_3$, S(=O)$_2$CHF$_2$, S(=O)$_2$CF$_3$, NH$_2$, NH(CH$_3$), N(CH$_3$)$_2$, C(=O)OH, C(=O)NH$_2$, C(=O)NH(CH$_3$) and C(=O)N(CH$_3$)$_2$;
and wherein said 3 to 7 membered heterocyclyl contains one heteroatom or heteroatom group, selected from O, NH, N(CH$_3$), S(=O) and S(=O)$_2$.

In another embodiment of the first aspect of the invention, the compound according to general formula (I) or (II) is characterized in that L' is bond or CH$_2$. Preferably, L' is bond. Preferably, L' is CH$_2$.

In yet another embodiment of the first aspect of the invention, the compound according to general formula (I) or (II) is characterized in that
L' is bond and
R$^{3a}$ is substituted C$_{1-6}$-alkyl,
wherein said C$_{1-6}$-alkyl is substituted by one substituent selected from the group consisting of OH, OCH$_3$, C(=O)OH, C(=O)NH$_2$, C(=O)NH(CH$_3$), C(=O)N(CH$_3$)$_2$, NH$_2$, N(CH$_3$)$_2$ and S(=O)$_2$CH$_3$.

In yet another embodiment of the first aspect of the invention, the compound according to general formula (I) or (II) is characterized in that $R^{3a}$ is $C_{3-6}$-cycloalkyl, wherein said $C_{3-6}$-cycloalkyl is unsubstituted or substituted by one or two or three or four substituents independently selected from the group consisting of F, Cl, $CH_3$, $CFH_2$, $CHF_2$, $CF_3$, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $NH_2$, $NH(CH_3)$, $N(CH_3)_2$, $C(=O)NH_2$, $C(=O)NH(CH_3)$ and $C(=O)N(CH_3)_2$.

Preferably, $R^{3a}$ is $C_{3-6}$-cycloalkyl, wherein said $C_{3-6}$-cycloalkyl is cyclopropyl or cyclobutyl, wherein said cyclopropyl or said cyclobutyl is unsubstituted or substituted by one or two or three or four substituents independently selected from the group consisting of F, Cl, $CH_3$, $CFH_2$, $CHF_2$, $CF_3$, OH, $OCH_3$, $OCFH_2$, $OCHF_2$, $OCF_3$, $S(=O)_2CH_3$, $S(=O)_2CHF_2$, $S(=O)_2CF_3$, $NH_2$, $NH(CH_3)$, $N(CH_3)_2$, $C(=O)NH_2$, $C(=O)NH(CH_3)$ and $C(=O)N(CH_3)_2$.

More preferably, wherein L' is $CH_2$ and $R^{3a}$ is selected from the group consisting of

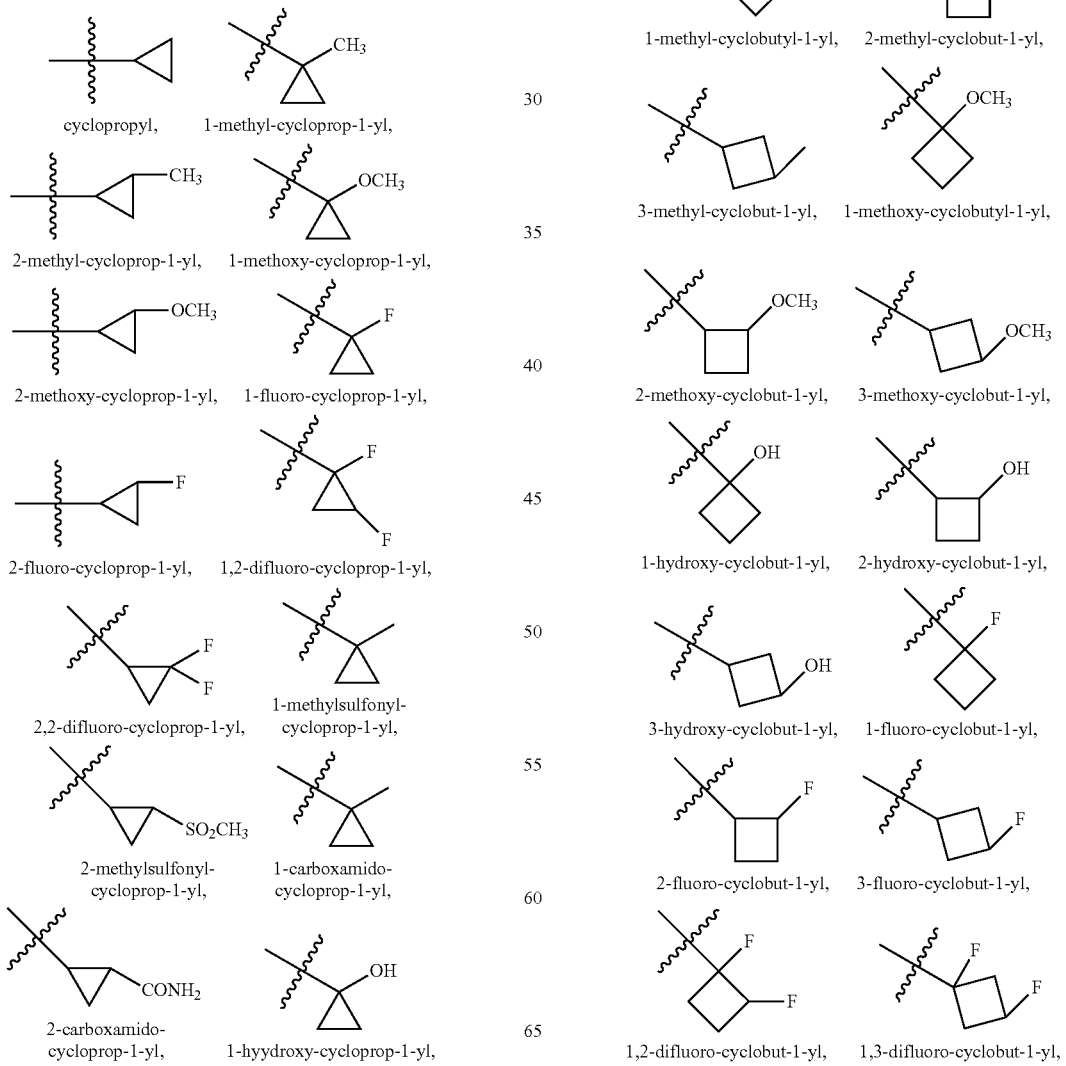

cyclopropyl, 1-methyl-cycloprop-1-yl, 2-methyl-cycloprop-1-yl, 1-methoxy-cycloprop-1-yl, 2-methoxy-cycloprop-1-yl, 1-fluoro-cycloprop-1-yl, 2-fluoro-cycloprop-1-yl, 1,2-difluoro-cycloprop-1-yl, 2,2-difluoro-cycloprop-1-yl, 1-methylsulfonyl-cycloprop-1-yl, 2-methylsulfonyl-cycloprop-1-yl, 1-carboxamido-cycloprop-1-yl, 2-carboxamido-cycloprop-1-yl, 1-hyydroxy-cycloprop-1-yl, 2-hydroxy-cycloprop-1-yl, 1-amino-cycloprop-1-yl, 2-amino-cycloprop-1-yl, 1-dimethylamino-cycloprop-1-yl, 2-dimethylamino-cycloprop-1-yl, cyclobutyl, 1-methyl-cyclobutyl-1-yl, 2-methyl-cyclobut-1-yl, 3-methyl-cyclobut-1-yl, 1-methoxy-cyclobutyl-1-yl, 2-methoxy-cyclobut-1-yl, 3-methoxy-cyclobut-1-yl, 1-hydroxy-cyclobut-1-yl, 2-hydroxy-cyclobut-1-yl, 3-hydroxy-cyclobut-1-yl, 1-fluoro-cyclobut-1-yl, 2-fluoro-cyclobut-1-yl, 3-fluoro-cyclobut-1-yl, 1,2-difluoro-cyclobut-1-yl, 1,3-difluoro-cyclobut-1-yl,

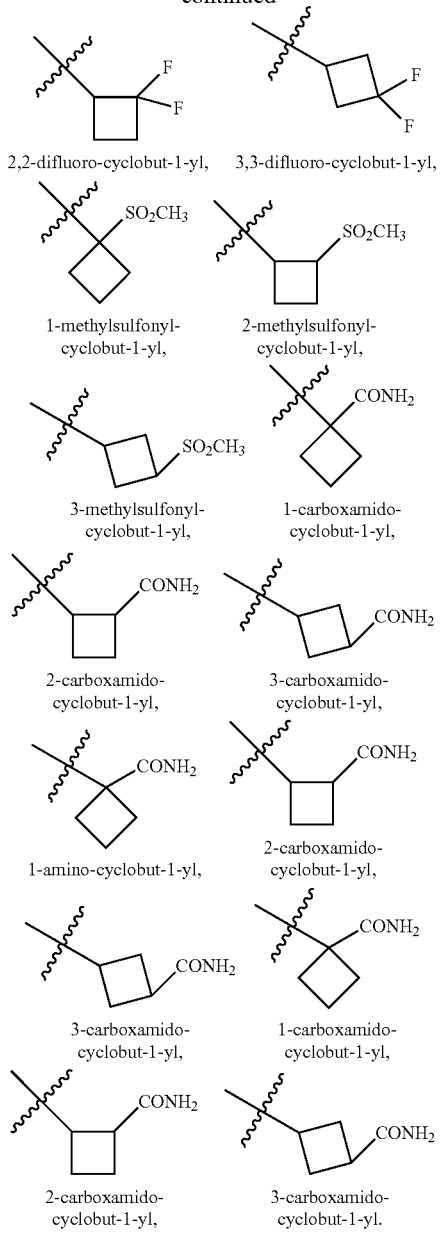

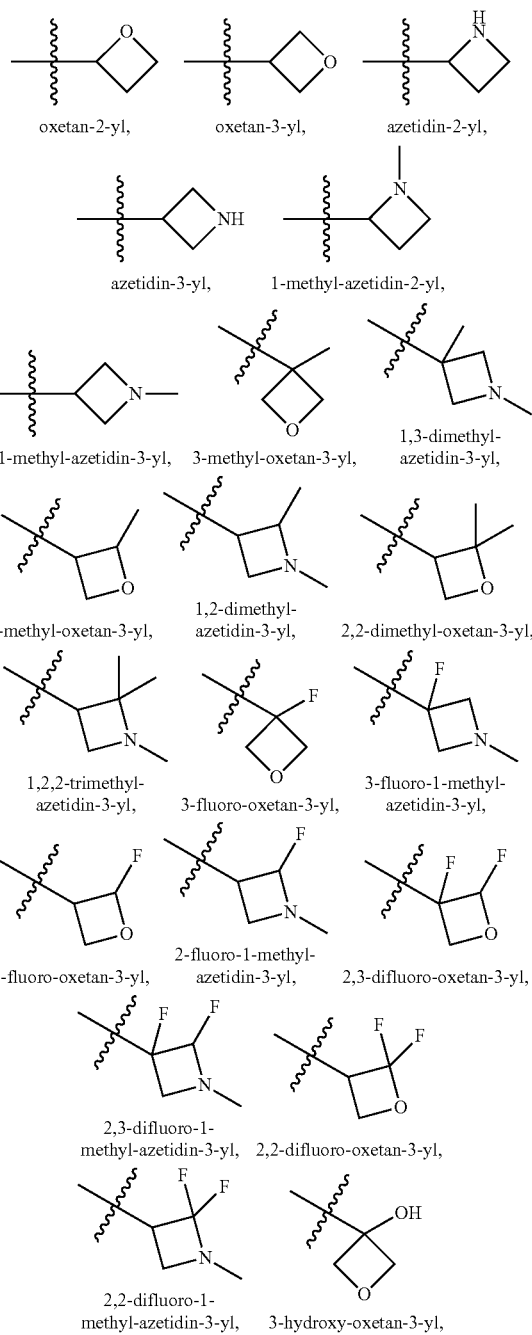

In yet another embodiment of the first aspect of the invention, the compound according to general formula (I) or (II) is characterized in that R$^{3a}$ is 3 to 7 membered heterocyclyl, wherein said 3 to 7 membered heterocyclyl is characterized contains one or two heteroatoms or heteroatom groups independently selected from the group consisting of O, NH, N(CH$_3$), S(=O) and S(=O)$_2$;

and wherein said 3 to 7 membered heterocyclyl is unsubstituted or substituted by one or two or three or four substituents independently selected from the group consisting of F, Cl, CH$_3$, CFH$_2$, CHF$_2$, CF$_3$, OH, OCH$_3$, CH$_2$OH, CH$_2$OCH$_3$, OCFH$_2$, OCHF$_2$, OCF$_3$, S(=O)$_2$CH$_3$, S(=O)$_2$CHF$_2$, S(=O)$_2$CF$_3$, NH$_2$, NH(CH$_3$), N(CH$_3$)$_2$, C(=O)NH$_2$, C(=O)NH(CH$_3$) and C(=O)N(CH$_3$)$_2$.

Preferably, R$^{3a}$ is 3 to 7 membered heterocyclyl, wherein said 3 to 7 membered heterocyclyl is selected from the group consisting of oxetanyl, tetrahydrofuranyl, tetrahydropyranyl, 1,1-dioxo-thietanyl, azetidinyl, pyrrolidinyl, piperidinyl, piperazinyl, N-methylpiperazinyl or morpholinyl, wherein said 3 to 7 membered heterocyclyl is unsubstituted or substituted by one or two or three or four substituents independently selected from the group consisting of F, Cl, CH$_3$, CFH$_2$, CHF$_2$, CF$_3$, OH, OCH$_3$, OCFH$_2$, OCHF$_2$, OCF$_3$, S(=O)$_2$CH$_3$, S(=O)$_2$CHF$_2$, S(=O)$_2$CF$_3$, NH$_2$, NH(CH$_3$), N(CH$_3$)$_2$, C(=O)NH$_2$, C(=O)NH(CH$_3$) and C(=O)N(CH$_3$)$_2$.

Preferably,

L' is bond or CH$_2$ and R$^{3a}$ is selected from the group consisting of

-continued

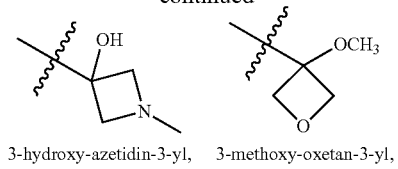

3-hydroxy-azetidin-3-yl, 3-methoxy-oxetan-3-yl,

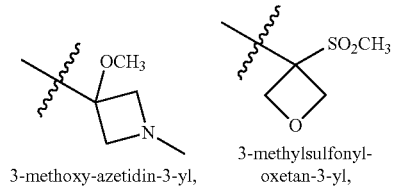

3-methoxy-azetidin-3-yl, 3-methylsulfonyl-oxetan-3-yl,

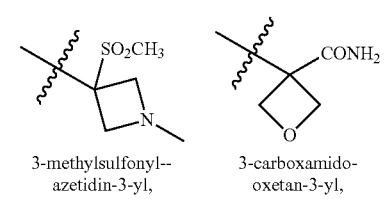

3-methylsulfonyl-azetidin-3-yl, 3-carboxamido-oxetan-3-yl,

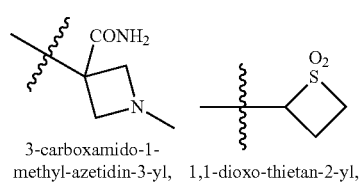

3-carboxamido-1-methyl-azetidin-3-yl, 1,1-dioxo-thietan-2-yl,

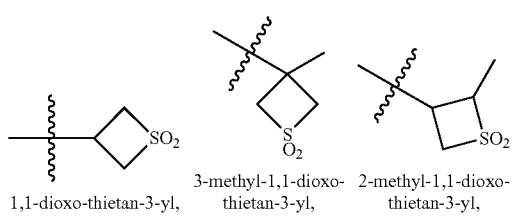

1,1-dioxo-thietan-3-yl, 3-methyl-1,1-dioxo-thietan-3-yl, 2-methyl-1,1-dioxo-thietan-3-yl,

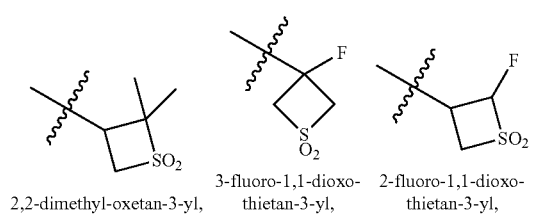

2,2-dimethyl-oxetan-3-yl, 3-fluoro-1,1-dioxo-thietan-3-yl, 2-fluoro-1,1-dioxo-thietan-3-yl,

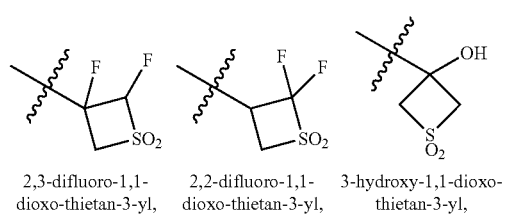

2,3-difluoro-1,1-dioxo-thietan-3-yl, 2,2-difluoro-1,1-dioxo-thietan-3-yl, 3-hydroxy-1,1-dioxo-thietan-3-yl, -continued

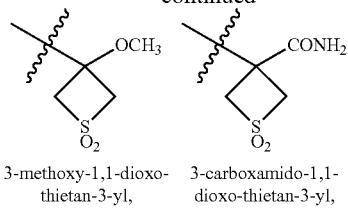

3-methoxy-1,1-dioxo-thietan-3-yl, 3-carboxamido-1,1-dioxo-thietan-3-yl, or $L'$ is $CH_2$ and $R^{3a}$ is selected from the group consisting of

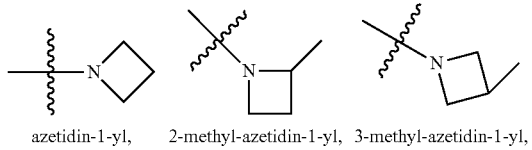

azetidin-1-yl, 2-methyl-azetidin-1-yl, 3-methyl-azetidin-1-yl,

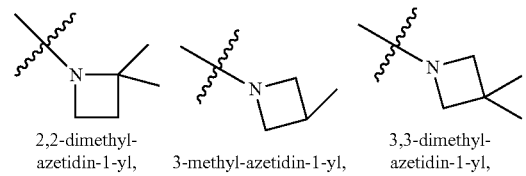

2,2-dimethyl-azetidin-1-yl, 3-methyl-azetidin-1-yl, 3,3-dimethyl-azetidin-1-yl,

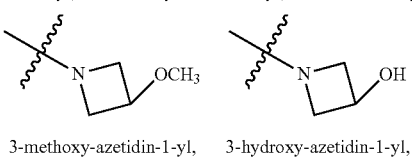

3-methoxy-azetidin-1-yl, 3-hydroxy-azetidin-1-yl,

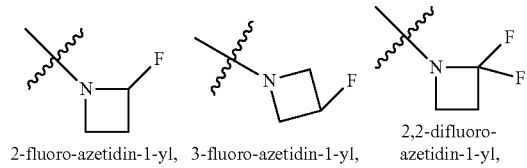

2-fluoro-azetidin-1-yl, 3-fluoro-azetidin-1-yl, 2,2-difluoro-azetidin-1-yl,

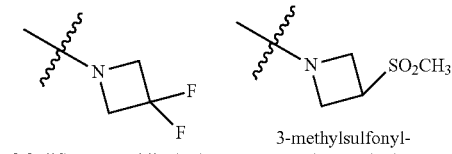

3,3-difluoro-azetidin-1-yl, 3-methylsulfonyl-cycloprop-1-yl,

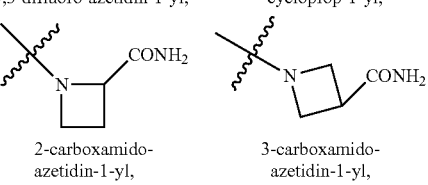

2-carboxamido-azetidin-1-yl, 3-carboxamido-azetidin-1-yl,

In another embodiment of the first aspect of the invention, the compound according to general formula (I) or (II) is characterized in that $R^3$ is selected from the group consisting of $CH_2OH$, $CH_2CH_2OH$, $CH_2CH_2OCH_3$, $CH(CH_3)CH_2OH$, $CH(CH_3)CH_2OCH_3$, $C(CH_3)_2CH_2OH$, $C(CH_3)_2CH_2OCH_3$, $CH_2S(=O)_2CH_3$, $CH_2CH_2S(=O)_2CH_3$, $C(CH_3)_2CH_2S(=O)_2CH_3$, $CH_2CH_2N(CH_3)_2$, $C(CH_3)_2CH_2N(CH_3)_2$, $CH_2C(=O)N(CH_3)_2$, $CH_2C(=O)NH(CH_3)$, $CH_2C(=O)NH_2$, $CH_2C(=O)OH$, $CH_2CH_2C(=O)N(CH_3)_2$, $CH_2CH_2C(=O)NH(CH_3)$, $CH_2CH_2C(=O)NH_2$, $C(CH_3)_2CH_2C(=O)N(CH_3)_2$, $C(CH_3)_2CH_2C(=O)NH(CH_3)$, $C(CH_3)_2CH_2C(=O)NH_2$, $CH_2C(CH_3)_2C(=O)NH_2$, $C(CH_3)_2C(=O)NH_2$, $CH_2C(CH_3)_2C(=O)NH(CH_3)$, $CH_2C(CH_3)_2C(=O)NH_2$, $CH_2C(=O)OH$, $CH_2CH_2CH_2OH$, $CH_2CH_2CH_2OCH_3$, $CH_2CH_2CH_2S(=O)_2CH_3$, $CH_2CH_2CH_2N(CH_3)_2$, $CH_2CH_2CH_2C(=O)N(CH_3)_2$, $CH_2CH_2CH_2C(=O)NH(CH_3)$, $CH_2CH_2CH_2C(=O)NH_2$, $CH_2C(CH_2)_2NH_2$ ((1- amino-cycloprop-1-yl)methyl), oxetanyl, $CH_2C(H)(CH_2)_2O$ ((oxetan-3-yl)-methyl), $CH_2C(OH)(CH_2)_2O$ ((3-hydroxy-oxetan-3-yl)-methyl) and 1,1-dioxo-thietanyl.

In preferred embodiment of the first aspect of the invention, the compound according to general formula (I) or (II) is characterized in that $R^3$ is selected from the group consisting of $CH_2OH$, $CH_2CH_2OH$, $CH_2CH_2OCH_3$, $CH(CH_3)CH_2OH$, $C(CH_3)_2CH_2OH$, $CH_2S(=O)_2CH_3$, $CH_2CH_2S(=O)_2CH_3$, $CH_2CH_2N(CH_3)_2$, $CH_2C(=O)OH$, $CH_2C(=O)NH_2$, $CH_2C(=O)N(CH_3)_2$, $CH_2C(=O)NH(CH_3)$, $CH_2CH_2C(=O)NH_2$, $C(CH_3)_2C(=O)NH_2$, $CH_2C(CH_3)_2C(=O)NH_2$, $CH_2CH_2CH_2OH$, $CH_2CH_2CH_2OCH_3$, $CH_2C(CH_2)_2NH_2$ ((1-amino-cycloprop-1-yl)methyl), 3-oxetanyl, $CH_2C(OH)(CH_2)_2O$ ((3-hydroxy-oxetan-3-yl)-methyl) and 1,1-dioxo-thietan-3-yl.

In yet another embodiment of the first aspect of the invention, the compound according to general formula (I) or (II) is characterized in that $R^4$ represents $L-R^5$, wherein L is bond, $CH_2$, $C(CH_3)_2$, O or $S(=O)_2$. Preferably, L is bond or $CH_2$ or $SO_2$.

In yet another embodiment of the first aspect of the invention, the compound according to general formula (I) or (II) is characterized in that $R^5$ is $C_{1-6}$-alkyl, wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$.

In yet another embodiment of the first aspect of the invention, the compound according to general formula (I) or (II) is characterized in that $R^5$ is $C_{3-6}$-cycloalkyl, wherein said $C_{3-6}$-cycloalkyl is unsubstituted or substituted by one or two or three or four substituents independently selected from the group consisting of F, Cl, CN, $CH_3$, $CFH_2$, $CHF_2$, $CF_3$, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$.

Preferably, $R^5$ is $C_{3-6}$-cycloalkyl, wherein said $C_{3-6}$-cycloalkyl is cyclopropyl or cyclobutyl, wherein said cyclopropyl or said cyclobutyl is unsubstituted or substituted by one or two or three or four substituents independently selected from the group consisting of F, Cl, CN, $CH_3$, $CFH_2$, $CHF_2$, $CF_3$, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$.

In yet another embodiment of the first aspect of the invention, the compound according to general formula (I) or (II) is characterized in that $R^5$ is 3 to 7 membered heterocyclyl, wherein said 3 to 7 membered heterocyclyl is characterized that it contains one heteroatom or heteroatom group, selected from O, NH, $N(CH_3)$, $S(=O)$ and $S(=O)_2$;

and wherein said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$.

Preferably, $R^5$ is 3 to 7 membered heterocyclyl, wherein said 3 to 7 membered heterocyclyl is selected from the group consisting of oxetanyl, tetrahydrofuranyl, tetrahydropyranyl, azetidinyl, pyrrolidinyl, piperidinyl, piperazinyl, N-methylpiperazinyl or morpholinyl, wherein said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$.

In yet another embodiment of the first aspect of the invention, the compound according to general formula (I) or (II) is characterized in that L is bond and $R^5$ is selected from the group consisting of $CH_3$, $CH(CH_3)_2$, $C(CH_3)_3$, $CH_2OH$, $CH_2OCH_3$, $CH_2OCFH_2$, $CH_2OCHF_2$, $CH_2OCF_3$, $CH_2S(=O)_2CH_3$, $CH_2S(=O)_2CHF_2$, $CH_2S(=O)_2CF_3$, $CH_2S(=O)_2CFH_2$, $CH_2S(=O)_2CH(CH_3)_2$, $CH_2S(=O)_2$(c-propyl), $CFH_2$, $CHF_2$, $CF_3$, $CH_2CF_3$, $CF_2CH_3$, $CH_2CFH_2$, $CH_2CHF_2$, $CH_2CH_2CF_3$, $CH_2CH_2OCH_3$, $CH_2CH_2OH$, $C(CH_3)_2CH_2OCH_3$, $C(CH_3)_2CH_2OH$, $CH_2CH_2S(=O)_2CH_3$, $CH_2CH_2N(CH_3)_2$, $CH_2C(=O)NH_2$, $CH_2C(=O)NH(CH_3)$, $CH_2C(=O)N(CH_3)_2$, $CH_2CH_2C(=O)NH_2$, $CH_2CH_2C(=O)NH(CH_3)$, $CH_2CH_2C(=O)N(CH_3)_2$, $C(CH_3)_2OCH_3$, $C(CH_3)_2OH$, $C(CH_3)_2S(=O)_2CH_3$, $C(CH_3)_2S(=O)_2CHF_2$, $C(CH_3)_2S(=O)_2CF_3$, $C(CH_3)_2S(=O)_2CFH_2$, $C(CH_3)_2N(CH_3)_2$, $C(CH_3)_2C(=O)NH_2$ $C(CH_3)_2C(=O)NH(CH_3)$, $C(CH_3)_2C(=O)N(CH_3)_2$, cyclopropyl, cyclobuytyl or oxetanyl, wherein said cyclopropyl, cyclobutyl or oxetanyl are unsubstituted or substituted with OH, $OCH_3$ or $S(O)_2CH_3$;

or

L is $CH_2$ and $R^5$ is selected from the group consisting of $CH_3$, $CH_2OH$, $CH_2OCH_3$, $CH_2OCFH_2$, $CH_2OCHF_2$, $CH_2OCF_3$, $CH_2S(=O)_2CH_3$, $CH_2S(=O)_2CHF_2$, $CH_2S(=O)_2CF_3$, $CH_2S(=O)_2CFH_2$, $CH_2S(=O)_2CH(CH_3)_2$, $CH_2S(=O)_2$(c-propyl), $CH(CH_3)_2$, $C(CH_3)_3$, $CFH_2$, $CHF_2$, $CF_3$, $CH_2CF_3$, $CF_2CH_3$, $CH_2CFH_2$, $CH_2CHF_2$, $CH_2CH_2CF_3$, $CH_2CH_2OCH_3$, $CH_2CH_2OH$, $C(CH_3)_2CH_2OCH_3$, $C(CH_3)_2CH_2OH$, $CH_2CH_2S(=O)_2CH_3$, $CH_2CH_2N(CH_3)_2$, $CH_2C(=O)NH_2$, $CH_2C(=O)NH(CH_3)$, $CH_2C(=O)N(CH_3)_2$, $CH_2CH_2C(=O)NH_2$, $CH_2CH_2C(=O)NH(CH_3)$, $CH_2CH_2C(=O)N(CH_3)_2$, $C(CH_3)_2OCH_3$, $C(CH_3)_2OH$, $C(CH_3)_2S(=O)_2CH_3$, $C(CH_3)_2S(=O)_2CHF_2$, $C(CH_3)_2S(=O)_2CF_3$, $C(CH_3)_2S(=O)_2CFH_2$, $C(CH_3)_2S(=O)_2CH(CH_3)_2$, $C(CH_3)_2S(=O)_2$(c-propyl), $C(CH_3)_2N(CH_3)_2$, $C(CH_3)_2C(=O)NH_2$ $C(CH_3)_2C(=O)NH(CH_3)$, $C(CH_3)_2C(=O)N(CH_3)_2$, cyclopropyl, cyclobuytyl or oxetanyl, wherein said cyclopropyl, cyclobuytyl or oxetanyl are unsubstituted or substituted with $CH_3$, OH, $NH_2$, $NH(CH_3)$, $N(CH_3)_2$, $OCH_3$ or $S(O)_2CH_3$;

or

L is $C(CH_3)_2$ and $R^5$ is selected from the group consisting of $CH(CH_3)_2$, $C(CH_3)_3$, $CH_2OH$, $CH_2OCH_3$, $CH_2OCFH_2$, $CH_2OCHF_2$, $CH_2OCF_3$, $CH_2S(=O)_2CH_3$, $CH_2S(=O)_2CHF_2$, $CH_2S (=O)₂CF₃, CH₂S(=O)₂CFH₂, CH₂S(=O)₂CH(CH₃)₂, CH₂S(=O)₂(c-propyl), CFH₂, CHF₂, CF₃, CH₂CF₃, CF₂CH₃, CH₂CFH₂, CH₂CHF₂, CH₂CH₂CF₃, CH₂CH₂OCH₃, CH₂CH₂OH, C(CH₃)₂CH₂OCH₃, C(CH₃)₂ CH₂OH, CH₂CH₂S(=O)₂CH₃, CH₂CH₂N(CH₃)₂, CH₂C (=O)NH₂, CH₂C(=O)NH(CH₃), CH₂C(=O)N(CH₃)₂, CH₂CH₂C(=O)NH₂, CH₂CH₂C(=O)NH(CH₃), CH₂CH₂C(=O)N(CH₃)₂, C(CH₃)₂OCH₃, C(CH₃)₂OH, C(CH₃)₂S(=O)₂CH₃, C(CH₃)₂S(=O)₂CHF₂, C(CH₃)₂S (=O)₂CF₃, C(CH₃)₂S(=O)₂CFH₂, C(CH₃)₂S(=O)₂CH (CH₃)₂, C(CH₃)₂S(=O)₂(c-propyl), C(CH₃)₂N(CH₃)₂, C(CH₃)₂C(=O)NH₂ C(CH₃)₂C(=O)NH(CH₃), C(CH₃)₂C (=O)N(CH₃)₂, cyclopropyl, cyclobuytyl or oxetanyl, wherein said cyclopropyl, cyclobuytyl or oxetanyl are unsubstituted or substituted with CH₃, OH, NH₂, NH(CH₃), N(CH₃)₂, OCH₃ or S(O)₂CH₃;

or

L is O and

R⁵ is selected from the group consisting of CH₃, CH (CH₃)₂, C(CH₃)₃, CFH₂, CHF₂, CF₃, CH₂CF₃, CF₂CH₃, CH₂CFH₂, CH₂CHF₂, CH₂CH₂CF₃, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N (CH₃)₂, CH₂CH₂C(=O)NH₂ CH₂CH₂C(=O)NH(CH₃), CH₂CH₂C(=O)N(CH₃)₂, C(CH₃)₂OCH₃, C(CH₃)₂N (CH₃)₂, C(CH₃)₂C(=O)NH₂ C(CH₃)₂C(=O)NH(CH₃), C(CH₃)₂C(=O)N(CH₃)₂, cyclopropyl, cyclobuytyl or oxetanyl, wherein said cyclopropyl, cyclobuytyl or oxetanyl are unsubstituted or substituted with CH₃, OCH₃ or S(O)₂CH₃;

or

L is S(=O)₂ and

R⁵ is selected from the group consisting of CH₃, CH₂CH₃, CH(CH₃)₂, C(CH₃)₃, CFH₂, CHF₂, CF₃, CH₂CF₃, CF₂CH₃, CH₂CFH₂, CH₂CHF₂, CH₂CH₂CF₃, CH₂CH₂OCH₃, CH₂CH₂OH, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N(CH₃)₂, CH₂CH₂C (=O)NH₂ CH₂CH₂C(=O)NH(CH₃), CH₂CH₂C(=O)N (CH₃)₂, cyclopropyl, cyclobuytyl or oxetanyl, wherein said cyclopropyl, cyclobuytyl or oxetanyl are unsubstituted or substituted with CH₃, OCH₃ or S(O)₂CH₃.

In yet another embodiment of the first aspect of the invention, the compound according to general formula (I) or (II) is characterized in that R⁴ is selected from the group consisting of CF₃, CHF₂, CF₂CH₃, CH₂CHF₂, CH₂CF₃, CH(CH₃)₂, C(CH₃)₃, OCF₃, OCHF₂, OCH₂CF₃, O-c-propyl (cycloprop-1-yl-oxy), CH₂OCF₃, C(CH₃)₂OH, S(=O)₂CHF₂, S(=O)₂CF₃, S(=O)₂CH₂CH₂OCH₃, S(=O)₂CH₂CH₂OH, S(=O)₂ CH₂CF₃, S(=O)₂CF₂CH₃, S(=O)₂CH₂CHF₂, S(=O)₂— CH(CH₂)₂O (S(=O)₂-oxetan-3-yl), CH₂S(=O)₂CHF₂, CH₂S(=O)₂CF₃, CH₂CH₂S(=O)₂CH₃, C(CH₃)₂S(=O)₂ CH₃, cyclopropyl, C(CH₂)₂(CH₃) (1-methyl-cycloprop-1-yl), C(CH₂)₂S(=O)₂CH₃ (1-methylsulfonyl-cycloprop-1-yl), C(OH)(CH₂)₂O (3-hydroxy-oxetan-3-yl), cyclobutyl.

Yet another embodiment of the first aspect of the invention is characterized in that the compound of general formula (I) is selected from a compound according to general formula (IIIa), (IIIb), (IIIc), (IIId), (IIIe), (IIIg), (IIIh), (IIIj), (IIIk), (IIIm), (IIIn), (IIIn-1), (IIIn-2), (IIIo), (IIIp), (IIIq), (IIIr), (IIIs), (IIIt), (IIIu), (IIIv), (IIIw), (IIIx), (IIIy), (IIIy-1) and (IIIz):

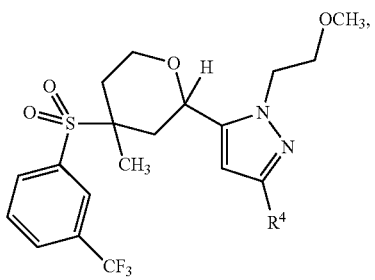

(IIIa)

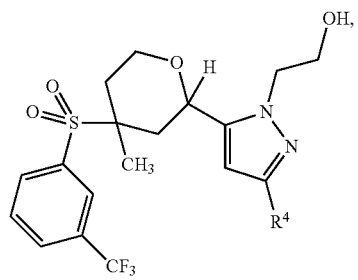

(IIIb)

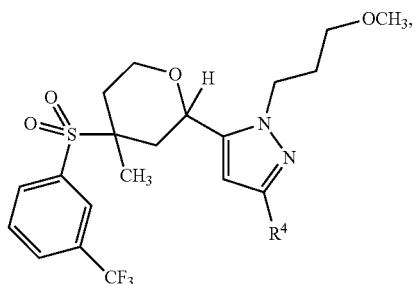

(IIIc)

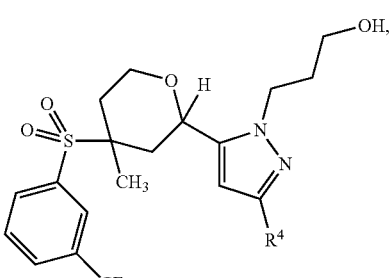

(IIId)

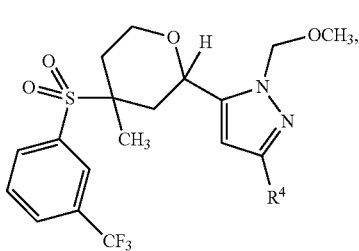

(IIIe)

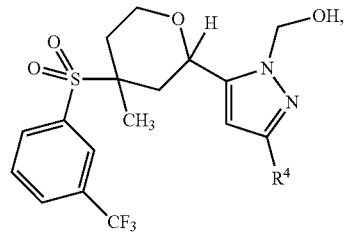

(IIIf)

(IIIg)
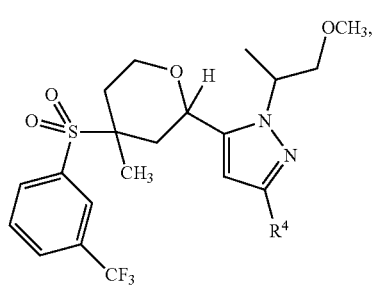
(IIIh)
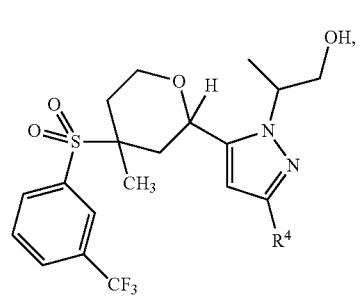
(IIIj)
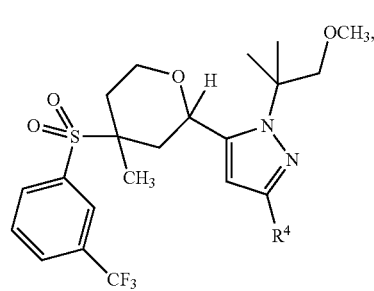
(IIIk)
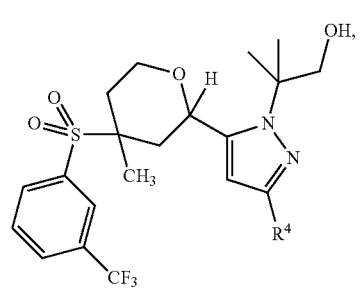
(IIIm)
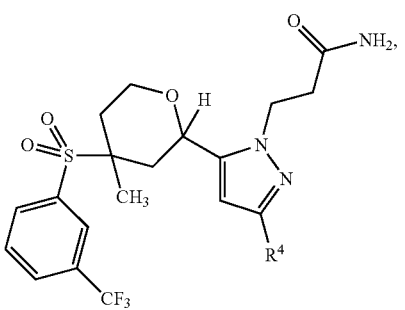
(IIIn)
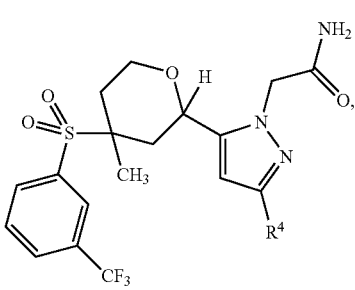
(IIIn-1)
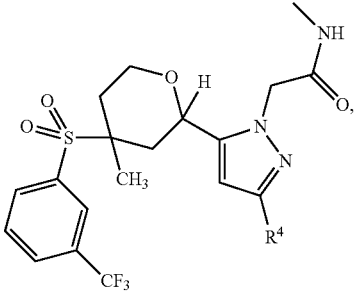
(IIIn-2)
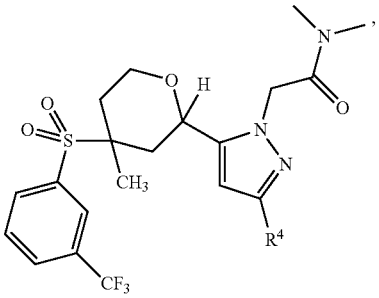
(IIIo)
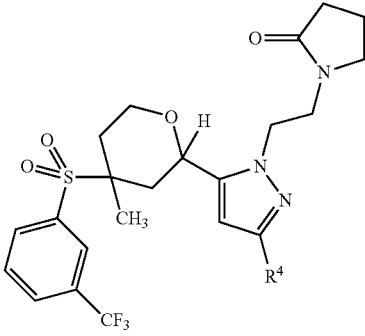
(IIIp)
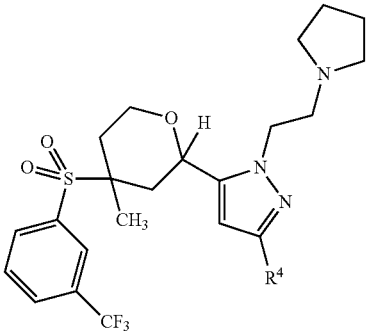

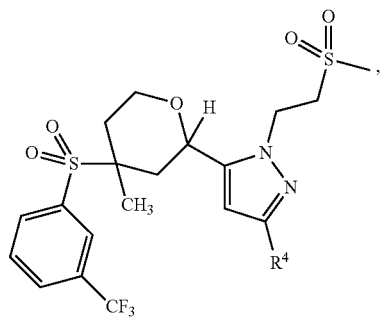
(IIIq)
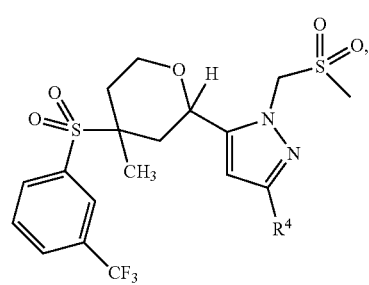
(IIIr)
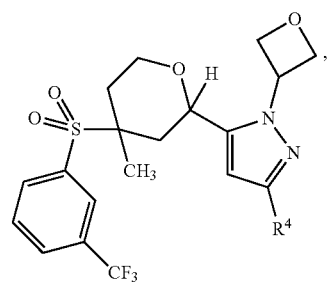
(IIIs)
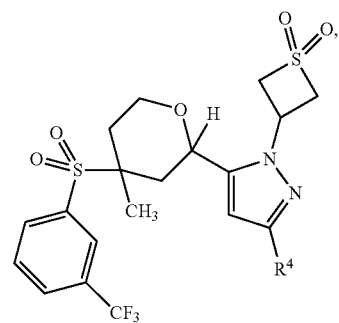
(IIIt)
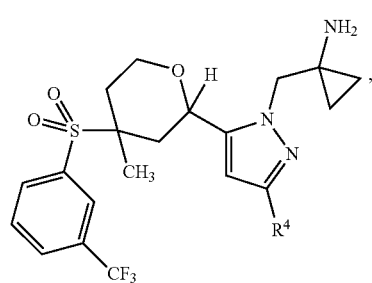
(IIIu)
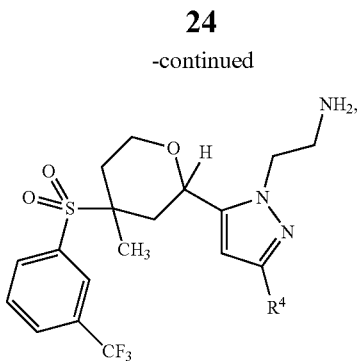
(IIIv)
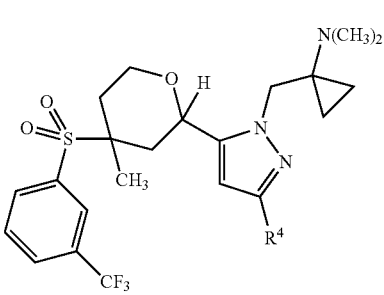
(IIIw)
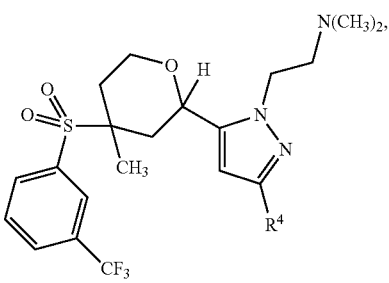
(IIIx)
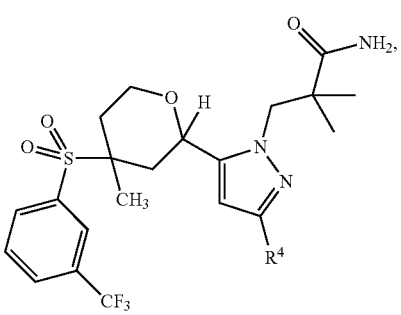
(IIIy)
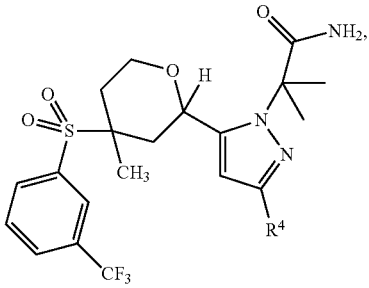
(IIIy-1)

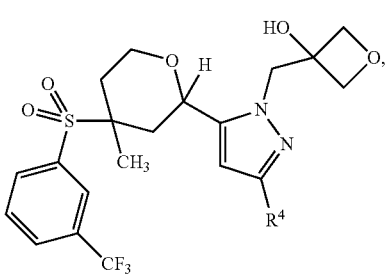

(IIIz)

wherein R⁴ is defined as above, with the proviso that if the compound of general formula (I) is selected from a compound according to general formula (IIIa), then $R^4$ is not $CF_3$, optionally in the form of a single stereoisomer or a mixture of stereoisomers, in the form of the free compound and/or a physiologically acceptable salt and/or a physiologically acceptable solvate thereof.

Particularly preferred compounds according to the invention are selected from the group consisting of
1  [5-[4-Methyl-4-[[3-(trifluoromethyl)phenyl]sulfonyl]-tetrahydro-pyran-2-yl]-3-(trifluoromethyl)-1H-pyrazol-1-yl]-methanol
2  2-[5-[4-Methyl-4-[[3-(trifluoromethyl)phenyl]sulfonyl]-tetrahydro-pyran-2-yl]-3-(trifluoromethyl)-1H-pyrazol-1-yl]-ethanol
4  2-[3-Methylsulfonyl-5-[4-methyl-4-[[3-(trifluoromethyl)phenyl]sulfonyl]-tetrahydro-pyran-2-yl]-1H-pyrazol-1-yl]-ethanol
5  3-(Difluoromethyl)-1-(methoxymethyl)-5-(4-methyl-4-((3-(trifluoromethyl)phenyl)-sulfonyl)tetrahydro-2H-pyran-2-yl)-1H-pyrazole
6  2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol
7  2-Methyl-2-[3-methylsulfonyl-5-[4-methyl-4-[[3-(trifluoromethyl)phenyl]sulfonyl]-tetrahydro-pyran-2-yl]-1H-pyrazol-1-yl]-propan-1-ol
8  3-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-oxetan-3-ol
9  3-[5-[4-Methyl-4-[[3-(trifluoromethyl)phenyl]sulfonyl]-tetrahydro-pyran-2-yl]-3-(trifluoromethyl)-1H-pyrazol-1-yl]-propan-1-ol
10  1-(3-Methoxypropyl)-5-(4-methyl-4-((3-(trifluoromethyl)phenyl)sulfonyl)tetrahydro-2H-pyran-2-yl)-3-(trifluoromethyl)-1H-pyrazole
11  2-[5-[4-Methyl-4-[[3-(trifluoromethyl)phenyl]sulfonyl]-tetrahydro-pyran-2-yl]-3-(trifluoromethyl)-1H-pyrazol-1-yl]-acetamide
12  3-[5-[4-Methyl-4-[[3-(trifluoromethyl)phenyl]sulfonyl]-tetrahydro-pyran-2-yl]-3-(trifluoromethyl)-1H-pyrazol-1-yl]-propionamide
13  2,2-Dimethyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propionamide
14  Dimethyl-[2-[5-[4-methyl-4-[[3-(trifluoromethyl)phenyl]sulfonyl]-tetrahydro-pyran-2-yl]-3-(trifluoromethyl)-1H-pyrazol-1-yl]-ethyl]-amine
15  [1-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-cyclopropyl]-amine
16  [1-[[3-Methylsulfonyl-5-[4-methyl-4-[[3-(trifluoromethyl)phenyl]sulfonyl]-tetrahydro-pyran-2-yl]-1H-pyrazol-1-yl]-methyl]-cyclopropyl]-amine
17  5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole
18  1-(Methylsulfonyl-methyl)-5-[4-methyl-4-[[3-(trifluoromethyl)phenyl]sulfonyl]-tetrahydro-pyran-2-yl]-3-(trifluoromethyl)-1H-pyrazole
19  1-(2-Methylsulfonyl-ethyl)-5-[4-methyl-4-[[3-(trifluoromethyl)phenyl]sulfonyl]-tetrahydro-pyran-2-yl]-3-(trifluoromethyl)-1H-pyrazole
20  3-[5-[4-Methyl-4-[[3-(trifluoromethyl)phenyl]sulfonyl]-tetrahydro-pyran-2-yl]-3-(trifluoromethyl)-1H-pyrazol-1-yl]-thietane-1,1-dioxide
21  1-(Methoxymethyl)-5-[4-methyl-4-[[3-(trifluoromethyl)phenyl]sulfonyl]-tetrahydro-pyran-2-yl]-3-(trifluoromethyl)-1H-pyrazole
22  1-[2-[5-[4-Methyl-4-[[3-(trifluoromethyl)phenyl]sulfonyl]-tetrahydro-pyran-2-yl]-3-(trifluoromethyl)-1H-pyrazol-1-yl]-ethyl]-pyrrolidin-2-one
23  1-(2-Methoxyethyl)-5-(4-methyl-4-((3-(trifluoromethyl)phenyl)sulfonyl)tetrahydro-2H-pyran-2-yl)-3-(methylsulfonyl)-1H-pyrazole
24  2-Methyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol
25  2-[3-(Difluoro-methylsulfonyl)-5-[4-methyl-4-[[3-(trifluoromethyl)phenyl]sulfonyl]-tetrahydro-pyran-2-yl]-1H-pyrazol-1-yl]-ethanol
26  2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propionamide
28  N,N-Dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide
29  N-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide optionally in the form of a single stereoisomer or a mixture of stereoisomers, in the form of the free compound and/or a physiologically acceptable salt or solvate thereof.

Within the scope of the invention, it is understood that the compounds according the aforesaid list may be in the form of a single stereoisomer or any mixture of stereoisomers.

For instance, the given compound 5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole (Example 17),

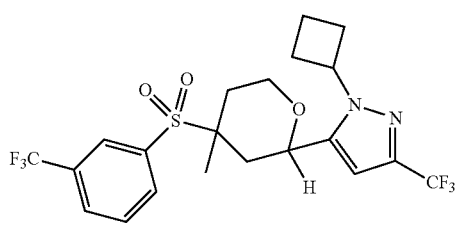 [SMILES: CC1(S(=O)(=O)c2cccc(C(F)(F)F)c2)CCOC(c2cc(C(F)(F)F)nn2C2CCC2)C1]

represents cis-rac-5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole,

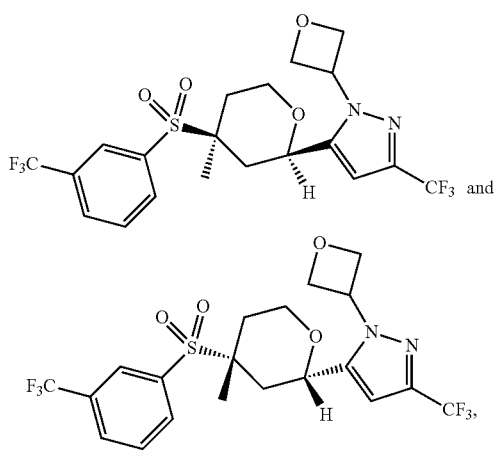

[(2R,4S) and (2S,4R)-5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole, and trans-rac-5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole,

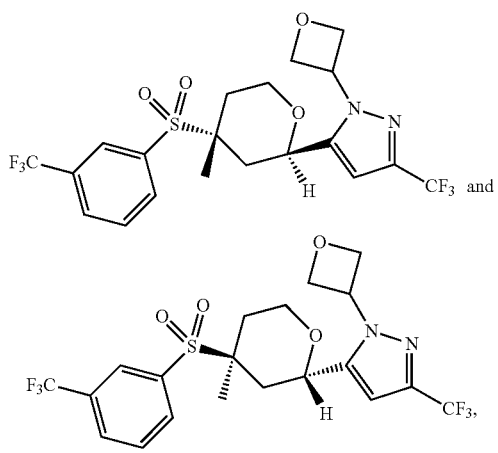

[(2S,4S) and (2R,4R)-5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole, as well as each individual stereoisomer or any other mixture thereof.

Furthermore, preference may be given to compounds according to the invention that cause at least a 50% inhibition, which is present at a concentration of 3 μM, in a fluorescent assay for CaV2.2 channels with HEK293 cells in which human CaV2.2 channels were stably expressed at a concentration of less 3 μM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The present invention further relates to a compound according to the present invention for CaV2.2 calcium channel regulation, preferably for use in CaV2.2 calcium channel blockage. The present invention therefore further relates to a compound according to the present invention for use in the treatment and/or prophylaxis of disorders and/or diseases which are mediated, at least in part, at least in part, by CaV2.2 channels. The term "disorders and/or diseases which are mediated, at least in part, by CaV2.2 channels", is intended to include each of or all of the disease states.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for use in the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for use in the treatment and/or prophylaxis of pain, in particular acute pain and/or chronic pain and/or visceral pain and/or headache pain and/or inflammatory pain and/or mixed pain. Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headachepain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularily suitable for use in the treatment and/or prophylaxis of mood disorders. Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularily suitable for use in the treatment and/or prophylaxis of epilepsy. Epilepsy according to the invention might include partial seizures such as temporal lobe epilepsy, absence seizures generalized seizures, and tonic/clonic seizures.

In yet another embodiment of the invention, at least one compound according to the present invention is particularily suitable for use in the treatment and/or prophylaxis of neurodegenerative disorders. Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for use in the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74-79 (1941)) or by the formalin test (e.g. according to D. Dubuisson et al., Pain 1977, 4, 161-174).

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The reactions were, if necessary, carried out under an inert atmosphere (mostly $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The indication "equivalents" ("eq." or "eq" or "equiv.") means molar equivalents, "RT" or "rt" means room temperature T (23±7° C.), "M" are indications of concentration in mol/l, "aq." means aq., "sat." means sat., "sol." means solution, "conc." means concentrated and "anhydr." means anhydr. The mixing ratios of solvents are usually stated in the volume/volume ratio.

Further Abbreviations:

DCM=dichloromethane; DIPEA=N,N-diisopropylethylamine; DME=1,2-dimethoxyethane; DMF=N,N-dimethylformamide; DMSO=dimethylsulfoxide; EtOAc=ethyl acetate; EtOH=ethanol; h=hour(s); IPA=iso-propanol; KOt-Bu=potassium tert-butoxide; LDA=lithium diisopropylamide; m-CPBA=3-Chloroperoxybenzoic acid; min=minute(s); MeOH=methanol; MS=methanesulfonyl; MOM=methoxymethyl acetal; NOE=Nuclear Overhauser Effect; NOESY=Nuclear Overhauser effect spectroscopy; PdCl$_2$(dppf)$_2$=[1,1'-Bis(diphenyl-phosphino)ferrocene]dichloropalladium(II); PE=petroleum ether; PMB=paramethoxybenzyl; RM=reaction mixture; SEM=[2-(trimethylsilyl)ethoxy]methyl acetal; TEA=triethylamine; TFA=trifluoroacetic acid; THF=tetrahydrofuran.

Instruments:

$^1$H-NMR-spectra (including NOESYs) were recorded on an Agilent 300 MHz or 400 MHz, or a Bruker 400 MHz or 500 MHz spectrometer.

Analytical SFC were performed on Thar SFC analytical or HPLC was performed on a Waters 2695 separation module Detector 2996 & Agilent 1200 series with G 1315B detector.

Preparative SFC were performed on THAR-SFC 80 or 200, or a Waters SFC Prep 100 q.

LCMS analytics were carried out on the following instruments:

1) Instrument-1 Agilent-1290 Infinity 6150 Quadra pole lcms Source: ESI (Agilent jet spray source)
2) Instrument-2 Agilent-1200 series 6130 Quadra pole lcms Source: Multi mode (ESI+APCI)

Cis/Trans Assignment

The cis racemic [cis-rac] and trans racemic [trans-rac] compounds were mostly separated after the methylation step using column chromatography or prep-HPLC. The assignment of cis racemic [cis-rac] versus trans racemic [trans-rac] was carried out by NOE studies. Formation of the cis racemic [cis-rac] isomer is generally favoured over formation of the trans racemic [trans-rac] isomer.

Regio Chemistry Assignment

The regiochemistry of N-alkylated pyrazole compounds was assigned by NOE studies.

Synthesis of Example Compounds

2-[5-[4-Methyl-4-[[3-(trifluoromethyl)phenyl]sulfonyl]-tetrahydro-pyran-2-yl]-3-(trifluoromethyl)-1H-pyrazol-1-yl]-ethanol (Example 2)

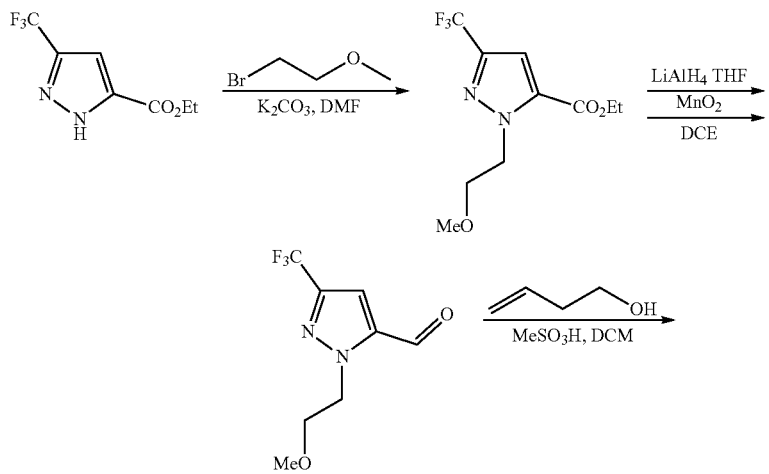

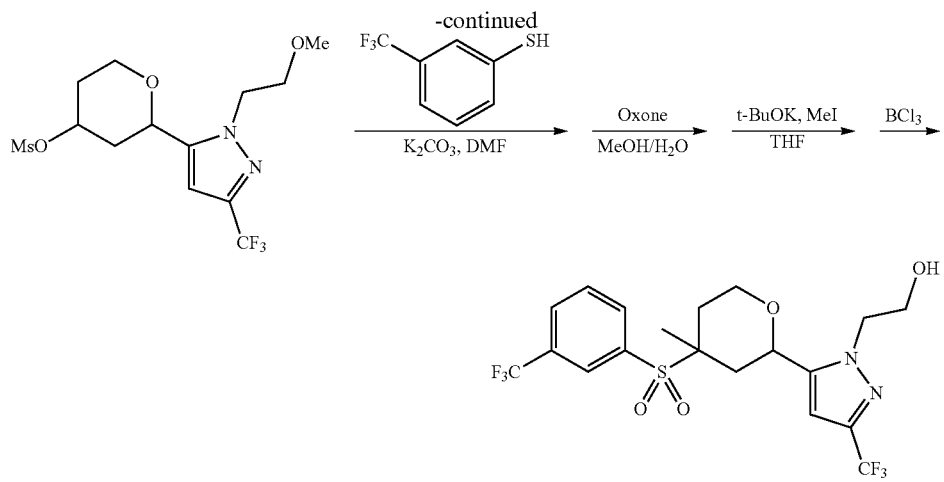

2

Step 1: Ethyl 1-(2-methoxyethyl)-3-(trifluoromethyl)-1H-pyrazole-5-carboxylate To a solution of ethyl 3-(trifluoromethyl)-1H-pyrazole-5-carboxylate (8 g, 38.46 mmol, 1 eq) in DMF (150 ml) was added K$_2$CO$_3$ (15.9 g, 115.38 mmol, 3 eq) and bromo ethyl methyl ether at 0° C. The RM was stirred at RT for 16 h. The RM was diluted with ice water (200 ml) and extracted with EtOAc (3×200 ml). The combined organic layers were washed with water (200 ml) and brine (200 ml), dried (Na$_2$SO$_4$) and upon concentration provided the crude product, which upon flash chromatography (silica gel; EtOAc-PE; 0:100→4:96) afforded the title compound (7.0 g, 68%).

Step 2: (1-(2-Methoxyethyl)-3-(trifluoromethyl)-1H-pyrazol-5-yl)methanol

Lithium aluminum hydride (2.99 g, 78.94 mmol, 3 eq) in THF (100 ml) was added dropwise to a solution of ethyl 1-(2-methoxyethyl)-3-(trifluoromethyl)-1H-pyrazole-5-carboxylate (7.0 g, 26.31 mmol, 1 eq) in THF (50 ml) at 0° C. The RM was stirred at RT for 2 h, quenched with saturated NH$_4$Cl solution (150 ml) at 0° C. and filtered through a bed of Celite. The filtrate was extracted with EtOAc (3×200 ml). The combined organic layers were washed with water (200 ml) and brine (200 ml), dried (Na$_2$SO$_4$) and upon concentration afforded the title compound (7.0 g).

Step 3: 1-(2-Methoxyethyl)-3-(trifluoromethyl)-1H-pyrazole-5-carbaldehyde

To a solution of (1-(2-methoxyethyl)-3-(trifluoromethyl)-1H-pyrazol-5-yl)methanol (7.0 g, 31.25 mmol, 1 eq) in 1,2-dichloroethane (150 ml), was added MnO$_2$ (8.15 g, 93.75 mmol, 3 eq) at RT and the RM was stirred at 90° C. for 16 h. After completion of the reaction, the mixture was filtered through Celite. The filtrate was concentrated and purified by flash chromatography (silica gel; EtOAc-PE; 0:100→18:82) to afford the title compound (2.2 g, 37% over 2 steps).

Step 4: 2-(1-(2-Methoxyethyl)-3-(trifluoromethyl)-1H-pyrazol-5-yl)tetrahydro-2H-pyran-4-yl methanesulfonate To a solution of 1-(2-methoxyethyl)-3-(trifluoromethyl)-1H-pyrazole-5-carbaldehyde (2.2 g, 9.909 mmol, 1 eq) in DCM (50 ml) was added 3-buten-1-ol (1.2 ml, 14.86 mmol, 1.5 eq) and methane sulfonic acid (6.4 ml, 99.09 mmol, 10 eq) at 0° C. and the RM was stirred at RT for 16 h. The RM was quenched with ice-water (100 ml) and basified with saturated Na$_2$CO$_3$ solution to pH~10. The aqueous layer was extracted with DCM (3×100 ml). The combined organic layers were washed with water (100 ml) and brine (100 ml), dried (Na$_2$SO$_4$) and upon concentration afforded the title compound (3.5 g).

Step 5: 1-(2-Methoxyethyl)-3-(trifluoromethyl)-5-(4-((3-(trifluoromethyl)phenyl)thio)tetrahydro-2H-pyran-2-yl)-1H-pyrazole To a solution of 2-(1-(2-methoxyethyl)-3-(trifluoromethyl)-1H-pyrazol-5-yl)tetrahydro-2H-pyran-4-yl methanesulfonate (2.5 ml, 18.81 mmol, 2 eq) in DMF (60 ml), was added K$_2$CO$_3$ (3.89 g, 28.22 mmol, 3 eq) followed by 3-(trifluoromethyl)benzenethiol (3.5 g, 9.40 mmol, 1 eq) and the RM was heated to 50° C. and stirred for 6 h and then at RT for 10 h. After completion of the reaction, the mixture was diluted with ice cold water (100 ml), extracted with EtOAc (3×100 ml), washed with water (100 ml) and brine (100 ml), dried (Na$_2$SO$_4$) and concentrated in vacuum to give the crude product, which was purified by flash chromatography (silica gel; EtOAc-PE; 0:100→1:4) to afford the title compound (3.4 g, 75% over 2 steps).

Step 6: 1-(2-Methoxyethyl)-3-(trifluoromethyl)-5-(4-((3-(trifluoromethyl)phenyl)sulfonyl)tetrahydro-2H-pyran-2-yl)-1H-pyrazole Oxone (6.89 g, 21.14 mmol, 3 eq) in water (30 ml) was added to a solution of 1-(2-methoxyethyl)-3-(trifluoromethyl)-5-(4-((3-(trifluoromethyl)phenyl)thio)tetrahydro-2H-pyran-2-yl)-1H-pyrazole (3.4 g, 7.48 mmol, 1 eq) in MeOH (30 ml) at RT and the RM was stirred for 16 h. After completion of the reaction, methanol was distilled off under reduced pressure and the residue was diluted with water (100 ml) and extracted with EtOAc (3×100 ml). The organics were washed with water (100 ml) and brine (100 ml), dried (Na$_2$SO$_4$) and concentrated to give the crude product, which upon flash chromatography (silica gel; EtOAc-PE; 0:100→35:65) afforded the title compound (2.0 g, 55%).

Step 7: [cis-rac] 1-(2-Methoxyethyl)-5-(4-methyl-4-((3-(trifluoromethyl)phenyl)sulfonyl)tetrahydro-2H-pyran-2-yl)-3-(trifluoromethyl)-1H-pyrazole To a solution of 1-(2-methoxyethyl)-3-(trifluoromethyl)-5-(4-((3-(trifluoromethyl)phenyl)sulfonyl)tetrahydro-2H-pyran-2-yl)-1H-pyrazole (2.0 g, 4.11 mmol, 1 eq) in THF (40 ml), cooled to −78° C., was added dropwise KOtBu (1 M solution in THF, 8.2 ml, 8.23 mmol, 2 eq), and the RM was stirred for 30 min before addition of methyl iodide (0.38 ml, 6.17 mmol, 1.5 eq). The RM was allowed to warm to RT and stirred for 16 h. The RM was quenched with water (50 ml) and extracted with EtOAc (3×100 ml). The combined organic layers were washed with water (100 ml) and brine (100 ml), dried (Na$_2$SO$_4$) and concentrated to give the crude product, which upon flash chromatography (silica gel; EtOAc-PE; 0:100→1:4) afforded the title cis and trans racemates.

[cis-rac] 1-(2-Methoxyethyl)-5-(4-methyl-4-((3-(trifluoromethyl)phenyl)sulfonyl)tetrahydro-2H-pyran-2-yl)-3-(trifluoromethyl)-1H-pyrazole: 1.1 g (53%); TLC system: EtOAc-PE; 1:1; Rf: 0.52

[trans-rac] 1-(2-Methoxyethyl)-5-(4-methyl-4-((3-(trifluoromethyl)phenyl)sulfonyl)tetrahydro-2H-pyran-2-yl)-3-(trifluoromethyl)-1H-pyrazole: 80 mg; TLC system: EtOAc-PE; 1:1; Rf: 0.52

Step 8: [cis-rac] 2-[5-[4-Methyl-4-[[3-(trifluoromethyl)phenyl]sulfonyl]-tetrahydro-pyran-2-yl]-3-(trifluoromethyl)-1H-pyrazol-1-yl]-ethanol (Example 2)

To a solution of [cis-rac] 1-(2-methoxyethyl)-5-(4-methyl-4-((3-(trifluoromethyl)phenyl)-sulfonyl)tetrahydro-2H-pyran-2-yl)-3-(trifluoromethyl)-1H-pyrazole (1.1 g, 2.2 mmol, 1 eq) in DCM (20 ml), was added BCl$_3$ (1 M in DCM, 6.6 ml, 6.6 mmol, 3 eq) at 0° C. and the RM was stirred at RT for 16 h. After completion of the reaction, it was quenched with ice-water and extracted with DCM (3×80 ml). The organics were washed with water (80 ml) and brine (80 ml), dried (Na$_2$SO$_4$) and concentrated to give the crude product which upon flash chromatography (silica gel; EtOAc-PE; 0:100→60:40) afforded the title compound (700 mg, 66%). TLC system: EtOAc-PE; 2:1; Rf: 0.31. NOE: On irradiating OCH proton NOE was observed with SCCH$_3$ as well as NCH$_2$.

[Cis-rac] 2-[5-[4-methyl-4-[[3-(trifluoromethyl)phenyl]sulfonyl]-tetrahydro-pyran-2-yl]-3-(trifluoromethyl)-1H-pyrazol-1-yl]-ethanol was subjected to chiral prep-SFC purification to give 180 mg of [cis-EN1] Example 2 and 160 mg of [cis-EN2] Example 2.

[cis-EN1] Example 2—analytical HPLC: Chiralcel OJH (250×4.6 mm 5 μm), 1 ml/min, n-hexane:IPA, 7:3, Ret. Time 7.256 min; m/z=487.0 [M+H]$^+$

[cis-EN2] Example 2—analytical HPLC: Chiralcel OJH (250×4.6 mm 5 μm), 1 ml/min, n-hexane:IPA, 7:3, Ret. Time 10.379 min; m/z=487.0 [M+H]$^+$

[trans-rac] 2-[5-[4-Methyl-4-[[3-(trifluoromethyl)phenyl]sulfonyl]-tetrahydro-pyran-2-yl]-3-(trifluoromethyl)-1H-pyrazol-1-yl]-ethanol (Example 2)

The corresponding [trans rac] isomer was prepared in analogy to step 8 starting from [trans-rac] 1-(2-methoxyethyl)-5-(4-methyl-4-((3-(trifluoromethyl)phenyl)sulfonyl)tetrahydro-2H-pyran-2-yl)-3-(trifluoromethyl)-1H-pyrazole (80 mg, see step 7).

[trans-rac] Example 2—m/z=487.0 [M+H]$^+$; TLC system: EtOAc-PE; 2:1; Rf: 0.35

1-(2-Methoxyethyl)-5-(4-methyl-4-((3-(trifluoromethyl)phenyl)sulfonyl)tetrahydro-2H-pyran-2-yl)-3-(methylsulfonyl)-1H-pyrazole (Example 23) and 2-[3-Methylsulfonyl-5-[4-methyl-4-[[3-(trifluoromethyl)phenyl]sulfonyl]-tetrahydro-pyran-2-yl]-1H-pyrazol-1-yl]-ethanol (Example 4)

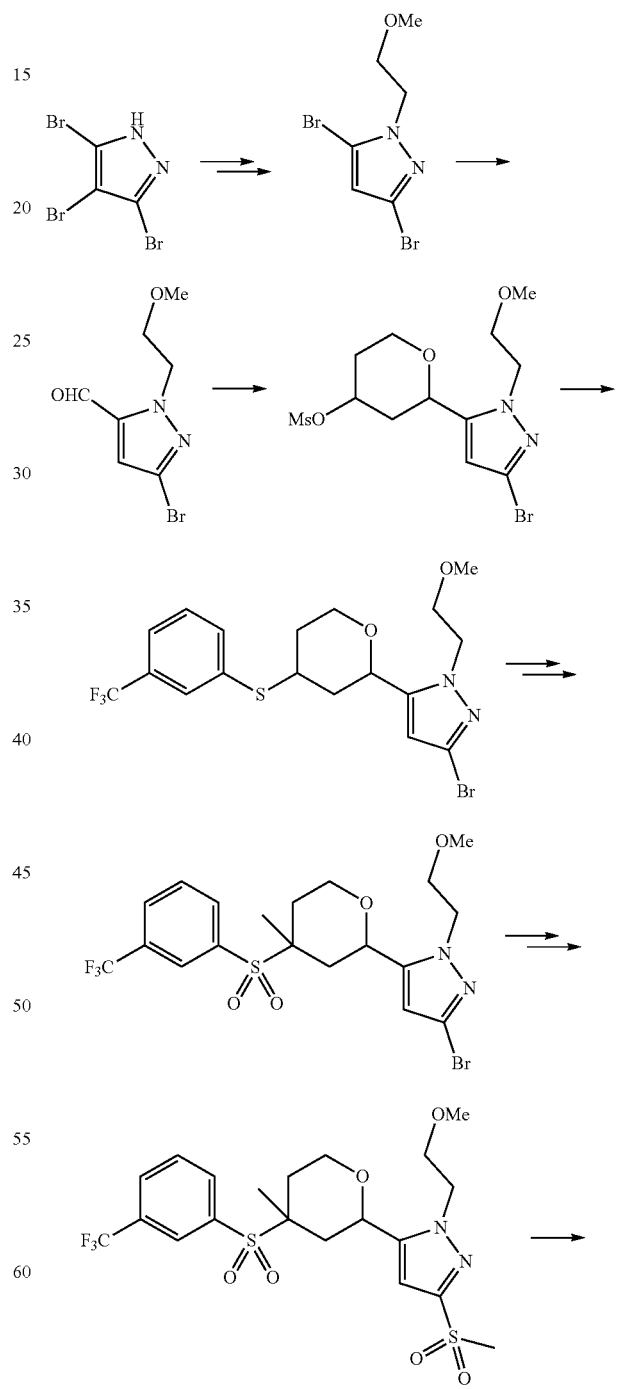

23

-continued

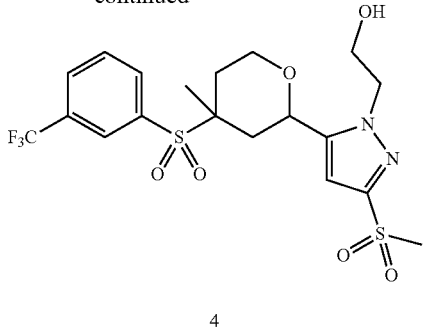

4

Step 1: 3,5-Dibromo-1H-pyrazole

To a solution of 3,4,5-tribromo-1H-pyrazole (25 g, 82 mmol, 1.0 eq) in THF (300 ml), was added n-BuLi (2.5 M in hexanes, 82.0 ml, 205 mmol, 2.5 eq) over 30 min at −78° C. and the RM was stirred at this temperature for 1.5 h. The RM was quenched by dropwise addition of MeOH-THF (2:3; 150 ml) at −78° C., stirred for an additional 2 h gradually allowing it to warm to RT. Then, the solvent was removed under reduced pressure. The residue was diluted with diethyl ether (600 ml), washed with dil. HCl (0.5 N, 60 ml) and brine (75 ml), dried ($Na_2SO_4$), filtered and concentrated under reduced pressure to afford the title compound (18 g).

Step 2: 3,5-Dibromo-1-(2-methoxyethyl)-1H-pyrazole

To a solution of 3,5-dibromo-1H-pyrazole (36 g, 161.4 mmol, 1.0 eq) in DMF (300 ml), was added $K_2CO_3$ (66 g, 478 mmol, 3.0 eq) followed by 1-bromo-2-methoxyethane (33 g, 239 mmol, 1.5 eq) at 0° C. The mixture was then allowed to warm to RT and stirred for 16 h. The RM was quenched with cold water (500 ml), diluted with EtOAc (1 l), and washed with water (3×500 ml) and brine (200 ml). The organics were dried ($Na_2SO_4$), filtered and concentrated under reduced pressure to afford the title compound (35 g).

Step 3: 3-Bromo-1-(2-methoxyethyl)-1H-pyrazole-5-carbaldehyde

A stirred solution of 3,5-dibromo-1-(2-methoxyethyl)-1H-pyrazole (25 g, 88.9 mmol, 1.0 eq) in THF (300 ml) was treated with iPrMgCl (2.0 M in THF, 89 ml, 177 mmol, 2 eq) at −78° C. The mixture was stirred for 30 min, then DMF (21 ml, 266.7 mmol, 3.0 eq) was added and the RM gradually allowed to RT and stirred for 5 h. The RM was quenched with aqueous $NH_4Cl$ (300 ml) and extracted with EtOAc (3×300 ml). The combined organic layers were washed with water (2×500 ml) and brine (150 ml), dried ($Na_2SO_4$), filtered and concentrated under reduced pressure to afford the title compound (22.5 g).

Step 4: 2-(3-Bromo-1-(2-methoxyethyl)-1H-pyrazol-5-yl)tetrahydro-2H-pyran-4-yl methanesulfonate A stirred solution of 3-bromo-1-(2-methoxyethyl)-1H-pyrazole-5-carbaldehyde (22.5 g, 96.566 mmol, 1.0 eq) in DCM (300 ml) was treated with MsOH (60 ml, 965.6 mmol, 10.0 eq) at 0° C. The mixture was stirred for 10 min and then but-3-en-1-ol (8 ml, 96.566 mmol, 1.0 eq) was added. The RM was allowed to warm to RT and stirred for 16 h. The RM was quenched with sat. aq. $Na_2CO_3$ (150 ml) and extracted with DCM (2×500 ml). The combined organic layers were washed with water (2×500 ml) and brine (200 ml), dried ($Na_2SO_4$), filtered and concentrated under reduced pressure to afford the title compound (19 g).

Step 5: 3-Bromo-1-(2-methoxyethyl)-5-(4-((3-(trifluoromethyl)phenyl)thio)tetrahydro-2H-pyran-2-yl)-1H-pyrazole A stirred solution of 2-(3-bromo-1-(2-methoxyethyl)-1H-pyrazol-5-yl)tetrahydro-2H-pyran-4-yl methanesulfonate (12.8 g, 71.9 mmol, 2.5 eq) in DMF (250 ml) was treated with $K_2CO_3$ (12 g, 86.38 mmol, 3 eq), stirred for 10 min at RT and then a solution of 3-(trifluoromethyl)benzenethiol (11 g, 28.79 mmol, 1.0 eq) in DMF (150 ml) was added. The resulting RM was heated to 50° C., stirred for 6 h, then brought to RT and stirred for additional 10 h. The RM was quenched with water (500 ml), extracted with EtOAc (3×300 ml). The combined organic layers were washed with water (3×300 ml) and brine (300 ml), dried ($Na_2SO_4$) filtered and concentrated under reduced pressure. The crude compound upon purification by flash chromatography (silica-gel; EtOAc-PE; 20:80→40:60) afforded the title compound (10 g).

Step 6: 3-Bromo-1-(2-methoxyethyl)-5-(4-((3-(trifluoromethyl)phenyl)sulfonyl)tetrahydro-2H-pyran-2-yl)-1H-pyrazole To a stirred solution of 3-bromo-1-(2-methoxyethyl)-5-(4-((3-(trifluoromethyl)phenyl)thio)tetrahydro-2H-pyran-2-yl)-1H-pyrazole (10 g, 21.55 mmol, 1.0 eq) in MeOH (100 ml) and water (50 ml), was added Oxone (33 g, 107.7 mmol, 5.0 eq) at RT and the mixture was stirred for 18 h. The RM was basified with sat. aq. $NaHCO_3$ (200 ml) and extracted with DCM (3×150 ml). The organic layer was washed with water (1×300 ml) and brine (200 ml), dried ($Na_2SO_4$), filtered and concentrated under reduced pressure to afford the title compound (11 g).

Step 7: [cis-rac] 3-Bromo-1-(2-methoxyethyl)-5-(4-methyl-4-((3-(trifluoromethyl)phenyl)sulfonyl)tetrahydro-2H-pyran-2-yl)-1H-pyrazole A stirred solution of 3-bromo-1-(2-methoxyethyl)-5-(4-((3-(trifluoromethyl)phenyl)sulfonyl)tetrahydro-2H-pyran-2-yl)-1H-pyrazole (11 g, 22.1 mmol, 1.0 eq) in THF (200 ml) was cooled to −78° C. KOtBu (1 M in THF, 44.3 ml, 44.3 mmol, 2.0 eq) was added dropwise. The mixture was stirred for 30 min, then MeI (3.57 ml, 55.25 mmol, 2.5 eq) was added. The resulting mixture was allowed to warm to RT and stirred for 18 h. The RM was quenched with sat.aq. $NH_4Cl$ (200 ml) and water (200 ml), and extracted with EtOAc (3×300 ml). The combined organic layers were washed with water (2×300 ml) and brine (300 ml), dried ($Na_2SO_4$), filtered and concentrated under reduced pressure. The residue upon purification by flash chromatography (silica gel; EtOAc-PE; 30:70→50:50) afforded the title compound (3 g, 8.5% overall yield for 7 steps). TLC system: EtOAc-PE; 1:1; Rf: 0.31.

Step 8: [cis-rac] 1-(2-Methoxyethyl)-5-(4-methyl-4-((3-(trifluoromethyl)phenyl)sulfonyl)tetrahydro-2H-pyran-2-yl)-3-(methylthio)-1H-pyrazole A stirred solution of [cis-rac]_3-bromo-1-(2-methoxyethyl)-5-(4-methyl-4-((3-(trifluoromethyl)phenyl)sulfonyl)

tetrahydro-2H-pyran-2-yl)-1H-pyrazole (0.2 g, 0.392 mmol, 1.0 eq), DIPEA (0.2 ml, 1.176 mmol, 3.0 eq) and sodium thiomethoxide (0.055 g, 0.784 mmol, 2 eq) in toluene (20 ml) was degassed for 10 min. Then, Xantphos (0.022 g, 0.0392 mmol, 0.1 eq) followed by Pd$_2$(dba)$_3$ (0.025 g, 0.027 mmol, 0.07 eq) and the mixture degassed again for 5 min. The resulting mixture was heated to 110° C. and stirred for 16 h under Ar. The RM was diluted with water (25 ml) and extracted with EtOAc (2×20 ml). The combined organic extracts were washed with water (2×20 ml and brine (25 ml), dried (Na$_2$SO$_4$) and concentrated under reduced pressure. The crude residue upon purification by flash chromatography (silica gel; EtOAc in PE; 30:70→50:50) afforded the title compound (0.08 g, 42%). In another batch [cis-rac] 3-bromo-1-(2-methoxyethyl)-5-(4-methyl-4-((3-(trifluoromethyl)phenyl)sulfonyl)tetrahydro-2H-pyran-2-yl)-1H-pyrazole (3 g) was transformed to the title compound (1 g, 35%).

Step 9: [cis-rac] 1-(2-Methoxyethyl)-5-(4-methyl-4-((3-(trifluoromethyl)phenyl)sulfonyl)tetrahydro-2H-pyran-2-yl)-3-(methylsulfonyl)-1H-pyrazole (Example 23)

To a stirred solution of [cis-rac] 1-(2-methoxyethyl)-5-(4-methyl-4-((3-(trifluoromethyl)phenyl)sulfonyl)tetrahydro-2H-pyran-2-yl)-3-(methylthio)-1H-pyrazole (1 g, 2.09 mmol, 1.0 eq) in MeOH (20 ml) and water (10 ml), was added Oxone (3.211 g, 10.46 mmol, 5.0 eq) at RT and the RM was stirred for 18 h. The RM was basified with sat. aq. NaHCO$_3$ (100 ml) and extracted with DCM (2×150 ml). The organic layer was washed with water (100 ml) and brine (100 ml), dried (Na$_2$SO$_4$), filtered and concentrated under reduced pressure to afford the title compound (0.78 g, 73%). TLC system: EtOAc-PE; 1:1; Rf: 0.25, m/z=511.0 [M+H]$^+$ Step 10: [cis-rac] 2-[3-Methyl sulfonyl-5-[4-methyl-4-[[3-(trifluoromethyl)phenyl]sulfonyl]-tetrahydropyran-2-yl]-1H-pyrazol-1-yl]-ethanol (Example 4)

To a stirred solution of [cis-rac] 1-(2-methoxyethyl)-5-(4-methyl-4-((3-(trifluoromethyl)phenyl)-sulfonyl)tetrahydro-2H-pyran-2-yl)-3-(methylsulfonyl)-1H-pyrazole (0.78 g, 1.52 mmol, 1.0 eq) in DCM (20 ml), 1 M BCl$_3$ in DCM (4.5 ml, 4.5 mmol, 3.0 eq) was added at 0° C. and the mixture was allowed to warm to RT and stirred for 16 h. The reaction was quenched with ice water (30 ml) and extracted with DCM (2×50 ml. The combined organic layers were washed with water (60 ml), brine (60 ml), dried (Na$_2$SO$_4$) and concentrated under reduced pressure to afford a residue, which upon purification by flash chromatography (silica gel; EtOAc in PE; 90:10→100:00) afforded the title compound (0.4 g, 52%). TLC system: EtOAc-PE; 7:3; Rf: 0.35

[Cis-rac] 2-[3-methyl sulfonyl-5-[4-methyl-4-[[3-(trifluoromethyl)phenyl]sulfonyl]-tetrahydro-pyran-2-yl]-1H-pyrazol-1-yl]-ethanol was subjected to chiral prep-SFC purification to give 90 mg of [cis-EN1] Example 4 and 100 mg of [cis-EN2] Example 4.

[cis-EN1] Example 4—analytical SFC: Chiralpak AD-H (250×4.6 mm 5 μm) 30.22° C., 3 g/min, 100 bar, 20% MeOH, Ret. Time 2.33 min; m/z=497.0 [M+H]$^+$

[cis-EN2] Example 4—analytical SFC: Chiralpak AD-H (250×4.6 mm 5 μm) 30.22° C., 3 g/min, 100 bar, 20% MeOH, Ret. Time 3.57 min; m/z=497.0 [M+H]$^+$ 3-(Difluoromethyl)-1-(methoxymethyl)-5-(4-methyl-4-((3-(trifluoromethyl)phenyl)sulfonyl)tetrahydro-2H-pyran-2-yl)-1H-pyrazole (Example 5)

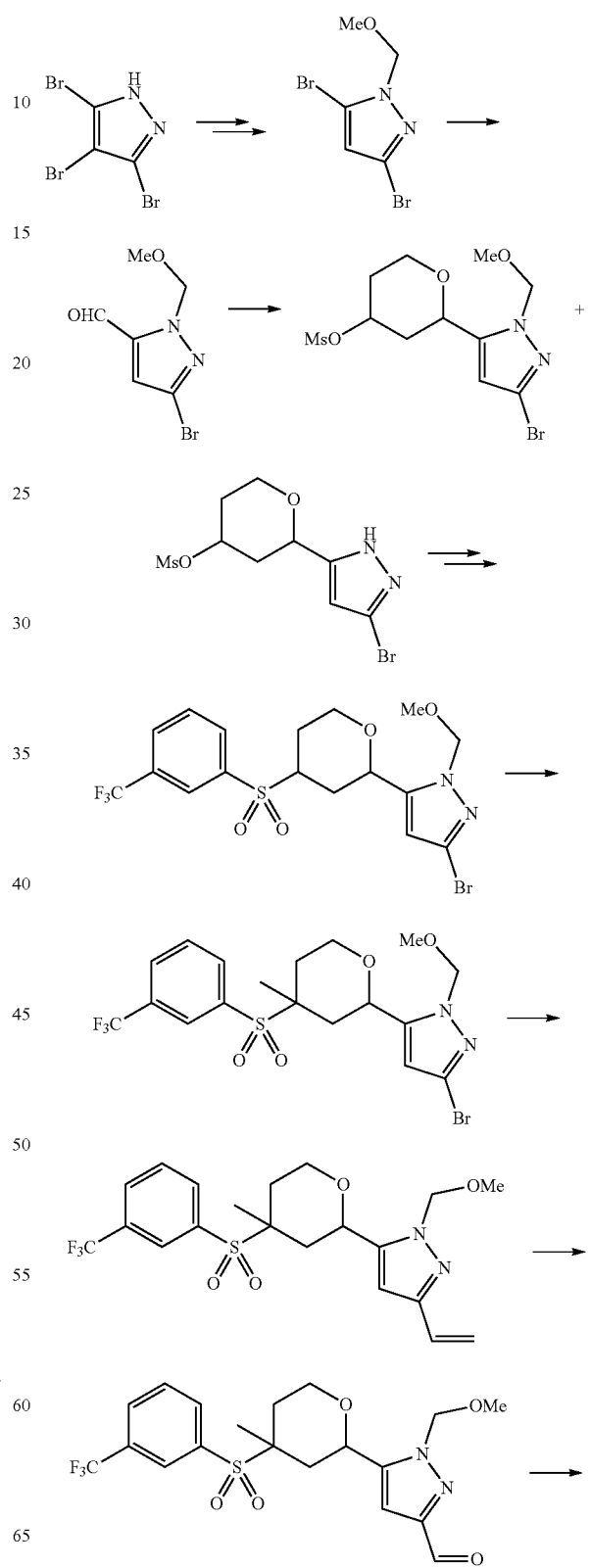

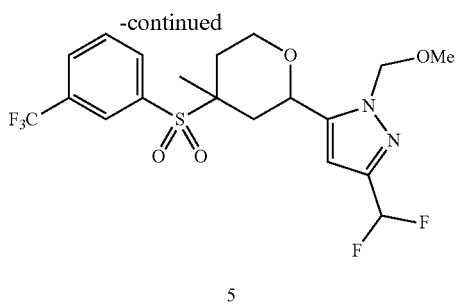

5

Step 1: 3,5-Dibromo-1-(methoxymethyl)-1H-pyrazole

A solution of 3,5-dibromo-1H-pyrazole (25 g, 111.70 mmol, 1.0 eq) in THF (200 ml) was added to a suspension of NaH (60%; 5.89 g, 245 mmol, 2.2 eq) in THF (100 ml) at 0° C. The mixture was stirred for 1 h before chloromethyl methyl ether (13.57 ml, 167.5 mmol, 1.5 eq) was added. The RM was stirred at 0° C. for 2 h and then allowed to warm to RT and stirred for 12 h. The mixture was quenched with cold water (500 ml), and extracted with EtOAc (3×200 ml). The combined organic layers were washed with water (2×200 ml) and brine (200 ml), dried (Na$_2$SO$_4$), filtered and concentrated under reduced pressure to afford the title compound (15 g, 51%).

Step 2: 3-Bromo-1-(methoxymethyl)-1H-pyrazole-5-carbaldehyde

A stirred solution of 3,5-dibromo-1-(methoxymethyl)-1H-pyrazole (15 g, 56.01 mmol, 1.0 eq) in THF (150 ml) was treated with iPrMgCl (1.0 M, 67.2 ml, 67.2 mmol, 1.2 eq) at −78° C. The mixture was stirred for 30 min, before adding DMF (30.9 ml, 397 mmol, 7.0 eq) and gradually allowing it to warm to RT and stir for 14 h. The RM was quenched with aq NH$_4$Cl (300 ml) and extracted with EtOAc (3×150 ml). The combined organic layer was washed with water (2×150 ml) and brine (150 ml), dried (Na$_2$SO$_4$), filtered and concentrated under reduced pressure to afford the title compound (16.0 g).

Step 3: 2-(3-Bromo-1-(methoxymethyl)-1H-pyrazol-5-yl)tetrahydro-2H-pyran-4-yl methanesulfonate and 2-(3-Bromo-1H-pyrazol-5-yl)tetrahydro-2H-pyran-4-yl methanesulfonate A stirred solution of 3-bromo-1-(methoxymethyl)-1H-pyrazole-5-carbaldehyde (16.0 g, crude, 58.5 mmol, 1.0 eq) in DCM (250 ml) was treated with MsOH (36.4 ml, 585.1 mmol, 10.0 eq) at 0° C. The mixture was stirred for 10 min and but-3-en-1-ol (4.8 ml, 58.5 mmol, 1.0 eq) was added. The RM was allowed to warm to RT and stirred for 18 h. The RM was quenched with sat. aq. Na$_2$CO$_3$ (150 ml) and extracted with DCM (2×200 ml). The combined organic layers were washed with water (2×150 ml) and brine (150 ml), dried (Na$_2$SO$_4$), filtered and concentrated under reduced pressure to afford the title compounds (18 g).

Step 4: 3-Bromo-5-(4-((3-(trifluoromethyl)phenyl)thio)tetrahydro-2H-pyran-2-yl)-1H-pyrazole and 3-Bromo-1-(methoxymethyl)-5-(4-((3-(trifluoromethyl)phenyl)thio)tetrahydro-2H-pyran-2-yl)-1H-pyrazole A stirred solution of 3-(trifluoromethyl)benzenethiol (17.3 g, 97.56 mmol, 2.0 eq) in DMF (250 ml) was treated with K$_2$CO$_3$ (20.19 g, 146.3 mmol, 3.0 eq), stirred for 10 minutes at RT. A solution of 2-(3-bromo-1-(methoxymethyl)-1H-pyrazol-5-yl)tetrahydro-2H-pyran-4-yl methanesulfonate and 2-(3-bromo-1H-pyrazol-5-yl)tetrahydro-2H-pyran-4-yl methanesulfonate (18 g, 48.78 mmol, 1.0 eq) in DMF (150 ml) was added. The resulting RM was heated to 50° C., stirred for 6 h, then brought to RT and stirred for additional 10 h. The RM was concentrated under reduced pressure and the residue was diluted with water (500 ml) and extracted with EtOAc (3×200 ml). The combined organic layers were washed with water (2×200 ml) and brine (200 ml), dried (Na$_2$SO$_4$) filtered and concentrated under reduced pressure. The crude compound upon purification by flash chromatography (silica-gel; EtOAc-PE; 20:80→30:70) afforded the title compounds (9 g, 2 g, over 3 steps).

Note: 3-Bromo-5-(4-((3-(trifluoromethyl)phenyl)thio)tetrahydro-2H-pyran-2-yl)-1H-pyrazole was converted to 3-bromo-1-(methoxymethyl)-5-(4-((3-(trifluoromethyl)phenyl)thio)tetrahydro-2H-pyran-2-yl)-1H-pyrazole (10 g, 60%) employing the method described in step 1.

Step 5: 3-Bromo-1-(methoxymethyl)-5-(4-((3-(trifluoromethyl)phenyl)sulfonyl)tetrahydro-2H-pyran-2-yl)-1H-pyrazole Oxone (27.2 g, 88.8 mmol, 5.0 eq) in water (50 ml,) was added to a solution of 3-bromo-1-(methoxymethyl)-5-(4-((3-(trifluoromethyl)phenyl)thio)tetrahydro-2H-pyran-2-yl)-1H-pyrazole (8 g, 17.7 mmol, 1.0 eq) in MeOH (150 ml) at RT and the mixture was stirred for 18 h. After completion of the reaction, MeOH was distilled off under reduced pressure. The residue was made alkaline by addition of sat. aq. NaHCO$_3$ (200 ml) and extracted with EtOAc (3×150 ml). The organic layer was washed with water (2×150 ml) and brine (100 ml), dried (Na$_2$SO$_4$), filtered and concentrated under reduced pressure. The crude residue upon purification by flash chromatography (silica-gel; EtOAc-PE; 10:90→30:70) afforded the title compound (6.5 g, 76%).

Step 6: 3-Bromo-1-(methoxymethyl)-5-(4-methyl-4-((3-(trifluoromethyl)phenyl)sulfonyl)tetrahydro-2H-pyran-2-yl)-1H-pyrazole A solution of 3-bromo-1-(methoxymethyl)-5-(4-((3-(trifluoromethyl)phenyl)sulfonyl)tetrahydro-2H-pyran-2-yl)-1H-pyrazole (6.5 g, 13.48 mmol 1.0 eq) in THF (100 ml) was cooled to −78° C. and KOtBu (1M in THF, 26.9 ml, 26.9 mmol, 2.0 eq) was added dropwise. The mixture was stirred for 30 min and MeI (2.0 ml, 33.7 mmol, 2.5 eq) was added. The resulting RM was allowed to RT and stir for 18 h. It was then quenched with sat. aq. NH$_4$Cl (200 ml) and water (200 ml), and extracted with EtOAc (3×200 ml). The combined organic layers were washed with water (2×200 ml) and brine (200 ml), dried (Na$_2$SO$_4$), filtered and concentrated under reduced pressure. The residue upon purification flash chromatography (silica gel; EtOAc-PE; 15:85→30:70) afforded the title cis and trans racemates.

[cis-rac] 3-Bromo-1-(methoxymethyl)-5-(4-methyl-4-((3-(trifluoromethyl)phenyl)sulfonyl)tetrahydro-2H-pyran-2-yl)-1H-pyrazole: 3.5 g (52%); TLC system: EtOAc-PE; 1:1; Rf: 0.50

[trans-rac] 3-Bromo-1-(methoxymethyl)-5-(4-methyl-4-((3-(trifluoromethyl)phenyl)sulfonyl)tetrahydro-2H-pyran-2-yl)-1H-pyrazole: 1.5 g; TLC system: EtOAc-PE; 1:1; Rf: 0.60.

Step 7: [cis-rac] 1-(Methoxymethyl)-5-(4-methyl-4-((3-(trifluoromethyl)phenyl)sulfonyl)tetrahydro-2H-pyran-2-yl)-3-vinyl-1H-pyrazole A stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole (3.5 g, 7.05 mmol, 1.0 eq), potassium vinyl trifluoroborate (3.7 g, 28.22 mmol, 4.0 eq) and $Cs_2CO_3$ (6.89 g, 21.15 mmol, 3.0 eq) in DMF-$H_2O$ (150 ml & 20 ml) was degassed for 20 minutes with Ar. Then $PdCl_2(dppf)_2$.DCM (575 mg, 0.705 mmol, 0.1 eq) was added and the mixture degassed for 10 min. The resulting RM was heated to 120° C. and stirred for 16 h. The RM was concentrated under reduced pressure, and the residue was diluted with water (150 ml) and extracted with EtOAc (2×150 ml). The combined organic extract was washed with water (2×100 ml) and brine (100 ml), dried ($Na_2SO_4$) and concentrated under reduced pressure. The residue upon purification by flash chromatography (silica gel, EtOAc:PE; 30:70→60:40) afforded the title compound (2.5 g, 80%).

Step 8: [cis-rac] 1-(Methoxymethyl)-5-(4-methyl-((3-(trifluoromethyl)phenyl)sulfonyl)tetrahydro-2H-pyran-2-yl)-1H-pyrazole-3-carbaldehyde Ozone gas was bubbled through a solution of [cis-rac] 1-methoxymethyl)-5-(4-methyl-4-((3-(trifluoromethyl)phenyl)sulfonyl)tetrahydro-2H-pyran-2-yl)-3-vinyl-1H-pyrazole (2.5 g, 6.03 mmol, 1.0 eq) in acetone-$H_2O$ (60 ml & 4 ml) at −20 to 0° C. for 30 min. The RM was diluted with water (100 ml), and extracted with EtOAc (3×70 ml). The combined organic layers were washed with water (2×100 ml) and brine (100 ml), dried over anhydrous $Na_2SO_4$, filtered and concentrated under reduced pressure to afford the title compound (1.5 g).

Step 9: [cis-rac] 3-(Difluoromethyl)-1-(methoxymethyl)-5-(4-methyl-4-((3-(trifluoromethyl)phenyl)sulfonyl)tetrahydro-2H-pyran-2-yl)-1H-pyrazole (Example 5)

A stirred solution of [cis-rac] 1-(methoxymethyl)-5-(4-methyl-4-((3-(trifluoromethyl)phenyl)-sulfonyl)tetrahydro-2H-pyran-2-yl)-1H-pyrazole-3-carbaldehyde (1.5 g, 3.36 mmol, 1.0 eq), in DCM (25 ml) was cooled to −78° C. and treated with DAST (1.7 ml, 13.4 mml, 4.0 eq). The resulting RM was allowed to warm to RT and stirred for 16 h. The mixture was cooled to 0°, quenched with sat. aq. $NaHCO_3$ (30 ml) and extracted with EtOAc (2×20 ml). The combined organic layers were washed with water (2×20 ml) and brine (75 ml), dried over anhydrous $Na_2SO_4$, filtered and concentrated under reduced pressure. The residue upon purification by flash chromatography silica gel, EtOAc-PE; 30:70→60:40), afforded the title compound (700 mg, 30% over 2 steps).

[trans-rac] 3-(Difluoromethyl)-1-(methoxymethyl)-5-(4-methyl-4-((3-(trifluoromethyl)phenyl)-sulfonyl)tetrahydro-2H-pyran-2-yl)-1H-pyrazole (Example 5)

The corresponding [trans rac] 1-methoxymethyl)-5-(4-methyl-4-((3-(trifluoromethyl)phenyl)sulfonyl)tetrahydro-2H-pyran-2-yl)-3-vinyl-1H-pyrazole isomer was prepared in analogy to step 7 starting from [trans rac] 3-bromo-1-(methoxymethyl)-5-(4-methyl-4-((3-(trifluoromethyl)phenyl)sulfonyl)tetrahydro-2H-pyran-2-yl)-1H-pyrazole (1.5 g, see step 6).

The corresponding [trans rac] isomer of example 5 was prepared in analogy to steps 8 & 9 starting from [trans rac] 1-methoxymethyl)-5-(4-methyl-4-((3-(trifluoromethyl)phenyl)sulfonyl)tetrahydro-2H-pyran-2-yl)-3-vinyl-1H-pyrazole (see step 7).

3-[5-[4-Methyl-4-[[3-(trifluoromethyl)phenyl]sulfonyl]-tetrahydro-pyran-2-yl]-3-(trifluoromethyl)-1H-pyrazol-1-yl]-propan-1-ol (Example 9)

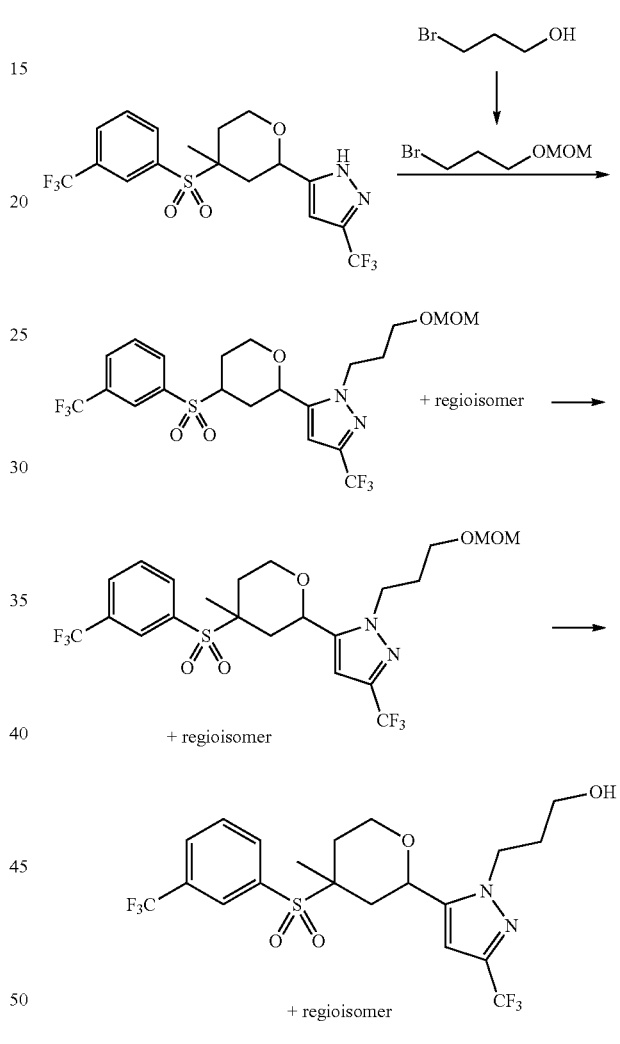

9

Step 1: 1-Bromo-3-(methoxymethoxy)propane

To a solution of 3-bromopropan-1-ol (2.0 g, 14.39 mmol, 1 eq) in DCM (60 ml) was added DIPEA (10.2 ml, 57.55 mmol, 4 eq), and chloromethyl methyl ether (5.5 ml, 71.94 mmol, 5.0 eq) at 0° C. The RM was stirred at RT for 2 h, quenched with 1 N HCl (30 ml) and extracted with DCM (3×40 ml). The combined organic layers were washed with sat. aq. $NaHCO_3$ (50 ml), water (50 ml) and brine (40 ml), dried ($Na_2SO_4$) and concentrated under reduced pressure to afford the title compound (1.8 g, 69%).

Step 2: 1-(3-(Methoxymethoxy)propyl)-3-(trifluoromethyl)-5-(4-((3-(trifluoromethyl)phenyl)sulfonyl)tetrahydro-2H-pyran-2-yl)-1H-pyrazole and 1-(3-(Methoxymethoxy)propyl)-5-(trifluoromethyl)-3-(4-((3-(trifluoro-methyl)phenyl)sulfonyl)tetrahydro-2H-pyran-2-yl)-1H-pyrazole To a solution of 3-(trifluoromethyl)-5-(4-((3-(trifluoromethyl)phenyl)sulfonyl)tetrahydro-2H-pyran-2-yl)-1H-pyrazole [step 5 product, Example 19] (1.5 g, 3.50 mmol, 1 eq) in MeCN (50 ml) was added $K_2CO_3$ (1.4 g, 10.51 mmol, 3 eq) and 1-bromo-3-(methoxymethoxy)propane (1.2 g, 7.1 mmol, 2 eq) at 0° C. The RM was stirred at RT for 16 h, quenched with cold water (80 ml) and extracted with EtOAc (3×40 ml). The combined organic extracts were washed with water (2×50 ml) and brine (50 ml), dried ($Na_2SO_4$) and concentrated under reduced pressure. The crude residue upon purification by flash chromatography (silica gel; EtOAc-PE; 20:80→50:50) afforded a mixture of 1-(3-methoxymethoxy)propyl)-3-(trifluoromethyl)-5-(4-((3-(trifluoromethyl)phenyl)sulfonyl)tetrahydro-2H-pyran-2-yl)-1H-pyrazole and 1-(3-(methoxymethoxy)propyl)-5-(trifluoromethyl)-3-(4-((3-(trifluoromethyl)phenyl)-sulfonyl)tetrahydro-2H-pyran-2-yl)-1H-pyrazole (1.0 g, 54%).

Step 3: 1-(3-(Methoxymethoxy)propyl)-5-(4-methyl-4-((3-(trifluoromethyl)phenyl)sulfonyl)tetrahydro-2H-pyran-2-yl)-3-(trifluoromethyl)-1H-pyrazole and 1-(3-Methoxymethoxy)propyl)-3-(4-methyl-4-((3-(trifluoromethyl)phenyl)sulfonyl)tetrahydro-2H-pyran-2-yl)-5-(trifluoromethyl)-1H-pyrazole To a solution of a mixture of 1-(3-methoxymethoxy)propyl)-3-(trifluoromethyl)-5-(4-((3-(trifluoromethyl)phenyl)sulfonyl)tetrahydro-2H-pyran-2-yl)-1H-pyrazole and 1-(3-(methoxymethoxy)propyl)-5-(trifluoromethyl)-3-(4-((3-(trifluoromethyl)phenyl)sulfonyl)tetrahydro-2H-pyran-2-yl)-1H-pyrazole (1.0 g, 1.88 mmol, 1 eq) in THF (40 ml), cooled to −78° C., was added dropwise KOtBu (1 M solution in THF, 4.0 ml, 3.8 mmol, 2.0 eq). The RM was stirred for 30 min, then methyl iodide (0.3 ml, 4.7 mmol, 2.5 eq) was added. The resulting mixture was allowed to warm to RT and stirred for 16 h. The RM was quenched with aq. $NH_4Cl$ (15 ml) and water (45 ml) and extracted with EtOAc (3×50 ml). The combined organic extracts were washed with water (60 ml) and brine (50 ml), dried ($Na_2SO_4$) and concentrated under reduced pressure to afford a mixture of 1-(3-(methoxymethoxy)propyl)-5-(4-methyl-4-((3-(trifluoromethyl)phenyl)sulfonyl)tetrahydro-2H-pyran-2-yl)-3-(trifluoromethyl)-1H-pyrazole and 1-(3-methoxymethoxy)propyl)-3-(4-methyl-4-((3-(trifluoromethyl)phenyl)sulfonyl)tetrahydro-2H-pyran-2-yl)-5-(trifluoromethyl)-1H-pyrazole (1.0 g).

Step 4: [cis-rac] 3-[5-[4-Methyl-4-[[3-(trifluoromethyl)phenyl]sulfonyl]-tetrahydro-pyran-2-yl]-3-(trifluoromethyl)-1H-pyrazol-1-yl]-propan-1-ol (Example 9) and 3-(3-(4-methyl-4-((3-(trifluoromethyl)phenyl)sulfonyl)tetrahydro-2H-pyran-2-yl)-5-(trifluoromethyl)-1H-pyrazol-1-yl)propan-1-ol To a solution of a mixture of a mixture of 1-(3-(methoxymethoxy)propyl)-5-(4-methyl-4-((3-(trifluoromethyl)phenyl)sulfonyl)tetrahydro-2H-pyran-2-yl)-3-(trifluoromethyl)-1H-pyrazole and 1-(3-methoxymethoxy)propyl)-3-(4-methyl-4-((3-(trifluoromethyl)phenyl)sulfonyl)tetrahydro-2H-pyran-2-yl)-5-(trifluoromethyl)-1H-pyrazole (1.0 g, 1.83 mmol, 1 eq) in EtOH (15 ml), was added aq. HCl (4 M; 25 ml). The RM was warmed to 60° C. and stirred for 2 h. After completion of the reaction, it was quenched with sat. aq. $NaHCO_3$ (100 ml) at 0° C., and extracted with EtOAC (3×40 ml). The organics were washed with water (60 ml) and brine (60 ml), dried ($Na_2SO_4$) and concentrated under reduced pressure. The crude upon purification by flash chromatography (silica gel; EtOAc-PE; 20:80→80:20) afforded [cis-rac] 3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol (Example 9) (110 mg; 12%). TLC system: EtOAc-pet-ether; 3:2; Rf: 0.25. NOE: On irradiating $OCH$ proton NOE was observed with $SCCH_3$ as well as $NCH_2$ Also obtained was 3-(3-(4-methyl-4-((3-(trifluoromethyl)phenyl)sulfonyl)tetrahydro-2H-pyran-2-yl)-5-(trifluoromethyl)-1H-pyrazol-1-yl)propan-1-ol (90 mg; 10%).

[Cis-rac] 3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol was subjected to chiral prep-SFC purification to give 35 mg of [cis-EN1] Example 9 and 35 mg of [cis-EN2] Example 9.

[cis-EN1] Example 9—analytical SFC: Lux Amylose-2 (250×4.6 mm 5 μm) 30° C., 3 g/min, 100 bar, 15% IPA, Ret. Time 2.89 min; m/z=501.1 [M+H]+

[cis-EN2] Example 9—analytical SFC: Lux Amylose-2 (250×4.6 mm 5 μm) 30° C., 3 g/min, 100 bar, 15% IPA, Ret. Time 5.53 min; m/z=501.1 [M+H]+

1-(3-Methoxypropyl)-5-(4-methyl-4-((3-(trifluoromethyl)phenyl)sulfonyl)tetrahydro-2H-pyran-2-yl)-3-(trifluoromethyl)-1H-pyrazole (Example 10)

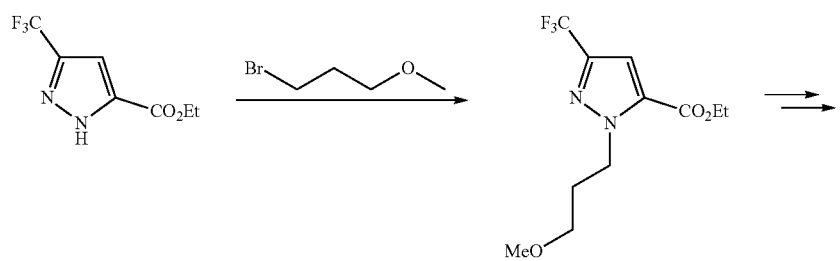

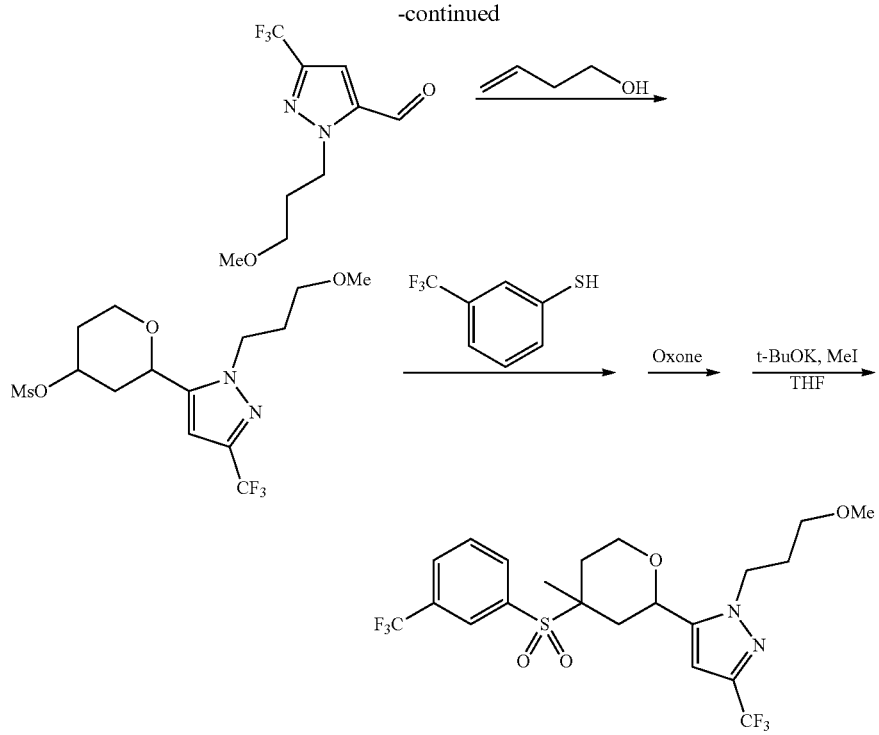

Step 1: Ethyl 1-(3-methoxypropyl)-3-(trifluoromethyl)-1H-pyrazole-5-carboxylate To a solution of ethyl 3-(trifluoromethyl)-1H-pyrazole-5-carboxylate (2.0 g, 9.615 mmol, 1 eq) in DMF (60 ml) was added $K_2CO_3$ (4.0 g, 28.845 mmol, 3 eq) and 1-bromo 3-methoxy propane (3.0 g, 19.230 mmol, 2 eq) at 0° C. The RM was stirred at RT for 16 h, quenched with cold water (40 ml) and extracted with EtOAc (3×40 ml). The combined organic layers were washed with water (2×40 ml) and brine (50 ml), dried ($Na_2SO_4$) and concentrated under reduced pressure. The residue upon purification by flash chromatography (silica gel; EtOAc-PE; 0:100→4:96) afforded the title compound (2.0 g, 74%).

Step 2: (1-(3-Methoxypropyl)-3-(trifluoromethyl)-1H-pyrazol-5-yl)methanol $LiAlH_4$ (1.0 M in THF; 21.505 ml, 21.505 mmol, 3 eq) was added dropwise to a solution of ethyl 1-(3-methoxypropyl)-3-(trifluoromethyl)-1H-pyrazole-5-carboxylate (2.0 g, 7.168 mmol, 1 eq) in THF (50 ml) at 0°. The RM was stirred at RT for 2 h. The RM was carefully quenched with saturated $NH_4Cl$ solution (100 ml) at 0° C. and filtered through Celite. The filtrate was extracted with EtOAc (3×50 ml). The combined organic layers were washed with water (100 ml) and brine (70 ml), dried ($Na_2SO_4$) and concentrated to afford the title compound (1.7 g).

Step 3: 1-(3-Methoxypropyl)-3-(trifluoromethyl)-1H-pyrazole-5-carbaldehyde

To a solution of (1-(3-methoxypropyl)-3-(trifluoromethyl)-1H-pyrazol-5-yl)methanol (1.7 g, 7.172 mmol, 1 eq) in 1,2-dichloroethane (60 ml), was added $MnO_2$ (1.87 g, 21.518 mmol, 3 eq) at RT. The RM was heated to 90° C. and stirred for 3 h. After completion of the reaction, the mixture was filtered through celite and the filtrate was concentrated under reduced pressure to afford the title compound (1.0 g, 61% over 2 steps).

Step 4: 2-(1-(3-Methoxypropyl)-3-(trifluoromethyl)-1H-pyrazol-5-yl)tetrahydro-2H-pyran-4-yl methanesulfonate To a solution of 1-(3-methoxypropyl)-3-(trifluoromethyl)-1H-pyrazole-5-carbaldehyde (1.0 g, 4.237 mmol, 1 eq) in DCM (30 ml) was added methane sulfonic acid (4.0 ml, 42.37 mmol, 10 eq) at 0° C., followed by 3-buten-1-ol (0.45 ml, 6.355 mmol, 1.5 eq). The RM was stirred at RT for 16 h. The mixture was quenched with a cold saturated solution of aq. $Na_2CO_3$ until pH~10, and extracted with DCM (3×30 ml). The combined organic extracts were washed with water (50 ml) and brine (40 ml), dried ($Na_2SO_4$) and upon concentration afforded the title compound.

Step 5: 1-(3-Methoxypropyl)-3-(trifluoromethyl)-5-(4-((3-(trifluoromethyl)phenyl)thio)tetrahydro-2H-pyran-2-yl)-1H-pyrazole To a solution of 3-(trifluoromethyl)benzenethiol (1.0 ml, 7.122 mmol, 2.5 eq) in DMF (20 ml), was added $K_2CO_3$ (1.17 g, 8.547 mmol, 3 eq) followed by 2-(1-(3-methoxypropyl)-3-(trifluoromethyl)-1H-pyrazol-5-yl)tetrahydro-2H-pyran-4-yl methanesulfonate (1.1 g, 2.849 mmol, 1 eq) in DMF (20 ml) and the RM was heated to 50° C. and stirred for 6 h and then for 10 h at RT. After completion of the reaction, the mixture was diluted with cold water (100 ml), extracted with EtOAc (3×35 ml), washed with water (60 ml)

and brine (40 ml), dried (Na₂SO₄) and concentrated under reduced pressure. The residue upon purification by flash chromatography (silica gel; EtOAc-PE; 5:95→20:80) afforded the title compound (700 mg, 35% over 2 steps).

Step 6: [cis-rac] 1-(3-Methoxypropyl)-3-(trifluoromethyl)-5-(4-((3-(trifluoromethyl)phenyl)sulfonyl)tetrahydro-2H-pyran-2-yl)-1H-pyrazole Oxone (2.3 g, 7.47 mmol, 5 eq) in water (15 ml) was added to a solution of 1-(3-methoxypropyl)-3-(trifluoromethyl)-5-(4-((3-(trifluoromethyl)phenyl)thio)tetrahydro-2H-pyran-2-yl)-1H-pyrazole (0.7 g, 1.495 mmol, 1 eq) in MeOH (45 ml) at RT and stirred for 16 h. After completion of the reaction, MeOH was distilled off under reduced pressure and the residue was diluted with water (30 ml) and sat. aq. NaHCO₃ (until pH~8-9). It was then extracted with EtOAc (3×20 ml), and the organics were washed with water (60 ml) and brine (40 ml), dried (Na₂SO₄) and concentrated to give the crude product, which upon flash chromatography (silica gel; EtOAc-PE; 10:90→35:65) afforded the title compound (0.5 g, 66%). TLC system: EtOAc-PE; 1:1; Rf: 0.37

Step 7: [cis-rac] 1-(3-Methoxypropyl)-5-(4-methyl-4-((3-(trifluoromethyl)phenyl)sulfonyl)tetrahydro-2H-pyran-2-yl)-3-(trifluoromethyl)-1H-pyrazole (Example 10)

To a solution of 1-(3-methoxypropyl)-3-(trifluoromethyl)-5-(4-((3-(trifluoromethyl)phenyl)sulfonyl)tetrahydro-2H-pyran-2-yl)-1H-pyrazole (0.5 g, 1.00 mmol, 1 eq) in THF (60 ml), cooled to −78° C., was added dropwise KOtBu (1 M solution in THF, 2.0 ml, 2.0 mmol, 2.0 eq), and the mixture was stirred for 30 min before methyl iodide (0.16 ml, 2.5 mmol, 2.5 eq) was added. The RM was allowed to warm to RT and stirred for 16 h. The mixture was quenched with water (20 ml) and extracted with EtOAc (3×20 ml). The combined organic layers were washed with water (60 ml) and brine (40 ml), dried (Na₂SO₄) and concentrated under reduced pressure. The residue upon purification by flash chromatography (silica gel; EtOAc-PE; 20:80→40:60) afforded the title compound (0.30 g, 58%). TLC system: EtOAc-PE; 1:1; Rf: 0.57; m/z=515.0 [M+H]⁺; regiochemistry confirmed by ¹³C NMR & 2D NMR experiments 2-[5-[4-Methyl-4-[[3-(trifluoromethyl)phenyl]sulfonyl]-tetrahydro-pyran-2-yl]-3-(trifluoromethyl)-1H-pyrazol-1-yl]-acetamide (Example 11)

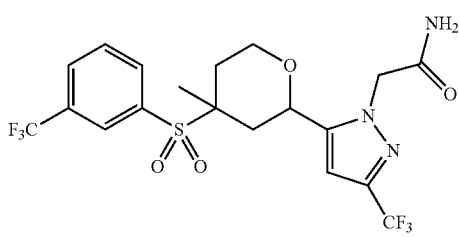 [SMILES: CC1(S(=O)(=O)c2cccc(C(F)(F)F)c2)CCOC(c2cc(C(F)(F)F)nn2CC(N)=O)C1]

Step 1: [cis-rac] 2-[5-[4-Methyl-4-[[3-(trifluoromethyl)phenyl]sulfonyl]-tetrahydro-pyran-2-yl]-3-(trifluoromethyl)-1H-pyrazol-1-yl]-acetamide (Example 11)

To a stirred solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8 product, Example 19] (270 mg, 0.61 mmol, 1 eq) in MeCN (10 ml), K₂CO₃ (252 mg, 1.83 mmol, 3 eq) and 2-bromoacetamide (100 mg, 0.73 mmol, 1.2 eq) were added at RT. The RM was stirred for 18 h at 80° C. The RM was cooled to RT and diluted with EtOAc (150 ml). The organics were washed with water (2×50 ml) and brine (50 ml), dried (Na₂SO₄), filtered and concentrated. The residue was triturated with 30% Et₂O-pentane. The crude product was further purified by reversed phase flash chromatography to afford the title compound (180 mg, 59%). TLC system: 80% EtOAc-PE; Rf: 0.31. NOE: On irradiating OCH proton NOE was observed with SCCH₃ as well as NCH₂

[Cis-rac] 2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide was subjected to chiral prep-SFC purification to give 38 mg of [cis-EN1] Example 11 and 39 mg of [cis-EN2] Example 11.

[cis-EN1] Example 11—analytical SFC: Lux Cellulose-2 (250×4.6 mm 5 µm) 30.2° C., 3 g/min, 100 bar, 20% IPA, Ret. Time 5.45 min; m/z=500.0 [M+H]⁺

[cis-EN2] Example 11—analytical SFC: Lux Cellulose-2 (250×4.6 mm 5 µm) 29.9° C., 3 g/min, 100 bar, 20% IPA, Ret. Time 6.52 min; m/z=500.0 [M+H]⁺

[1-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-cyclopropyl]-amine (Example 15)

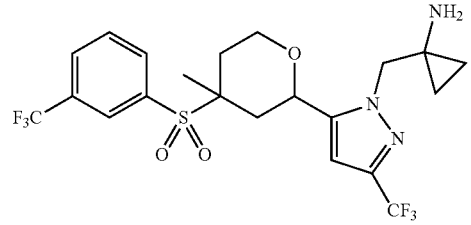 [SMILES: CC1(S(=O)(=O)c2cccc(C(F)(F)F)c2)CCOC(c2cc(C(F)(F)F)nn2CC2(N)CC2)C1]

Step 1: (1-((tert-Butoxycarbonyl)amino)cyclopropyl)methyl methanesulfonate

To a stirred solution of tert-butyl (1-(hydroxymethyl)cyclopropyl)carbamate (800 mg, 4.27 mmol, 1 eq) in DCM (20 ml), Et₃N (1.8 ml, 12.83 mmol, 3 eq) and MsCl (0.5 ml, 6.40 mmol, 1.5 eq) were added at 0° C. The RM was stirred for 2 h at RT. The RM diluted with DCM (150 ml), washed with water (2×50 ml) and brine (50 ml), dried (Na₂SO₄), filtered and concentrated to afford the title compound (950 mg, 84%).

Step 2: tert-Butyl (1-((5-(4-methyl-4-((3-(trifluoromethyl)phenyl)sulfonyl)tetrahydro-2H-pyran-2-yl)-3-(trifluoromethyl)-1H-pyrazol-1-yl)methyl)cyclopropyl)carbamate To a stirred solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8 product, Example 19] (500 mg, 1.13 mmol, 1 eq) in DMF (10 ml), KOtBu (1M in THF, 2.2 ml, 2.26 mmol, 2 eq) and (1-((tert-butoxycarbonyl)amino)cyclopropyl)methyl methanesulfonate (599 mg, 2.26 mmol, 2 eq) were added at 0° C. The RM was stirred for 18 h at 100° C. The RM was cooled to RT and diluted with EtOAc (250 ml). The organics were washed with water (5×50 ml) and brine (50 ml), dried (Na₂SO₄), filtered and concentrated. The residue was purified by flash column chromatography (39% EtOAc in PE) to afford the title compound (330 mg, 47%).

Step 3: [cis-rac] [1-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-cyclopropyl]-amine (Example 15)

To a stirred solution of tert-butyl (1-((5-(4-methyl-4-((3-(trifluoromethyl)phenyl)sulfonyl)tetrahydro-2H-pyran-2-yl)-3-(trifluoromethyl)-1H-pyrazol-1-yl)methyl)cyclopropyl)carbamate (330 mg, 0.54 mmol, 1 eq) in DCM (10 ml), TFA (2 ml) was added at 0° C. The RM was stirred for 4 h at RT. The RM was poured into ice water (100 ml), and the mixture was adjusted to PH~9 using sat. NaHCO₃. The product was extracted with DCM (3×50 ml), and the combined organic layers were washed with brine (50 ml), dried (Na₂SO₄), filtered and concentrated. The residue was purified by flash column chromatography (72% EtOAc in PE) to afford the title compound (36 mg). TLC system: 80% EtOAc-PE R_f: 0.29. NOE: On irradiating OCH proton NOE was observed with SCCH₃ as well as NCH₂

5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole (Example 17)

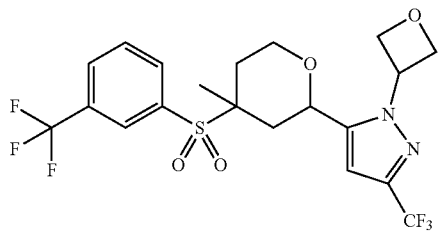 [SMILES: CC1(S(=O)(=O)c2cccc(C(F)(F)F)c2)CCOC(c2cc(C(F)(F)F)nn2C2COC2)C1]

Step 1: [cis-rac] 5-[4-Methyl-4-[[3-(trifluoromethyl) phenyl]sulfonyl]-tetrahydro-pyran-2-yl]-1-(oxetan-3-yl)-3-(trifluoromethyl)-1H-pyrazole (Example 17)

To a stirred solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8 product, Example 19] (300 mg, 0.678 mmol, 1 eq) in DMF (10 ml) was added Cs₂CO₃ (442 mg, 1.357 mmol, 2 eq) and 3-iodooxetane (150 mg, 0.814 mmol, 1.2 eq) and the RM was heated to 100° C. and stirred for 16 h. After completion of the reaction, the mixture was diluted with water (100 ml) and extracted with EtOAc (3×100 ml). The organics were washed with water (3×100 ml) and brine (100 ml), dried (Na₂SO₄) and concentrated in vacuum to give the crude product, which was purified by flash column chromatography (30% EtOAc in PE) to afford the title compound (170 mg, 50%). TLC system: EtOAc-PE 1:1; Rf: 0.36

[Cis-rac] 5-[4-methyl-4-[[3-(trifluoromethyl)phenyl]sulfonyl]-tetrahydro-pyran-2-yl]-1-(oxetan-3-yl)-3-(trifluoromethyl)-1H-pyrazole was subjected to chiral prep-SFC purification to give 37 mg of [cis-EN1] Example 17 and 31 mg of [cis-EN2] Example 17.

[cis-EN1] Example 17—analytical SFC: Lux Cellulose-2 (250×4.6 mm 5 μm) 30° C., 3 g/min, 100 bar, 10% IPA, Ret. Time 7.9 min; m/z=499.0 [M+H]⁺

[cis-EN2] Example 17—analytical SFC: Lux Cellulose-2 (250×4.6 mm 5 μm) 29.9° C., 3 g/min, 100 bar, 10% IPA, Ret. Time 9.23 min; m/z=499.0 [M+H]⁺

1-(2-Methylsulfonyl-ethyl)-5-[4-methyl-4-[[3-(trifluoromethyl)phenyl]sulfonyl]-tetrahydro-pyran-2-yl]-3-(trifluoromethyl)-1H-pyrazole (Example 19)

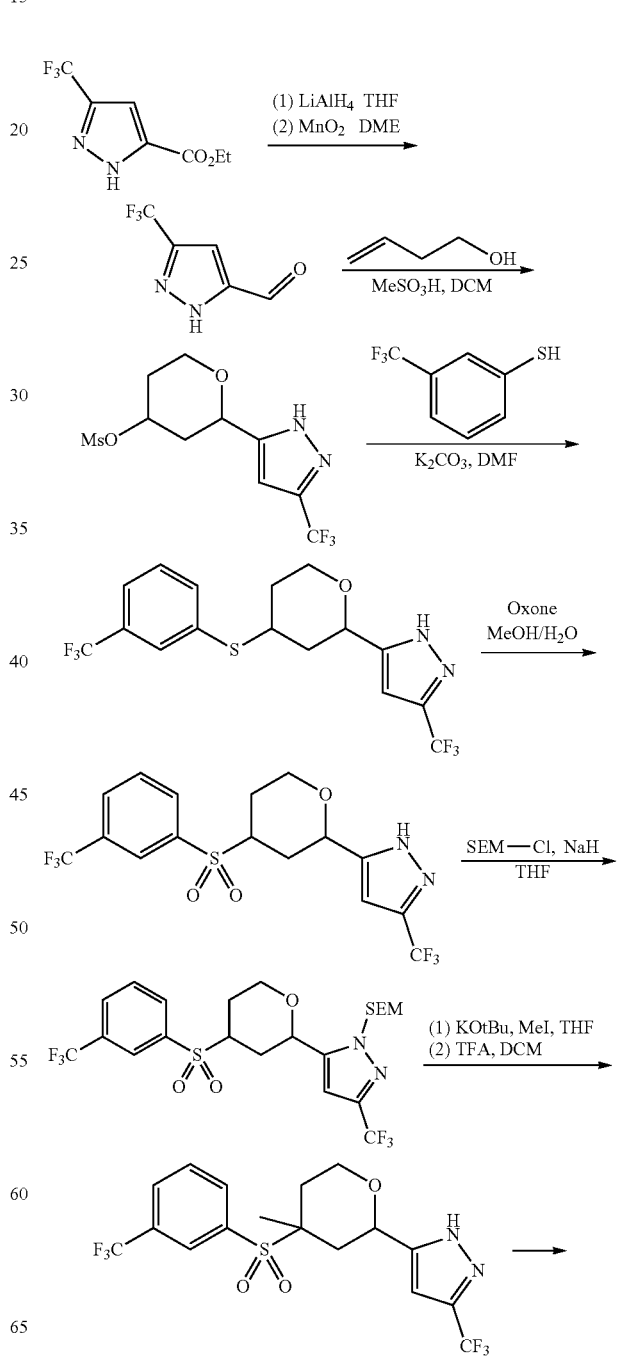

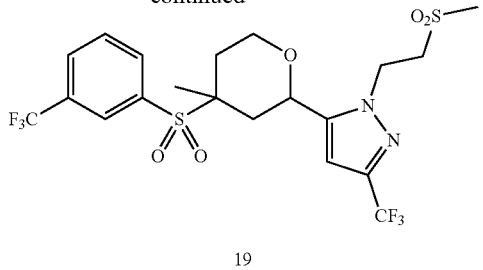

19

Step 1: (3-(Trifluoromethyl)-1H-pyrazol-5-yl)methanol

To a solution of ethyl 3-(trifluoromethyl)-1H-pyrazole-5-carboxylate (2 g, 9.615 mmol, 1 eq) in THF (30 ml) was added LiAlH$_4$ (1.09 g, 28.846 mmol, 3 eq), portionwise at 0° C. for 10 min. The RM was stirred at RT for 2 h. The RM was quenched with sat Na$_2$SO$_4$ (50 ml) and most of the solvent was removed under reduced pressure. The residue was diluted with water (100 ml) and extracted with EtOAc (3×100 ml). The combined organic layers were washed with brine (100 ml), dried over (Na$_2$SO$_4$) and concentrated to afford the title compound (1.5 g, 94%).

Step 2: 3-(Trifluoro methyl)-1H-pyrazole-5-carbaldehyde

To a stirred solution of (3-trifluoromethyl)-1H-pyrazol-5-yl)methanol (1.5 g, 9.036 mmol, 1 eq) in DME (17 ml) was added MnO$_2$ at RT, The RM was maintained at 90° C. for 16 h. The RM was filtered through Celite. The filtrate was diluted with DME (3×100 ml) and water (100 ml). The organics were washed with brine (100 ml), dried (Na$_2$SO$_4$) and the solvent was distilled off under reduced pressure. The crude product upon purification by flash chromatography (silica gel; EtOAc-PE; 0:100→15:85) afforded the title compound (1.2 g, 81%).

Step 3: 2-(3-(Trifluoromethyl)-1H-pyrazol-5-yl)tetrahydro-2H-pyran-4-yl methanesulfonate Methane sulfonic acid (4.7 ml, 73.170 mmol, 10 eq) was added to a solution of 3-(trifluoromethyl)-1H-pyrazole-5-carbaldehyde (1.2 g, 7.317 mmol, 1 eq) in DCM (40 ml) at 0° C. The, but-3-en-1-ol (0.95 ml, 10.975 mmol, 1.5 eq) was added and the mixture stirred for 16 h at RT. The RM was quenched with saturated Na$_2$CO$_3$ solution and extracted with DCM (3×100 ml). The organics were washed with water (100 ml) and brine (50 ml), dried (Na$_2$SO$_4$) and the solvent was distilled off under reduced pressure to afford the title compound (2.2 g).

Step 4: 3-(Trifluoromethyl)-5-(4-((3-(trifluoromethyl)phenyl)thio)tetrahydro-2H-pyran-2-yl)-1H-pyrazole To a solution of 3-mercaptophenol (1.9 ml, 14.012 mmol, 2 eq) in DMF (35 ml) was added K$_2$CO$_3$ (1.9 g, 14.012 mmol, 2 eq) and 2-(3-(trifluoromethyl)-1H-pyrazol-5-yl)tetrahydro-2H-pyran-4-yl methanesulfonate (2.2 g, 7.006 mmol, 1 eq). The RM was heated to 50° C. for 16 h. The RM was diluted with cold water (100 ml) and extracted with EtOAc (3×100 ml). The organics were washed with water (100 ml) and brine (100 ml), dried (Na$_2$SO$_4$) and concentrated under reduced pressure. The crude compound was purified by flash chromatography (silica gel; EtOAc-PE (15:85) to afford the title compound (1.8 g, 34% over 2 steps).

Step 5: 3-(Trifluoromethyl)-5-(4-((3-(trifluoromethyl)phenyl)sulfonyl)tetrahydro-2H-pyran-2-yl)-1H-pyrazole A solution of Oxone (5.5 g, 9.090 mmol, 2 eq) in water (15 ml) was added to a solution of 3-(trifluoromethyl)-5-(4-((3-(trifluoromethyl)phenyl)thio)tetrahydro-2H-pyran-2-yl)-1H-pyrazole (1.8 g, 4.545 mmol, 1 eq) in MeOH (22 ml) at RT. The RM was stirred for 18 h. MeOH was distilled off under reduced pressure and the residue was diluted with H$_2$O (50 ml) and extracted with EtOAc (3×50 ml). The organics were washed with water (50 ml) and brine (50 ml), dried (Na$_2$SO$_4$) and concentrated to give the crude product, which was purified flash chromatography silica gel; EtOAc:PE; 0:100→30:70) to afford the title compound (1.6 g, 82%).

Step 6: 3-(Trifluoromethyl)-5-(4-((3-(trifluoromethyl)phenyl)sulfonyl)tetrahydro-2H-pyran-2-yl)-1-((2-(trimethylsilyl)ethoxy)methyl)-1H-pyrazole To a solution of 3-(trifluoromethyl)-5-(4-((3-(trifluoromethyl)phenyl)sulfonyl)tetrahydro-2H-pyran-2-yl)-1H-pyrazole (1.6 g, 3.738 mmol, 1 eq) in THF (40 ml) was added 60% NaH (450 mg, 11.214 mmol, 3 eq) portionwise at 0° C. over 10 min. The RM was stirred at 0° C. for 30 min. SEM-Cl (0.6 ml, 3.738 mmol, 1 eq) was added dropwise at 0° and the RM was stirred at RT for 16 h. The RM was quenched with ice-water (50 ml and extracted with EtOAc (3×100 ml). The combined organic layers were washed with brine (100 ml), dried (Na$_2$SO$_4$) and concentrated. The residue upon purification by flash chromatography (silica gel; EtOAc:PE; 0:100→10:90) afforded the title compound (1.2 g, 57%).

Step 7: [cis-rac] 5-(4-Methyl-4-((3-(trifluoromethyl)phenyl)sulfonyl)tetrahydro-2H-pyran-2-yl)-3-(trifluoromethyl)-1-((2-(trimethylsilyl)ethoxy)methyl)-1H-pyrazole A solution of 3-(trifluoromethyl)-5-(4-((3-(trifluoromethyl)phenyl)sulfonyl)tetrahydro-2H-pyran-2-yl)-1-((2-(trimethylsilyl)ethoxy)methyl)-1H-pyrazole (1.2 g, 2.150 mmol, 1 eq) in THF (25 ml) was cooled to −78° C. and KOtBu (1 M in TH, 4.3 ml, 4.301 mmol, 2 eq) was added dropwise. The mixture was stirred for 30 min, then methyl iodide (0.3 ml, 5.376 mmol, 2.5 eq) was added and the resulting RM was allowed to warm to RT and stirred for 16 h. The RM was quenched with water (50 ml) and extracted with EtOAc (3×100 ml). The combined organic layers were washed with water (50 ml) and brine (50 ml), dried (Na$_2$SO$_4$) and concentrated. The residue upon purification by flash chromatography (silica gel; EtOAc:PE; 0:100→10:90) afforded the title compound (1 g, 81%). TLC system: EtOAc-PE; 3:7; Rf: 0.55.

Step 8: [cis-rac] 5-(4-Methyl-4-((3-(trifluoromethyl)phenyl)sulfonyl)tetrahydro-2H-pyran-2-yl)-3-(trifluoromethyl)-1H-pyrazole To a solution of [cis-rac] 5-(4-methyl-4-((3-(trifluoromethyl)phenyl)sulfonyl)tetrahydro-2H-pyran-2-yl)-3-(trifluoromethyl)-1-((2-(trimethylsilyl)ethoxy)methyl)-1H-pyrazole (1 g, 1.748 mmol, 1 eq) in DCM (8 ml)/TFA (8 ml) was added at 0° C. over 5 min. The resulting mixture was stirred at RT for 2 h. The RM was concentrated under reduced pressure. The residue was diluted with a aqueous NaHCO$_3$ (pH~8) and extracted with DCM (3×100 ml). The combined organic extracts were washed with brine (50 ml), dried (anhydrous Na$_2$SO$_4$) and concentrated under reduced pressure. The crude product was purified by column chromatography (silica gel; EtOAc:PE; 0:100→20:80) to afford the title compound (300 mg, 38%).

Step 9: [cis-rac] 1-(2-Methylsulfonyl-ethyl)-5-[4-methyl-4-[[3-(trifluoromethyl)phenyl]sulfonyl]-tetrahydro-pyran-2-yl]-3-(trifluoromethyl)-1H-pyrazole (Example 19)

To a solution of [cis-rac] 5-(4-methyl-4-((3-(trifluoromethyl)phenyl)sulfonyl)tetrahydro-2H-pyran-2-yl)-3-(trifluoromethyl)-1H-pyrazole (300 mg, 0.6787 mmol, 1 eq) in MeCN (35 ml) was added K$_2$CO$_3$ (280 mg, 2.0361 mmol, 3 eq) and 1-bromo-2-(methylsulfonyl)ethane (152 mg, 0.814 mmol, 2 eq). The RM was heated to 80° C. for 6 h. The mixture was diluted with H$_2$O (50 ml) and extracted with EtOAc (3×50 ml). The organics were washed with water (50 ml) and brine (50 ml), dried (Na$_2$SO$_4$) and concentrated to give the crude product, which was purified by flash chromatography (silica gel; EtOAc:PE; 0:100→40:60) to afford the title compound. (300 mg, 80%). TLC system: EtOAc-PE; 6:4; Rf: 0.30.

[Cis-rac] 1-(2-methylsulfonyl-ethyl)-5-[4-methyl-4-[[3-(trifluoromethyl)phenyl]sulfonyl]-tetrahydro-pyran-2-yl]-3-(trifluoromethyl)-1H-pyrazole was subjected to chiral prep-SFC purification to give 52 mg of [cis-EN1] Example 19 and 55 mg of [cis-EN2] Example 19.

[cis-EN1] Example 19—analytical SFC: Lux Amylose-2 (250×4.6 mm 5 µm) 29.8° C., 3 g/min, 100 bar, 20% IPA, Ret. Time 2.49 min; m/z=549.0 [M+H]$^+$

[cis-EN2] Example 19—analytical SFC: Lux Amylose-2 (250×4.6 mm 5 µm) 29.9° C., 3 g/min, 100 bar, 20% IPA, Ret. Time 4.933 min; m/z=549.0 [M+H]$^+$ Examples 6 and 24, 13, 18 and 20

These compounds were obtained from the product of step 8 of Example 19 as described in detail in the following:

General Scheme:

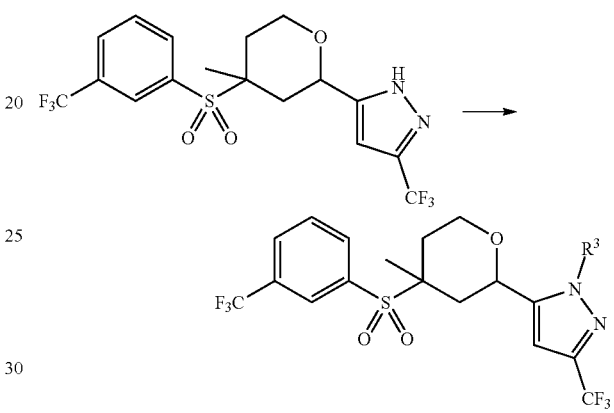

Product of step 8 of Example 19

| Example | Reaction conditions | Product |
|---|---|---|
| 6 and 24 | (1) Br—C(CH$_3$)$_2$—CH$_2$—CO$_2$Et, Cs$_2$CO$_3$, DMF; (2) LiAlH$_4$, THF |  |
| | | 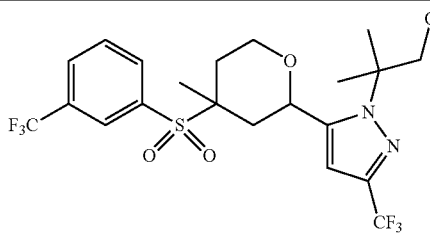 |
| 13 | Br—CH$_2$—C(CH$_3$)$_2$—C(O)NH$_2$, Cs$_2$CO$_3$, DMF |  |

| Example | Reaction conditions | Product |
|---|---|---|
| 18 | (1) K2CO3, CH3CN<br>(2) Oxone MeOH-H2O |  |
| 20 | K2CO3, acetonitrile, 80° C., 6 h | 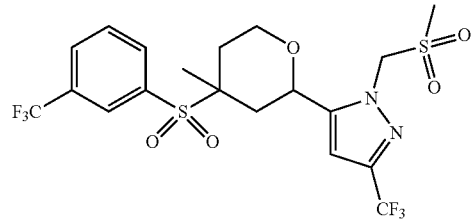 [SMILES: CC1(S(=O)(=O)c2cccc(C(F)(F)F)c2)CCOC(c2cc(C(F)(F)F)nn2CS(C)(=O)=O)C1] |

Synthesis of Example 6 and Example 24 was carried out as follows:

Step 1: [cis-rac] Ethyl 2-methyl-2-(5-(4-methyl-4-((3-(trifluoromethyl)phenyl)sulfonyl)tetrahydro-2H-pyran-2-yl)-3-(trifluoromethyl)-1H-pyrazol-1-yl) propanoate and [cis-rac] Ethyl 2-methyl-3-(5-(4-methyl-4-((3-(trifluoromethyl)phenyl)sulfonyl) tetrahydro-2H-pyran-2-yl)-3-(trifluoromethyl)-1H-pyrazol-1-yl)propanoate To a solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (0.9 g, 2.03 mmol, 1 eq) and CS2CO3 (1.32 g, 4.06 mmol 2 eq) in DMF (15 ml) was added one portion ethyl 2-bromo-2-methylpropanoate (1.18 g, 6.09 mmol, 3 eq). The RM was heated to 70° C., after 2 h an additional portion of ethyl 2-bromo-2-methylpropanoate was added and heating continued for 24 h. The residue was diluted with H2O (20 ml) and extracted with EtOAc (3×10 ml), washed with water (20 ml) and brine (20 ml), dried (Na2SO4) and concentrated to give the crude product, which was purified by flash chromatography (silica-gel; 100-200 mesh, eluent 15-30% EtOAc in PE) to afford the title compounds as a mixture (0.3 g).

Step 2: [cis-rac] 2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol (Example 6) and [cis-rac] 2-Methyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol (Example 24)

To a solution of a mixture of the products from the previous step (0.3 g, 0.53 mmol, 1 eq) in THF (10 ml) was added LiAlH4 (1M in THF, 1.61 ml, 1.618 mmol, 3 eq) portionwise at −30° C. over 10 min. The mixture was stirred at 0° C. for 3 h. The mixture was quenched with sat Na2SO4 (5 ml), and most of the solvent was removed under reduced pressure. The residue was diluted with water (20 ml) and extracted with EtOAc (3×10 ml). The combined organic layers were washed with brine (20 ml), dried (Na2SO4) and concentrated to provide the crude product which upon column chromatography (silica-gel; 100-200 mesh, eluent 25-30% EtOAc in PE) afforded [cis-rac] 2-methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol (Example 6) (145 mg, over 2 steps 14%) [NOE: On irradiating OCH proton NOE was observed with SCCH3 as well as NC(CH3)2] and [cis-rac] 2-methyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol (Example 24) (25 mg after prep-HPLC purification).

[Cis-rac] 2-methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol was subjected to chiral prep-SFC purification to give 45 mg of [cis-EN1] Example 6 and 46 mg of [cis-EN2] Example 6.

[cis-EN1] Example 6—analytical HPLC: Chiralpak AD-H (250×4.6 mm 5 μm), n-Hexane:EtOH (85:15), 1 ml/min, Ret. Time 6.309 min; m/z=515.0 [M+H]+

[cis-EN2] Example 6—analytical HPLC: Chiralpak AD-H (250×4.6 mm 5 μm), n-Hexane:EtOH (85:15), 1 ml/min, Ret. Time 8.924 min; m/z=515.0 [M+H]+

Synthesis of Example 13 was carried out as follows:

2,2-Dimethyl-3-[5-[4-methyl-4-[[3-(trifluoromethyl) phenyl]sulfonyl]-tetrahydro-pyran-2-yl]-3-(trifluoromethyl)-1H-pyrazol-1-yl]-propionamide (Example 13)

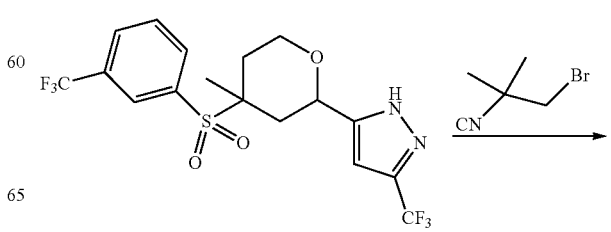

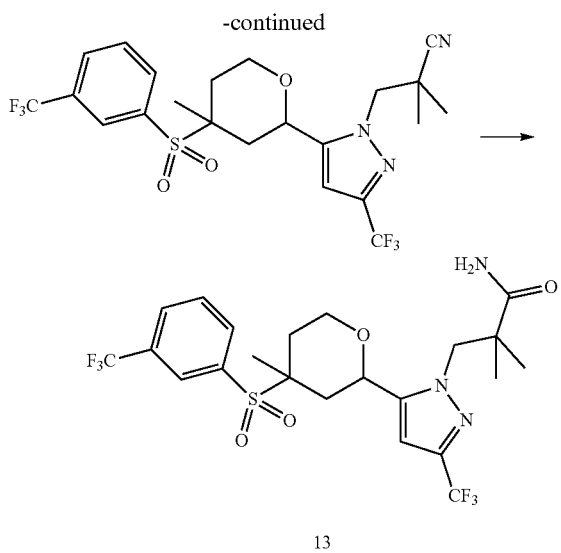

13

Preparation of 1-Bromo-2-isocyano-2-methylpropane

Isobutyronitrile (27.0 g, 390 mmol) was added to a LDA solution (292 mL, 2 M in THF) at −78° C. The RM was stirred at −78° C. for 1 h. To the RM was added a solution of 1,2-dibromomethane (202 g, 1170 mmol) at −78° C. and the resulting mixture was stirred for 16 h at RT. The RM was cooled to −70° C. and quenched with saturated ammonium chloride solution. It was then extracted with EtOAc (3×150 ml) and the combined organic layer was washed with brine and dried over anhydrous $Na_2SO_4$. The solvent was distilled under reduced pressure to give the crude product, which was purified by high vacuum distillation (80° C./0.1 mm Hg) to give 3-bromo-2,2-dimethylpropanenitrile (7 g).

Step 1: [cis-rac] 2,2-Dimethyl-3-(5-(4-methyl-4-(3-(trifluoromethyl)phenylsulfonyl)tetrahydro-2H-pyran-2-yl)-3-(trifluoromethyl)-1H-pyrazol-1-yl)propanenitrile To a stirred suspension of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (0.40 g, 0.904 mmol) and $Cs_2CO_3$ (0.590 g, 1.809 mmol) in DMF (5 mL) was added 3-bromo 2,2-dimethylpropanenitrile (0.293 g, 1.809 mmol) at RT. The RM was stirred for 16 h at 110° C. The RM was cooled to RT, diluted with EtOAc (50 ml), and washed with water (2×30 ml) and brine (50 ml). The organics were dried over anhydrous $Na_2SO_4$, filtered and the solvent was concentrated under reduced pressure. The crude product was purified by column chromatography (silica gel 100-200 mesh, 30% EtOAc in PE) to afford [cis-rac] 2,2-dimethyl-3-(5-(4-methyl-4-(3-(trifluoromethyl)phenylsulfonyl)tetrahydro-2H-pyran-2-yl)-3-(trifluoromethyl)-1H-pyrazol-1-yl)propanenitrile (0.21 g). TLC system: 50% EtOAc-PE; Rf: 0.3.

Step 2: [cis-rac] 2,2-Dimethyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propionamide (Example 13)

To a stirred solution of 2,2-dimethyl-3-(5-(4-methyl-4-(3-(trifluoromethyl)phenylsulfonyl)tetrahydro-2H-pyran-2-yl)-3-(trifluoromethyl)-1H-pyrazol-1-yl)propanenitrile (0.21 g, 0.401 mmol) in DMSO (3 ml), KOH (0.067 g, 1.204 mmol) and $H_2O_2$ (30% aqueous) (0.5 ml) were added at 0° C. The RM was stirred for 2 h at RT. The mixture was filtered to afford the title compound (0.12 g, 54%). TLC system: 80% EtOAc-PE; Rf: 0.3.

[Cis-rac] 2,2-Dimethyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propionamide was subjected to chiral prep-SFC purification to give 20 mg of [cis-EN1] Example 13 and 20 mg of [cis-EN2] Example 13.

[cis-EN1] Example 13—analytical HPLC: Chiralpak ADH (250×4.6 mm 5 µm), n-Hexane:EtOH (70:30), 1 ml/min, Ret. Time 5.649 min; m/z=542.1 [M+H]$^+$; $^1$H NMR ($CDCl_3$): δ 8.16 (s, 1H), 8.10 (d, 1H), 7.97-7.96 (d, 1H), 7.79-7.76 (t, 1H), 6.47 (s, 1H), 5.74 (br s, 1H), 5.15 (br s, 1H), 4.78-4.76 (d, 1H), 4.54-4.51 (d, 1H), 4.12-4.05 (m, 2H), 3.77-3.73 (m, 1H), 2.39-2.28 (m, 2H), 1.86-1.84 (m, 1H), 1.57-1.48 (m, 4H), 1.36 (m, 3H), 1.28 (m, 3H).

[cis-EN2] Example 13—analytical HPLC: Chiralpak ADH (250×4.6 mm 5 µm), n-Hexane:EtOH (70:30), 1 ml/min, Ret. Time 9.923 min; m/z=542.1 [M+H]$^+$; $^1$H NMR ($CDCl_3$): δ 8.16 (s, 1H), 8.10 (d, 1H), 7.97-7.96 (d, 1H), 7.79-7.76 (t, 1H), 6.47 (s, 1H), 5.75 (br s, 1H), 5.17 (br s, 1H), 4.78-4.76 (d, 1H), 4.54-4.51 (d, 1H), 4.12-4.05 (m, 2H), 3.78-3.73 (m, 1H), 2.39-2.28 (m, 2H), 1.87-1.84 (m, 1H), 1.51-1.48 (m, 4H), 1.36 (m, 3H), 1.28 (m, 3H).

Synthesis of Example 18 was carried out as follows:

Step 1: [cis-rac] 5-(4-Methyl-4-((3-(trifluoromethyl)phenyl)sulfonyl)tetrahydro-2H-pyran-2-yl)-1-((methylthio)methyl)-3-(trifluoromethyl)-1H-pyrazole and [cis-rac] 3-(4-Methyl-4-((3-(trifluoromethyl)phenyl)sulfonyl)tetrahydro-2H-pyran-2-yl)-1-((methylthio)methyl)-5-(trifluoromethyl)-1H-pyrazole To a solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (300 mg, 0.6787 mmol, 1 eq) in acetonitrile (35 ml) was added $K_2CO_3$ (280 mg, 2.0361 mmol 3 eq) and (chloromethyl)(methyl)sulfane (78 mg, 0.814 mmol, 1.2 eq). The RM was heated to 80° C. for 6 h. The mixture was diluted with water (50 ml) and extracted with EtOAc (3×50 ml), washed with water (50 ml) and brine (50 ml), dried ($Na_2SO_4$) and concentrated to give the crude compound, which was purified by flash chromatography (silica gel; EtOAc:PE; 0:100→15:75) to afford a mixture of the title compounds (250 mg, 73%).

Step 2: [cis-rac] 1-(Methylsulfonyl-methyl)-5-[4-methyl-4-[[3-(trifluoromethyl)phenyl]sulfonyl]-tetrahydro-pyran-2-yl]-3-(trifluoromethyl)-1H-pyrazole (Example 18) and 3-(4-Methyl-4-((3-(trifluoromethyl)phenyl)sulfonyl)tetrahydro-2H-pyran-2-yl)-1-((methylsulfonyl)methyl)-5-(trifluoromethyl)-1H-pyrazole A solution of Oxone (611 mg, 0.996 mmol, 2 eq) in water (5 ml) was added to a solution of a mixture of the products from the previous step (250 mg, 0.498 mmol, 1 eq) in MeOH (14 ml) at RT and the RM was stirred for 16 h. MeOH was distilled off under reduced pressure and the residue was diluted with $H_2O$ (100 ml) and extracted with EtOAc (3×50 ml). The organics were washed with aq $NaHCO_3$ (50 ml), water (50 ml) and brine (50 ml), dried ($Na_2SO_4$) and concentrated to give the crude compound, which was purified by flash chromatography (silica gel; EtOAc:PE; 0:100→30:70) to afford [cis-rac] 1-(methylsulfonyl-methyl)-5-[4-methyl-4-[[3-(trifluoromethyl)phenyl]sulfonyl]-tetrahydro-pyran-2-yl]-3-(trifluoromethyl)-1H-pyrazole (Example 18) (65 mg, 24%). TLC system: EtOAc-PE; 4:6; Rf: 0.65. Also obtained was 3-(4-methyl-4-((3-(trifluoromethyl)phenyl)sulfonyl)tetrahydro-2H-pyran-2-yl)-1-((methylsulfonyl)methyl)-5-(trifluoromethyl)-1H-pyrazole (52 mg, 19%).

[cis-rac] Example 18—m/z=535.0 [M+H]$^+$

Synthesis of Example 20 was carried out as follows:

Step 1: [cis-rac] 3-[5-[4-Methyl-4-[[3-(trifluoromethyl)phenyl]sulfonyl]-tetrahydro-pyran-2-yl]-3-(trifluoromethyl)-1H-pyrazol-1-yl]-thietane-1,1-dioxide (Example 20)

To a solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (300 mg, 0.6787 mmol, 1 eq) in acetonitrile (25 ml), was added K$_2$CO$_3$ (280 mg, 2.0361 mmol 3 eq) and 3-bromothietane 1,1-dioxide (150 mg, 0.814 mmol, 1.2 eq). The RM was heated to 80° C. for 6 h. The RM was diluted with H$_2$O (50 ml) and extracted with EtOAc (3×50 ml). The organics were washed with water (50 ml) and brine (50 ml), dried (Na$_2$SO$_4$) and concentrated to give the crude product, which was purified by flash chromatography (silica gel; EtOAc:PE; 0:100→40:60) to afford the title compound (200 mg, 54%). TLC system: EtOAc-PE; 6:4; Rf: 0.55.

[Cis-rac] 3-[5-[4-Methyl-4-[[3-(trifluoromethyl)phenyl]sulfonyl]-tetrahydro-pyran-2-yl]-3-(trifluoromethyl)-1H-pyrazol-1-yl]-thietane-1,1-dioxide was subjected to chiral prep-SFC purification to give 50 mg of [cis-EN1] Example 20 and 60 mg of [cis-EN2] Example 20.

[cis-EN1] Example 20—analytical SFC: Chiralcel OJ-H (250×4.6 mm 5 μm) 30.1° C., 3 g/min, 100 bar, 10% MeOH, Ret. Time 4.18 min; m/z=547.0 [M+H]$^+$

[cis-EN2] Example 20—analytical SFC: Chiralcel OJ-H (250×4.6 mm 5 μm) 30.1° C., 3 g/min, 100 bar, 10% MeOH, Ret. Time 6.32 min; m/z=547.0 [M+H]$^+$ Further, Example 20 could in theory also be synthesized from the product of step 8 of Example 19 by reacting said product with t-BuOK and 3-bromothietane 1,1-dioxide in N-methylpyrrolidone (NMP) under irradiation (μλ).

Synthesis of Examples 21, 25, 26, 28 and 29 was carried out as described herein below:

1-(Methoxymethyl)-5-[4-methyl-4-[[3-(trifluoromethyl)phenyl]sulfonyl]-tetrahydro-pyran-2-yl]-3-(trifluoromethyl)-1H-pyrazole (Example 21)

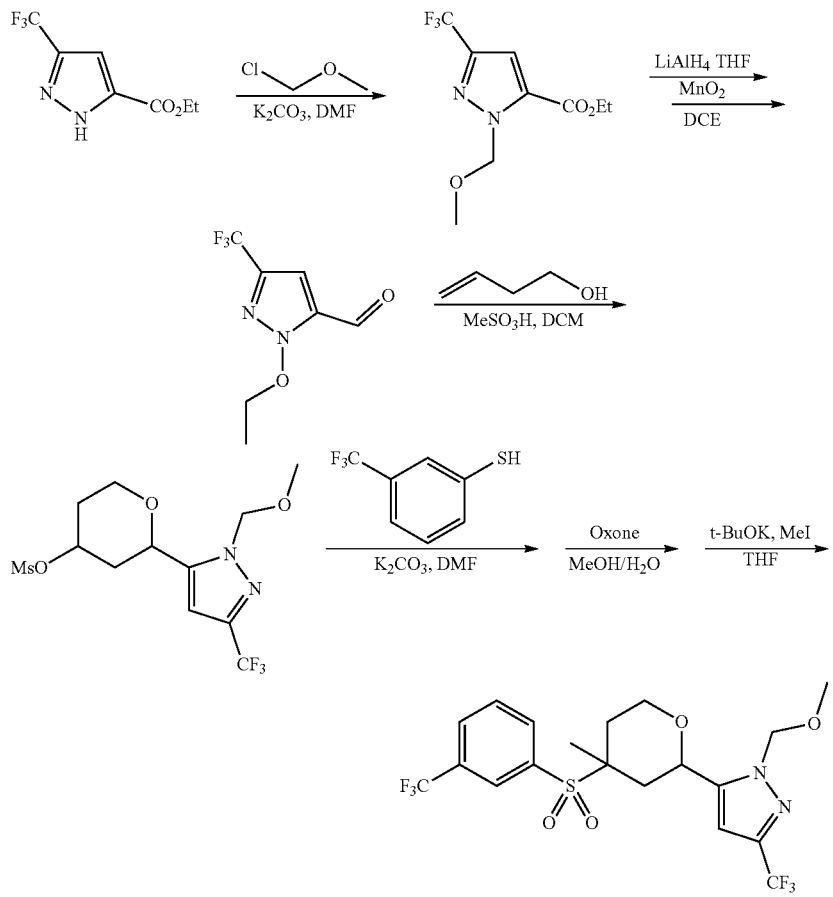

21

Example 21 can be obtained by analogous procedures as described above.

Synthesis of Example 21 was carried out as follows:

Step 1: Ethyl 1-(methoxymethyl)-3-(trifluoromethyl)-1H-pyrazole-5-carboxylate To a stirred solution of ethyl 3-(trifluoromethyl)-1H-pyrazole-5-carboxylate (2.0 g, 9.615 mmol, 1 eq) in DMF (50 ml), was added $K_2CO_3$ (3.9 g, 28.845 mmol, 3 eq) and MOM-Cl (1.5 ml 19.230 mmol 2 eq) at 0° C. The reaction mixture was stirred at RT for 16 h, quenched with cold water (60 ml) and extracted with EtOAc (3×50 ml). The combined organic layers were washed with water (2×50 ml), brine (60 ml), dried ($Na_2SO_4$) and concentrated under reduced pressure. The crude residue upon purification by flash chromatography (silica gel; EtOAc-PE; 0:100→4:96) afforded the title compound (2.0 g, 82%).

Step 2: (1-(Methoxymethyl)-3-(trifluoromethyl)-1H-pyrazol-5-yl)methanol $LiAlH_4$ (1.0 M in THF; 23.80 ml, 23.80 mmol, 3 eq) was added dropwise to a solution of ethyl 1-(methoxymethyl)-3-(trifluoromethyl)-1H-pyrazole-5-carboxylate (2.0 g, 7.93 mmol, 1 eq) in THF (40 ml) at 0° C., and the reaction mixture was stirred at RT for 2 h. The mixture was carefully quenched with saturated $NH_4Cl$ solution (45 ml) at 0° C. and filtered through a bed of celite. The filtrate was extracted with EtOAc (3×50 ml). The combined organic layers were washed with water (70 ml) and brine (50 ml), dried ($Na_2SO_4$) and concentrated to afford the title compound (1.40 g 84%).

Step 3: 1-(Methoxymethyl)-3-(trifluoromethyl)-1H-pyrazole-5-carbaldehyde

To a solution of (1-(methoxymethyl)-3-(trifluoromethyl)-1H-pyrazol-5-yl)methanol (1.40 g, 6.603 mmol, 1 eq) in 1,2-dichloroethane (25 ml), was added $MnO_2$ (1.72 g, 19.81 mmol, 3 eq) at RT and the mixture was stirred at 90° C. for 3 h. After completion of the reaction, the mixture was filtered through a celite bed and concentrated under reduced pressure to afford the title compound (1.2 g).

Step 4: 2-(1-(Methoxymethyl)-3-(trifluoromethyl)-1H-pyrazol-5-yl)tetrahydro-2H-pyran-4-yl methanesulfonate To a solution of 1-(methoxymethyl)-3-(trifluoromethyl)-1H-pyrazole-5-carbaldehyde (1.0 g, 4.76 mmol, 1 eq) in DCM (20 ml) was added 3-buten-1-ol (0.6 ml, 7.14 mmol, 1.5 eq) and methane sulfonic acid (1.5 ml, 23.809 mmol, 5 eq) at 0° C. and the RM was stirred at RT for 16 h. The mixture was quenched with a cold saturated solution of aq. $Na_2CO_3$ to pH~10, and extracted with DCM (3×20 ml). The combined organic layer was washed with water (40 ml) and brine (30 ml), dried ($Na_2SO_4$) and upon concentration afforded the title compound (1.2 g).

Step 5: 1-(Methoxymethyl)-3-(trifluoromethyl)-5-(4-((3-(trifluoromethyl)phenyl)thio)tetrahydro-2H-pyran-2-yl)-1H-pyrazole To a solution of 3-(trifluoromethyl)benzenethiol (0.8 ml, 5.58 mmol, 2 eq) in DMF (30 ml), was added $K_2CO_3$ (1.15 g, 8.37 mmol, 3 eq) followed by 2-(1-(methoxymethyl)-3-(trifluoromethyl)-1H-pyrazol-5-yl)tetrahydro-2H-pyran-4-yl methanesulfonate (1.0 g, 2.79 mmol, 1 eq) in DMF (20 ml) and the reaction mixture was heated to 50° C. and stirred for 6 h. Stirring was continued for 10 h at RT. After completion of the reaction the mixture was diluted with cold water (40 ml), extracted with EtOAc (3×20 ml), washed with water (45 ml) and brine (30 ml), dried ($Na_2SO_4$) and concentrated under reduced pressure. The crude residue upon purification by flash chromatography (silica gel; EtOAc-PE; 5:95→20:80) afforded the title compound (0.8 g, 28% over 3 steps).

Step 6: 1-(Methoxymethyl)-3-(trifluoromethyl)-5-(4-((3-(trifluoromethyl)phenyl)sulfonyl)tetrahydro-2H-pyran-2-yl)-1H-pyrazole Oxone (1.67 g, 5.45 mmol, 3 eq) in water (10 ml) was added to a solution of 1-(methoxymethyl)-3-(trifluoromethyl)-5-(trifluoromethyl)phenyl)thio)tetrahydro-2H-pyran-2-yl)-1H-pyrazole (0.8 g, 1.818 mmol, 1 eq) in methanol (15 ml) at RT and the mixture was stirred for 16 h. After completion of the reaction, methanol was distilled off under reduced pressure and the residue was diluted with water (40 ml) and sat. aq. $NaHCO_3$ (to pH~8-9). The mixture was then extracted with EtOAc (3×20 ml), washed with water (40 ml) and brine (30 ml), dried ($Na_2SO_4$) and concentrated to give the crude compound, which upon flash chromatography (silica gel; EtOAc-PE; 10:90→35:65) afforded the title compound (650 mg, 76%).

Step 7: [cis-rac] 1-(Methoxymethyl)-5-[4-methyl-4-[[3-(trifluoromethyl)phenyl]sulfonyl]-tetrahydro-pyran-2-yl]-3-(trifluoromethyl)-1H-pyrazole (Example 21)

To a solution of 1-(methoxymethyl)-3-(trifluoromethyl)-5-(4-((3-(trifluoromethyl)phenyl)sulfonyl)tetrahydro-2H-pyran-2-yl)-1H-pyrazole (0.650 g, 1.377 mmol, 1 eq) in THF (30 ml) at −78° C., was added t-BuOK (1M solution in THF, 2.75 ml, 2.75 mmol, 2.0 eq) dropwise. The RM was stirred for 30 min before methyl iodide (0.3 ml, 3.44 mmol, 2.5 eq) was added. The resulting mixture was allowed to warm to RT and stirred for 16 h. The RM was quenched with water (30 ml) and extracted with EtOAc (3×20 ml). The combined organic layer was washed with water (40 ml) and brine (30 ml), dried ($Na_2SO_4$) and concentrated under reduced pressure. The crude residue upon purification by flash chromatography (silica gel; EtOAc-PE; 20:80→40:60) afforded the title compound (0.170 g, 25%). TLC system: EtOAc-PE; 1:1; Rf: 0.40.

[Cis-rac] 1-(methoxymethyl)-5-[4-methyl-4-[[3-(trifluoromethyl)phenyl]sulfonyl]-tetrahydro-pyran-2-yl]-3-(trifluoromethyl)-1H-pyrazole was subjected to chiral prep-SFC purification to give 38 mg of [cis-EN1] Example 21 and 38 mg of [cis-EN2] Example 21.

[cis-EN1] Example 21—analytical SFC: Chiralpak AD-H (250×4.6 mm 5 μm) 29.8° C., 3 g/min, 100 bar, 10% MeOH, Ret. Time 1.77 min; m/z=487.0 [M+H]$^+$

[cis-EN2] Example 21—analytical SFC: Chiralpak AD-H (250×4.6 mm 5 μm) 30.6° C., 3 g/min, 100 bar, 10% MeOH, Ret. Time 2.61 min; m/z=487.0 [M+H]$^+$

2-[3-(Difluoro-methylsulfonyl)-5-[4-methyl-4-[[3-(trifluoromethyl)phenyl]sulfonyl]-tetrahydro-pyran-2-yl]-1H-pyrazol-1-yl]-ethanol (Example 25)

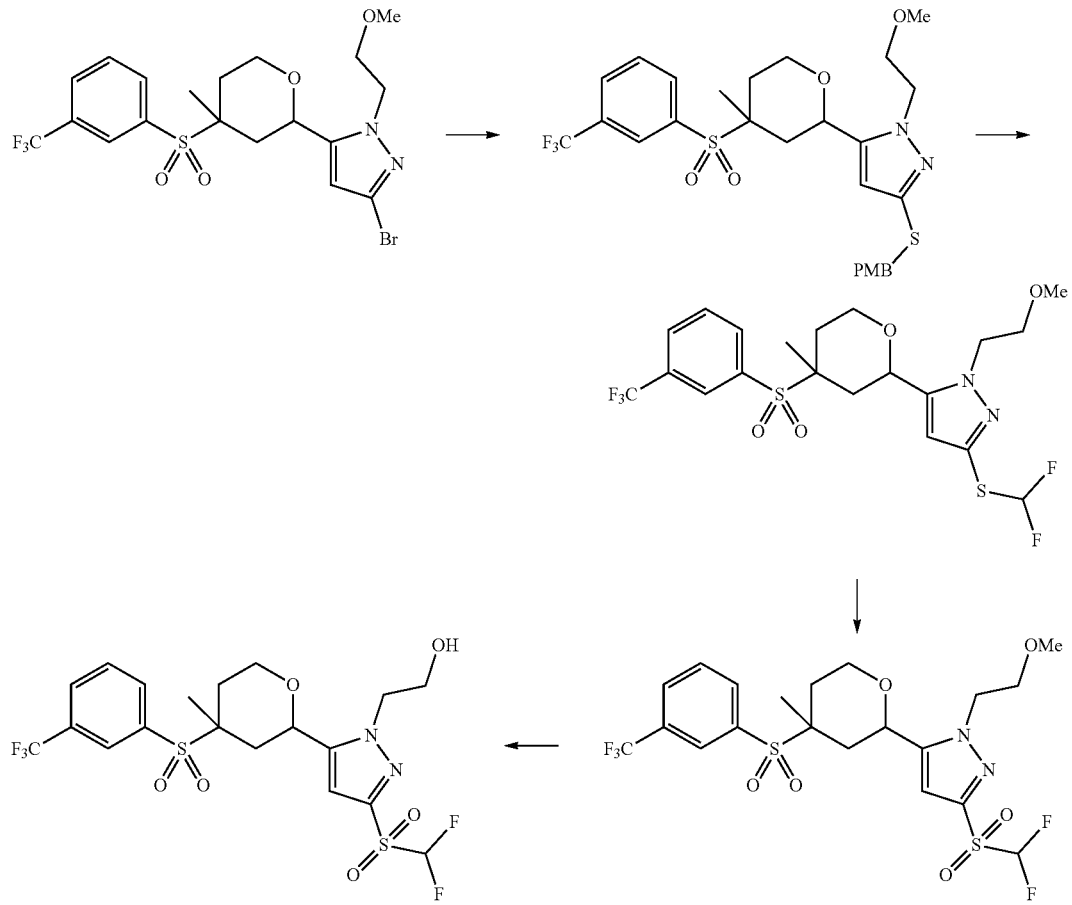

25

Step 1: 3-((4-Methoxybenzyl)thio)-1-(2-methoxyethyl)-5-(4-methyl-4-((3-(trifluoromethyl)phenyl)sulfonyl)tetrahydro-2H-pyran-2-yl)-1H-pyrazole To a solution of 3-bromo-1-(2-methoxyethyl)-5-(4-methyl-4-((3-(trifluoromethyl)phenyl)sulfonyl)tetrahydro-2H-pyran-2-yl)-1H-pyrazole [step 7, examples 4 & 23] (2 g, 3.92 mmol, 1 eq) and DIPEA (4.53 ml, 27.4 mmol, 7 eq) in 1,4-Dioxane (20 ml), was added PMB-SH (0.8 ml, 5.88 mmol, 1.5 eq). The mixture was degassed with argon gas for 15 min, and Xantphos (158 mg, 0.274 mmol, 0.07 eq), followed by $Pd_2(dba)_3$ (251 mg, 0.274 mmol, 0.07 eq) were added and it was again degassed with argon gas for 15 min. The resulting RM was stirred at 100° C. for 16 h under argon. The mixture was filtered through a celite bed and the filtrate concentrated. The crude product was purified by flash column chromatography (0-25% EtOAc in PE) afforded the title compound (1.6 g, 70%).

Step 2: 3-((Difluoromethyl)thio)-1-(2-methoxyethyl)-5-(4-methyl-4-((3-(trifluoromethyl)phenyl)sulfonyl)tetrahydro-2H-pyran-2-yl)-1H-pyrazole A mixture of 3-((4-methoxybenzyl)thio)-1-(2-methoxyethyl)-5-(4-methyl-4-((3-(trifluoromethyl)phenyl)sulfonyl)tetrahydro-2H-pyran-2-yl)-1H-pyrazole (1.6 g, 2.73 mmol, 1 eq) and TFA (4 ml) in anisole (1.6 ml) was stirred at 100° C. for 18 h. The RM was concentrated, before the residue was cooled to 0° C. and quenched with solid $K_2CO_3$ (to pH~10). Subsequently DMF (5 ml) was added, before the RM was stirred at 100° C. under Freon gas conditions for 8 h. The RM was diluted with water (50 ml) and extracted with EtOAc (3×50 ml). The combined organic layer was washed with water (2×50 ml) and brine (50 ml), then dried ($Na_2SO_4$) and concentrated. The crude product was purified by flash column chromatography (0-100% EtOAc in PE) to afford the title compound (0.5 g).

Step 3: 3-((Difluoromethyl)sulfonyl)-1-(2-methoxyethyl)-5-(4-methyl-4-((3-(trifluoromethyl)phenyl)sulfonyl)tetrahydro-2H-pyran-2-yl)-1H-pyrazole To a solution of 3-((difluoromethyl)thio)-1-(2-methoxyethyl)-5-(4-methyl-4-((3-(trifluoromethyl)phenyl)sulfonyl)tetrahydro-2H-pyran-2-yl)-1H-pyrazole (0.5 g, 0.97 mmol, 1 eq) in $CHCl_3$ (10 ml) was added m-CPBA (0.5 g, 2.91 mmol, 3 eq) at 0° C. The RM was then allowed to stir at RT for 48 h. Reaction progress was monitored by TLC. The RM was passed through celite, and the organic layer was washed with 20 ml NaHCO₃-solution. The aqueous layers were extracted with DCM (2×30 ml). The organic layers were then washed with brine (20 ml), dried (Na₂SO₄), and concentrated to afford the crude product which was purified by column chromatography (silica-gel; 100-200 mesh, 25-35% EtOAc in PE) to afford the title compound (0.35 g, 23% over 3 steps).

Step 4: [cis-rac] 2-[3-(Difluoro-methylsulfonyl)-5-[4-methyl-4-[[3-(trifluoromethyl)phenyl]sulfonyl]-tetrahydro-pyran-2-yl]-1H-pyrazol-1-yl]-ethanol (Example 2)

To a stirred solution of 3-((difluoromethyl)sulfonyl)-1-(2-methoxyethyl)-5-(4-methyl-4-((3-(trifluoromethyl)phenyl)sulfonyl)tetrahydro-2H-pyran-2-yl)-1H-pyrazole (0.25 g, 0.45 mmol, 1.0 eq) in DCM (10 ml) 1M BCl₃ in DCM (1.83 ml, 1.83 mmol, 3.0 eq) was added at 0° C. The RM was allowed to stir at RT for 16 h. The RM was quenched with cold methanol (20 ml), and concentrated under reduced pressure. The RM was diluted with water (20 ml) and extracted with DCM (2×20 ml). The combined organic layers were washed with water (20 ml) and brine (20 ml), dried (Na₂SO₄) and concentrated under reduced pressure to afford the crude product, which upon purification by flash chromatography (silica gel; EtOAc in PE; 60:40→80:20) afforded the title compound (0.1 g, 42%). TLC system: EtOAc-PE; 6:4; Rf: 0.35.

[Cis-rac] 2-[3-(Difluoro-methylsulfonyl)-5-[4-methyl-4-[[3-(trifluoromethyl)phenyl]sulfonyl]-tetrahydro-pyran-2-yl]-1H-pyrazol-1-yl]-ethanol was subjected to chiral prep-SFC purification to give 48 mg of [cis-EN1] Example 25 and 49 mg of [cis-EN2] Example 25.

[cis-EN1] Example 25—analytical SFC: Chiralcel OJ-H (250×4.6 mm 5 μm) 29.9° C., 3 g/min, 100 bar, 10% MeOH, Ret. Time 4.16 min; m/z=533.0 [M+H]⁺

[cis-EN2] Example 25—analytical SFC: Chiralcel OJ-H (250×4.6 mm 5 μm) 30.1° C., 3 g/min, 100 bar, 10% MeOH, Ret. Time 6.23 min; m/z=533.0 [M+H]⁺

2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propionamide (Example 26)

Step 1: [cis-rac] 2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propionamide (Example 26) and [cis-rac] 2-Methyl-2-(3-(4-methyl-4-((3-(trifluoromethyl)phenyl)sulfonyl)tetrahydro-2H-pyran-2-yl)-5-(trifluoromethyl)-1H-pyrazol-1-yl)propanamide To a stirred solution [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (0.40 g, 0.904 mmol) in DMF (5 ml) were added CS₂CO₃ (883 mg, 2.714 mmol) and 2-bromo-2-methylpropionamide (300 mg, 1.809 mmol) at RT. The RM was stirred for 16 h at 100° C. The mixture was cooled to RT, diluted with EtOAc (50 ml) and washed with water (2×20 ml) and brine solution (50 mL). The organics were dried over anhydrous Na₂SO₄, filtered and the solvent was concentrated under reduced pressure to give the crude product. This was purified by RP prep HPLC to afford the title compound (160 mg). TLC system: 50% EtOAc-PE; Rf: 0.3. Also obtained was [cis-rac] 2-methyl-2-(3-(4-methyl-4-((3-(trifluoromethyl)phenyl)sulfonyl)tetrahydro-2H-pyran-2-yl)-5-(trifluoromethyl)-1H-pyrazol-1-yl)propanamide (20 mg) [NOE: On irradiating OCH proton NOE was observed with SCCH₃, but not NC(CH₃)₂.].

[Cis-rac] 2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propionamide was subjected to chiral prep-SFC purification to give 48 mg of [cis-EN1] Example 26 and 40 mg of [cis-EN2] Example 26.

[cis-EN1] Example 26—analytical HPLC: Chiralpak IA (250×4.6 mm 5 μm), n-Hexane:IPA (85:15), 1 ml/min, Ret. Time 5.802 min; m/z=528.0 [M+H]⁺; ¹H NMR (CDCl₃): δ 8.14 (s, 1H), 8.08 (d, 1H), 7.98 (d, 1H), 7.79-7.76 (t, 1H), 6.68 (s, 1H), 5.25-5.20 (m, 2H), 4.56-4.53 (m 1H), 4.06-4.03 (m, 1H), 3.61-3.56 (m, 1H), 2.40-2.31 (m, 2H), 1.87-1.83 (m, 7H), 1.48-1.43 (m, 4H).

[cis-EN2] Example 26—analytical HPLC: Chiralpak IA (250×4.6 mm 5 μm), n-Hexane:IPA (85:15), 1 ml/min, Ret. Time 7.756 min; m/z=528.0 [M+H]⁺, ¹H NMR (CDCl₃): δ 8.14 (s, 1H), 8.08 (d, 1H), 7.98 (d, 1H), 7.79-7.76 (t, 1H), 6.68 (s, 1H), 5.26-5.20 (m, 2H), 4.56-4.53 (m 1H), 4.06-4.03 (m, 1H), 3.61-3.56 (m, 1H), 2.40-2.30 (m, 2H), 1.87-1.83 (m, 7H), 1.48-1.43 (m, 4H). NOE: On irradiating OCH proton NOE was observed with SCCH₃ as well as NC(CH₃)₂.

N,N-Dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 28)

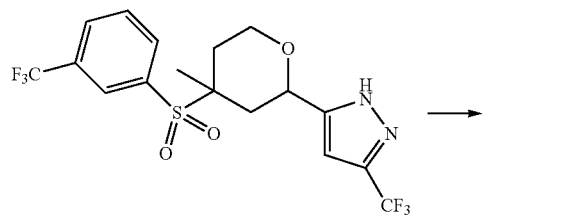

26
+ regioisomer

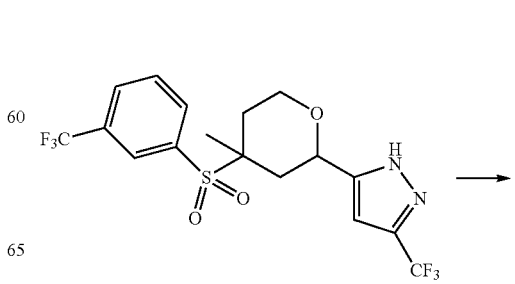

69

-continued

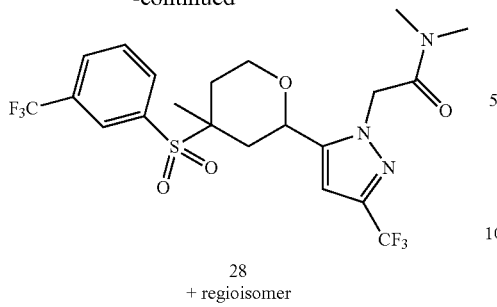

28
+ regioisomer

Step 1: [cis-rac] N,N-Dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 28) and [cis-rac] N,N-Dimethyl-2-(3-(4-methyl-4-((3-(trifluoromethyl)phenyl)sulfonyl)tetrahydro-2H-pyran-2-yl)-5-(trifluoromethyl)-1H-pyrazol-1-yl)acetamide To a stirred solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (0.40 g, 0.904 mmol) in DMF (5 ml) were added $K_2CO_3$ (0.374 g, 2.71 mmol) and 2-bromo-N,N-dimethylacetamide (0.30 g, 1.808 mmol) at RT. The RM was stirred for 16 h at 100° C. The mixture was cooled to RT and diluted with EtOAc (50 ml). The product was extracted with EtOAc. The organic layer was washed with water (2×20 ml) and brine (50 ml), and dried over anhydrous $Na_2SO_4$. The organics were filtered and the solvent was concentrated under reduced pressure. The crude product was purified by RP-HPLC (X-BRIDGE-C18; Ammonium Bicarbonate in H2O:MeCN (0:60→11:60); Flow Rate: 25 ml/min) to afford [cis-rac] N,N-dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 28) (160 mg). TLC system: 50% EtOAc-PE; Rf: 0.3. Also obtained was [cis-rac] N,N-dimethyl-2-(3-(4-methyl-4-((3-(trifluoromethyl)phenyl)sulfonyl)tetrahydro-2H-pyran-2-yl)-5-(trifluoromethyl)-1H-pyrazol-1-yl)acetamide (20 mg).

[Cis-rac] N,N-Dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide was subjected to chiral prep-SFC purification to give 55 mg of [cis-EN1] Example 28 and 50 mg of [cis-EN2] Example 28.

[cis-EN1] Example 28—analytical HPLC: Chiralpak IC (250×4.6 mm 5 μm), n-Hexane:EtOH (70:30), 1 ml/min, Ret. Time 5.437 min; m/z=528.2 [M+H]+

[cis-EN2] Example 28—analytical HPLC: Chiralpak IC (250×4.6 mm 5 μm), n-Hexane:EtOH (70:30), 1 ml/min, Ret. Time 6.467 min; m/z=528.1 [M+H]+

70

N-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 29)

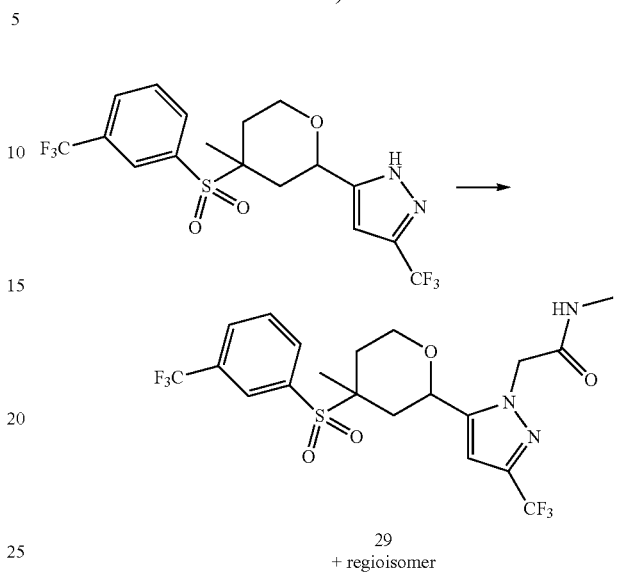

29
+ regioisomer

Step 1: [cis-rac] N-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 29) and [cis-rac] N-Methyl-2-(3-(4-methyl-4-((3-(trifluoromethyl)phenyl)sulfonyl)tetrahydro-2H-pyran-2-yl)-5-(trifluoromethyl)-1H-pyrazol-1-yl)acetamide To a stirred solution of [cis-rac] 5-(4-methyl-4-((3-(trifluoromethyl)phenyl)sulfonyl)tetrahydro-2H-pyran-2-yl)-3-(trifluoromethyl)-1H-pyrazole [step 8, example 19] (0.40 g, 0.904 mmol) in DMF (5 ml) were added $K_2CO_3$ (0.374 g, 2.71 mmol) and 2-bromo-N-methylacetamide (0.275 g, 1.809 mmol) at RT. The RM was stirred for 16 h at 110° C. The mixture was cooled to RT and diluted with EtOAc (50 ml). The product was extracted with EtOAc. The organic layer was washed with water (2×20 ml) and brine (50 ml), and dried over anhydrous $Na_2SO_4$. It was filtered and the solvent was concentrated under reduced pressure. The crude product was purified by RP-HPLC (X-BRIDGE-C18; Ammonium Bicarbonate in H2O:MeCN (0:50→12:50); Flow Rate: 25 ml/min) to afford [cis-rac] N-methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide (Example 29) (140 mg). TLC system: 50% EtOAc-PE; Rf: 0.3. Also obtained was [cis-rac] N-methyl-2-(3-(4-methyl-4-((3-(trifluoromethyl)phenyl)sulfonyl)tetrahydro-2H-pyran-2-yl)-5-(trifluoromethyl)-1H-pyrazol-1-yl)acetamide (15 mg).

[Cis-rac] N-methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide was subjected to chiral prep-SFC purification to give 60 mg of [cis-EN1] Example 29 and 48 mg of [cis-EN2] Example 29.

[cis-EN1] Example 29—analytical SFC: Lux Amylose-2 (250×4.6 mm 5 μm) 29.9° C., 3 g/min, 100 bar, 10% EtOH, Ret. Time 3.66 min; m/z=514.1 [M+H]+; $^1$H NMR (CDCl$_3$): δ 8.16 (s, 1H), 8.11-8.09 (d, 1H), 7.98-7.97 (d, 1H), 7.80-7.77 (t, 1H), 6.53 (s, 1H), 5.82 (br s, 1H), 4.95-4.78 (m, 2H), 4.59-4.56 (m, 1H), 4.10-4.06 (m, 1H), 3.71-3.66 (m, 1H), 2.80-2.79 (d, 3H), 2.48-2.43 (m, 1H), 2.34-2.33 (m, 1H), 1.99-1.95 (m, 1H), 1.54-1.47 (m, 4H).

[cis-EN2] Example 29—analytical SFC: Lux Amylose-2 (250×4.6 mm 5 μm) 30.2° C., 3 g/min, 100 bar, 10% EtOH, Ret. Time 4.81 min; m/z=514.1 [M+H]$^+$; $^1$H NMR (CDCl$_3$): δ 8.16 (s, 1H), 8.11-8.09 (d, 1H), 7.98-7.97 (d, 1H), 7.80-7.77 (t, 1H), 6.53 (s, 1H), 5.83 (br s, 1H), 4.95-4.78 (m, 2H), 4.59-4.56 (m, 1H), 4.10-4.06 (m, 1H), 3.71-3.66 (m, 1H), 2.80-2.79 (d, 3H), 2.48-2.43 (m, 1H), 2.36-2.30 (m, 1H), 1.98-1.96 (m, 1H), 1.54-1.47 (m, 4H).

Prophetic Examples: Examples 1, 8, 12, 14 and 22

The following compounds can be obtained from the product of step 8 of Example 19 by conventional alkylation procedures known to the person skilled in the art:

1. [5-[4-Methyl-4-[[3-(trifluoromethyl)phenyl]sulfonyl]-tetrahydro-pyran-2-yl]-3-(trifluoromethyl)-1H-pyrazol-1-yl]-methanol
8. 3-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-oxetan-3-ol
12. 3-[5-[4-Methyl-4-[[3-(trifluoromethyl)phenyl]sulfonyl]-tetrahydro-pyran-2-yl]-3-(trifluoromethyl)-1H-pyrazol-1-yl]-propionamide
14. Dimethyl-[2-[5-[4-methyl-4-[[3-(trifluoromethyl)phenyl]sulfonyl]-tetrahydro-pyran-2-yl]-3-(trifluoromethyl)-1H-pyrazol-1-yl]-ethyl]-amine
22. 1-[2-[5-[4-Methyl-4-[[3-(trifluoromethyl)phenyl]sulfonyl]-tetrahydro-pyran-2-yl]-3-(trifluoromethyl)-1H-pyrazol-1-yl]-ethyl]-pyrrolidin-2-one

| Example | Reaction conditions (prophetic) | Product |
|---|---|---|
| 1 | formaldehyde DCM, reflux | |
| 8 | (oxetan-3-one, trimethylsulfoxonium iodide) NaH, DMSO | |
| 12 | (acrylamide) DBU, MeCN | |
| 14 | (2-chloro-N,N-dimethylethylamine) Cs$_2$CO$_3$, DMF | |

-continued

| Example | Reaction conditions (prophetic) | Product |
|---|---|---|
| 22 | 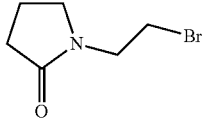 NaH, DMF | 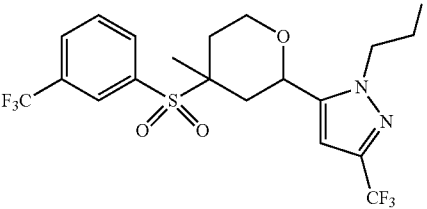 |

Prophetic Examples 7 and 16 (Steps 1 to 7 were Carried Out; Steps 8 to 14 are Prophetic)

2-Methyl-2-[3-methylsulfonyl-5-[4-methyl-4-[[3-(trifluoromethyl)phenyl]sulfonyl]-tetrahydro-pyran-2-yl]-1H-pyrazol-1-yl]-propan-1-ol (Example 7) and [1-[[3-Methylsulfonyl-5-[4-methyl-4-[[3-(trifluoromethyl)phenyl]sulfonyl]-tetrahydro-pyran-2-yl]-1H-pyrazol-1-yl]-methyl]-cyclopropyl]-amine (Example 16)

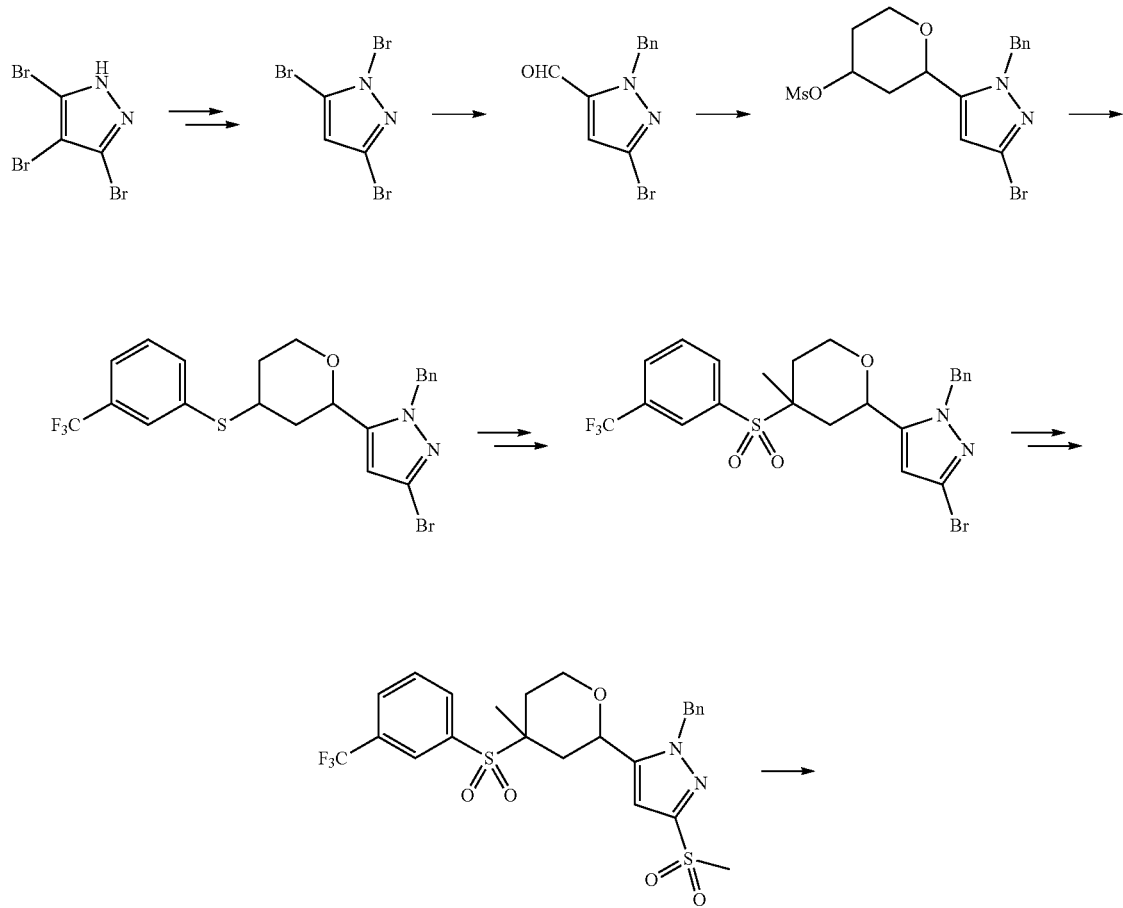

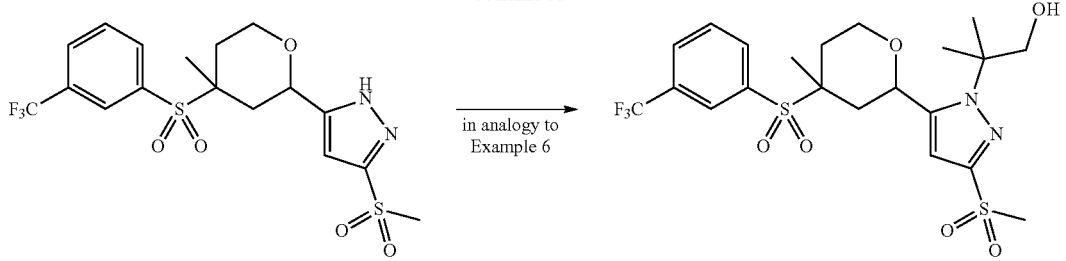

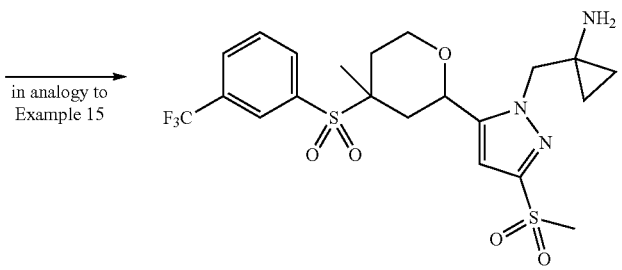

Step 1: 3,5-Dibromo-1H-pyrazole

To a solution of 3,4,5-tribromo-1H-pyrazole (25 g, 81.96 mmol, 1.0 eq) in THF (300 ml), was added n-BuLi (2.5 M in hexanes, 65.6 ml, 164 mmol, 2.0 eq) over 30 min at −78° C. and the RM was stirred at this temperature for 30 min. The RM was quenched by the dropwise addition of MeOH-THF (2:3; 125 ml) at −78° C., and stirred for an additional 1.5 h while gradually allowing it to warm to RT. The solvent was removed under reduced pressure. The residue was diluted with diethyl ether (600 ml), washed with aq. HCl (0.5 N, 60 ml) and brine (75 ml), dried (Na$_2$SO$_4$), filtered and concentrated under reduced pressure to afford the title product (16 g, 86%)

Step 2: 1-Benzyl-3,5-dibromo-1H-pyrazole

A solution of 3,5dibromo-1H-pyrazole (16 g, 111.70 mmol, 1.0 eq) in DMF (100 ml) was added 60% NaH (7.1 g, 176.99 mmol, 2.5 eq) and benzyl bromide at 0°. The mixture was then allowed to warm to RT and stirred for 12 h. The RM was quenched with sat NH$_4$Cl solution at 0° C. and extracted with EtOAc (2×300 ml). The combined organic layers were washed with water (2×200 ml) and brine (200 ml), dried over (Na$_2$SO$_4$), filtered and concentrated under reduced pressure to afford the title product (14 g).

Step 3: 1-Benzyl-3-bromo-1H-pyrazole-5-carbaldehyde

A stirred solution of 1-benzyl-3,5-dibromo-1H-pyrazole (20 g, 63.69 mmol, 1.0 eq) in THF (300 ml) was treated with iPrMgCl (1.0 M, 76.43 ml, 76.43 mmol, 1.2 eq) at −78° C. The RM was stirred for 30 min, then DMF (35 ml, 445.83 mmol, 7.0 eq) was added and the RM was gradually allowed to RT and stir for 4.5 h. The RM was quenched with aqueous NH$_4$Cl and extracted with EtOAc (2×400 ml). The combined organic layers were washed with water (300 ml) and brine (150 ml), dried (Na$_2$SO$_4$), filtered and concentrated under reduced pressure to afford the title compound (16 g, 95%).

Step 4: 2-(1-Benzyl-3-bromo-1H-pyrazol-5-yl)tetrahydro-2H-pyran-4-yl methanesulfonate A stirred solution of 1-benzyl-3-bromo-1H-pyrazole-5-carbaldehyde (10 g, 37.73 mmol, 1.0 eq) in DCM (100 ml) was treated with MsOH (24 ml, 377.3 mmol, 10.0 eq) at 0° C., stirred for 10 min and but-3-en-1-ol (2.9 ml, 37.73 mmol, 1.0 eq) was added. The RM was allowed warm to RT and stir for 16 h. The RM was quenched with sat.aq. Na$_2$CO$_3$ and extracted with DCM (2×200 ml). The combined organic layers were washed with water (150 ml) and brine (150 ml), dried (Na$_2$SO$_4$), filtered and concentrated under reduced pressure to afford the title compound (8 g, 36%).

Step 5: 1-Benzyl-3-bromo-5-(4-((3-(trifluoromethyl)phenyl)thio)tetrahydro-2H-pyran-2-yl)-1H-pyrazole A stirred solution of 3-(trifluoromethyl)benzenethiol (12 g, 57.94 mmol, 1.2 eq) in DMF (200 ml) was treated with K$_2$CO$_3$ (13 g, 96.56 mmol, 2.0 eq), stirred for 20 min at RT before a solution of 2-(1-benzyl-3-bromo-1H-pyrazol-5-yl)tetrahydro-2H-pyran-4-yl methanesulfonate (20 g, 48.28 mmol, 1.0 eq) in DMF (50 ml) was added. The resulting RM was heated to 50° C., stirred for 6 h, then brought to RT and stirred for additional 10 h. The RM was concentrated under reduced pressure and the residue was diluted with water (500 ml) and extracted with EtOAc (2×400 ml). The combined organic layers were washed with water (2×300 ml) and brine (200 ml), dried (Na$_2$SO$_4$), filtered and concentrated under reduced pressure. The crude compound upon purification by flash chromatography (silica-gel; 20% EtOAc in PE) afforded the title product (20 g).

Step 6: 1-Benzyl-3-bromo-5-(4-((3-(trifluoromethyl)phenyl)sulfonyl)tetrahydro-2H-pyran-2-yl)-1H-pyrazole Oxone (7.3 g, 302.2 mmol, 2.5 eq) in water (15 ml) was added to a solution of 1-benzyl-3-bromo-5-(4-((3-(trifluoromethyl)phenyl)thio)tetrahydro-2H-pyran-2-yl)-1H-pyrazole (4.8 g, 9.65 mmol, 1.0 eq) in MeOH (48 ml) at RT and stirred for 18 h. After completion of the reaction, methanol was distilled off under reduced pressure. The residue was made alkaline by addition of sat. aq. $NaHCO_3$ (100 ml) and extracted with EtOAc (3×150 ml). The organic layer was washed with water (150 ml) and brine (100 ml), dried over $Na_2SO_4$, filtered and concentrated under reduced pressure. The crude residue upon purification by flash chromatography (silica-gel; 18% EtOAc in PE) afforded the title product (3.2 g, 63%).

Step 7: 1-Benzyl-3-bromo-5-(4-methyl-4-((3-(trifluoromethyl)phenyl)sulfonyl)tetrahydro-2H-pyran-2-yl)-1H-pyrazole A solution of 1-benzyl-3-bromo-5-(4-((3-(trifluoromethyl)phenyl)sulfonyl)tetrahydro-2H-pyran-2-yl)-1H-pyrazole (10 g, 18.903 mmol, 1.0 eq) in THF (100 ml) was cooled to −78° C. and KOtBu (1M in THF, 26.9 ml, 26.9 mmol, 2.0 eq) was added dropwise. The mixture was stirred for 30 min, and then MeI (2.0 ml, 33.7 mmol, 2.5 eq) was added. The resulting RM was allowed to warm to RT and stirred for 18 h. The mixture was quenched with sat. aq. $NH_4Cl$ (200 ml) and water (200 ml), and extracted with EtOAc (3×200 ml). The combined organic layers were washed with water (2×200 ml) and brine (200 ml), dried ($Na_2SO_4$), filtered and concentrated under reduced pressure. The residue upon purification by flash chromatography (silica gel; 25-30% EtOAc in PE) afforded the title cis and trans racemates.

[cis-rac] 1-Benzyl-3-bromo-5-(4-methyl-4-((3-(trifluoromethyl)phenyl)sulfonyl)tetrahydro-2H-pyran-2-yl)-1H-pyrazole: 6 g (58%); TLC system: EtOAc-PE; 4:6; Rf: 0.24

[trans-rac] 1-Benzyl-3-bromo-5-(4-methyl-4-((3-(trifluoromethyl)phenyl)sulfonyl)tetrahydro-2H-pyran-2-yl)-1H-pyrazole: 1.32 g; TLC system: EtOAc-PE; 4:6; Rf: 0.32.

Step 8 can be carried out in analogy to step 8 of Example 4.

Step 9 can be carried out in analogy to step 9 of Example 4.

Step 10: The benzyl group can be removed by hydrogenation in the presence of 5% Palladium on carbon in TFA (80° C., 100 PSI) or in the presence of HBr in acetic acid (120° C.).

Step 11 & 12: Example 16 can be obtained over 2 steps in analogy to Example 15.

Step 13 & 14: Example 7 can be obtained over 2 steps in analogy to Example 6.

2. Assay Descriptions and Biological Data:

2.1 Fluorescence Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 μL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 μg/mL Geneticin (Invitrogen 10131-027) plus 50 μg/mL Hygromycin B (Invitrogen 10687-010) plus 2 μg/mL Blasticidin (anti-b15b Invivo-Gen) plus 0.2 μg/mL Puromycin (A 11138-03)] at a cell density of 30.000 cells per well. Plates were incubated at 37° C. (5% $CO_2$) for 20 to 23 h. On the day of experiment medium was discarded and cells were loaded with Fluo 4 by addition of 100 μL of basic assay buffer (10 mM HEPES, 1 mM KCl, 149 mM NaCl, 0.8 mM $CaCl_2$, 1.7 mM $MgCl_2$, 10 mM Glucose, 0.1% BSA. pH 7.4) containing 2 μM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 1004 basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 μL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 μL of basic assay buffer containing 210 mM KCl (NaCl omitted) were added for depolarization. Peak fluorescent signal intensity was determined and the amplitude of the peak signal, normalized to base line, was used to measure channel inhibition by test compounds.

The following tables summarize the inhibitory activity of exemplified compounds according to the present invention.

| Example | Isomer | Activity Category |
|---|---|---|
| 2 | cis-EN1 | B |
| 2 | cis-EN2 | A |
| 2 | trans-rac | C |
| 4 | cis-EN1 | C |
| 4 | cis-EN2 | C |
| 5 | cis-EN1 | B |
| 5 | cis-EN2 | A |
| 6 | cis-EN1 | B |
| 6 | cis-EN2 | A |
| 9 | cis-EN1 | B |
| 9 | cis-EN2 | B |
| 10 | cis-rac | A |
| 11 | cis-EN1 | B |
| 11 | cis-EN2 | B |
| 15 | cis-rac | A |
| 17 | cis-EN1 | B |
| 18 | cis-rac | A |
| 19 | cis-EN2 | A |
| 19 | cis-EN1 | B |
| 20 | cis-EN1 | B |
| 20 | cis-EN2 | B |
| 21 | cis-EN1 | A |
| 21 | cis-EN2 | A |
| 23 | cis-rac | B |
| 24 | cis-rac | A |
| 25 | cis-EN1 | B |
| 25 | cis-EN2 | A |
| 26 | cis-EN1 | A |
| 26 | cis-EN2 | B |
| 27 | cis-EN1 | B |
| 27 | cis-EN2 | B |
| 28 | cis-EN1 | B |
| 28 | cis-EN2 | B |
| 29 | cis-EN1 | B |
| 29 | cis-EN2 | B |

* %-Inhib (CaV2.2) @3 μM @30 mM KCl: "A": %-Inhibition >95%; "B": %-Inhibition >75% up to ≤95%; "C": %-Inhibition >40% up to ≤75%, "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at RT (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of –60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%. For each cell, current responses were normalised to dimethyl sulfoxide vehicle control to generate concentration-response curves. When multiple doses were achieved per cell, $IC_{50}$ values were calculated from the fits of the Hill equation to the data. The form of the Hill equation used was: Relative current=(100/(1+($IC_{50}$/conc)^Slope)). A selection of the foregoing exemplified compounds was tested under these conditions: Several compounds are potent inhibitors ($IC_{50}$<5 μM) or even very potent inhibitors ($IC_{50}$<2 μM).

The invention claimed is:
1. A compound of general formula (I):

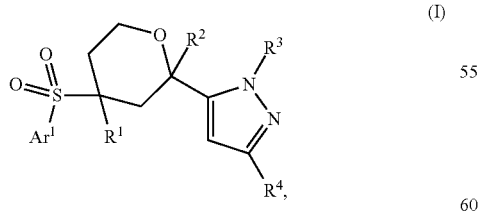

(I)

wherein
$R^1$ is selected from the group consisting of H and $C_{1-6}$-alkyl;
$R^2$ is selected from the group consisting of H and $C_{1-6}$-alkyl;
$R^3$ represents L'-$R^{3a}$, wherein L' is bond or $CH_2$ and
$R^{3a}$ is selected from the group consisting of substituted $C_{1-6}$-alkyl, $C_{3-6}$-cycloalkyl or 3 to 7 membered heterocyclyl,
wherein said substituted $C_{1-6}$-alkyl is substituted by one or two substituents independently selected from the group consisting of OH, $OCH_3$, $S(=O)_2CH_3$, $N(CH_3)_2$, $C(=O)NH_2$, $C(=O)NH(CH_3)$ and $C(=O)N(CH_3)_2$;
wherein said $C_{3-6}$-cycloalkyl and said 3 to 7 membered heterocyclyl is unsubstituted or substituted by one or two substituents independently selected from the group consisting of OH, $OCH_3$, =O, $S(=O)_2CH_3$, $NH_2$, $NH(CH_3)$, $N(CH_3)_2$, $C(=O)OH$, $C(=O)NH_2$, $C(=O)NH(CH_3)$ and $C(=O)N(CH_3)_2$;
and wherein said 3 to 7 membered heterocyclyl contains one or two heteroatoms or heteroatom groups independently selected from the group consisting of from 0, NH, $N(CH_3)$, $S(=O)$ and $S(=O)_2$;
$R^4$ represents L-$R^5$,
wherein L is bond, $CH_2$, $C(CH_3)_2$, O or $S(=O)_2$ and
$R^5$ is selected from the group consisting of $C_{1-6}$-alkyl, $C_{3-6}$-cycloalkyl and 3 to 7 membered heterocyclyl,
wherein said 3 to 7 membered heterocyclyl contains one heteroatom or heteroatom group, selected from O, NH, $N(CH_3)$, $S(=O)$ and $S(=O)_2$;
wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
and
wherein said $C_{3-6}$-cycloalkyl or said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
$Ar^1$ represents aryl or heteroaryl, wherein said aryl or said heteroaryl is substituted by zero or one or two or three substituents $R^7$,
wherein each $R^7$ is independently selected from the group consisting of F; Cl; Br; I; $NO_2$; CN; $C_{1-6}$-alkyl; $CF_3$; $CF_2H$; $CFH_2$; $CF_2Cl$; $CFCl_2$; C(O)—H; C(O)—$C_{1-6}$-alkyl; C(O)—OH; C(O)—O—$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—$S(O)_2$—$C_{1-6}$-alkyl; O—S(O)$_2$—OH; O—$S(O)_2$—O—$C_{1-6}$-alkyl; O—$S(O)_2$—$NH_2$; O—$S(O)_2$—N(H)($C_{1-6}$-alkyl); O—S(O)$_2$—N($C_{1-6}$-alkyl)$_2$; $NH_2$; N(H)($C_{1-6}$-alkyl); N($C_{1-6}$-alkyl)$_2$; N(H)—C(O)—$C_{1-6}$-alkyl; N(H)—C(O)—O—$C_{1-6}$-alkyl; N(H)—C(O)—$NH_2$; N(H)—C (O)—N(H)($C_{1-6}$-alkyl); N(H)—C(O)—N($C_{1-6}$-alkyl)$_2$; N($C_{1-6}$-alkyl)-C(O)—$C_{1-6}$-alkyl; N($C_{1-6}$-alkyl)-C(O)—O—$C_{1-6}$-alkyl; N($C_{1-6}$-alkyl)-C(O)—NH$_2$; N($C_{1-6}$-alkyl)-C(O)—N(H)($C_{1-6}$-alkyl); N($C_{1-6}$-alkyl)-C(O)—N($C_{1-6}$-alkyl)$_2$; N(H)—S(O)$_2$OH; N(H)—S(O)$_2$—$C_{1-6}$-alkyl; N(H)—S(O)$_2$—O—$C_{1-6}$-alkyl; N(H)—S(O)$_2$—NH$_2$; N(H)—S(O)$_2$—N(H)($C_{1-6}$-alkyl); N(H)—S(O)$_2$N($C_{1-6}$-alkyl)$_2$; N($C_{1-6}$-alkyl)-S(O)$_2$—OH; N($C_{1-6}$-alkyl)-S(O)$_2$—$C_{1-6}$-alkyl; N($C_{1-6}$-alkyl)-S(O)$_2$—O—$C_{1-6}$-alkyl; N($C_{1-6}$-alkyl)-S(O)$_2$—NH$_2$; N($C_{1-6}$-alkyl)-S(O)$_2$—N(H)($C_{1-6}$-alkyl); N($C_{1-6}$-alkyl)-S(O)$_2$—N($C_{1-6}$-alkyl)$_2$; SH; SCF$_3$; SCF$_2$H; SCFH$_2$; SCF$_2$Cl; SCFCl$_2$; S—$C_{1-6}$-alkyl; S(O)—$C_{1-6}$-alkyl; S(O)$_2$—$C_{1-6}$-alkyl; S(O)$_2$—OH; S(O)$_2$—O—$C_{1-6}$-alkyl; S(O)$_2$—NH$_2$; S(O)$_2$—N(H)($C_{1-6}$-alkyl); S(O)$_2$—N($C_{1-6}$-alkyl)$_2$; $C_{3-6}$-cycloalkyl; 3 to 7 membered heterocyclyl; aryl; heteroaryl; O—$C_{3-6}$-cycloalkyl; O-(3 to 7 membered heterocyclyl); O-aryl; O-heteroaryl; N(H)—$C_{3-6}$-cycloalkyl; N(H)-(3 to 7 membered heterocyclyl); N(H)-aryl; N(H)-heteroaryl; N($C_{1-6}$-alkyl)-$C_{3-6}$-cycloalkyl; N($C_{1-6}$-alkyl)-(3 to 7 membered heterocyclyl); N($C_{1-6}$-alkyl)-aryl; N($C_{1-6}$-alkyl)-heteroaryl; C(O)—$C_{3-6}$-cycloalkyl; C(O)-(3 to 7 membered heterocyclyl); C(O)-aryl; C(O)-heteroaryl; S(O)$_2$—$C_{3-6}$-cycloalkyl; S(O)$_2$-(3 to 7 membered heterocyclyl); S(O)$_2$-aryl; S(O)$_2$-heteroaryl; S(O)(NR$^{13}$)—$C_{3-6}$-cycloalkyl; S(O)(NR$^{13}$)-(3 to 7 membered heterocyclyl); S(O)(NR$^{13}$)-aryl and S(O)(NR$^{13}$)-heteroaryl, wherein R$^{13}$ represents H or $C_{1-6}$-alkyl;

with the proviso that the compound of general formula (I) is not 1-(2-Methoxyethyl)-5-(4-methyl-4-((3-(trifluoromethyl)phenyl)sulfonyl)tetrahydro-2H-pyran-2-yl)-3-(trifluoromethyl)-1H-pyrazole;

optionally in the form of a single stereoisomer or a mixture of stereoisomers, in the form of the free compound and/or a physiologically acceptable salt and/or a physiologically acceptable solvate thereof.

2. A compound according to claim 1, wherein the compound of general formula (I) is a compound according to general formula (II):

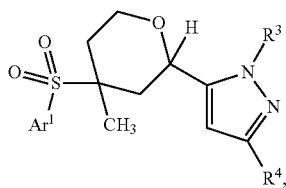

(II)

wherein Ar$^1$, R$^3$ and R$^4$ are defined as in claim 1.

3. A compound according to claim 1, wherein Ar$^1$ represents phenyl or pyridinyl, substituted by zero or one or two or three substituents R$^7$, wherein each R$^7$ is independently selected from the group consisting of F; Cl; CN; $C_{1-6}$-alkyl; CF$_3$; CF$_2$H; CFH$_2$; C(O)—$C_{1-6}$-alkyl; C(O) OH; C(O)—O—$C_{1-6}$-alkyl; C(O)—N(H)(OH); C(O)—NH$_2$; C(O)—N(H)($C_{1-6}$-alkyl); C(O)—N($C_{1-6}$-alkyl)$_2$; OH; OCF$_3$; OCF$_2$H; OCFH$_2$; OCF$_2$Cl; OCFCl$_2$; O—$C_{1-6}$-alkyl; NH$_2$; N(H)($C_{1-6}$-alkyl); N($C_{1-6}$-alkyl)$_2$; N(H)—C(=O)—$C_{1-6}$-alkyl; N($C_{1-6}$-alkyl)-C(O)—$C_{1-6}$-alkyl; N(H)—S(O)$_2$—$C_{1-6}$-alkyl; SCF$_3$; S—$C_{1-6}$-alkyl; S(O)—$C_{1-6}$-alkyl; S(O)$_2$—$C_{1-6}$-alkyl; S(O)$_2$—NH$_2$; S(O)$_2$—N(H)($C_{1-6}$-alkyl); S(O)$_2$—N($C_{1-6}$-alkyl)$_2$; $C_{3-6}$-cycloalkyl; 3 to 7 membered heterocyclyl; O—$C_{3-6}$-cycloalkyl and O-(3 to 7 membered heterocyclyl).

4. A compound according to claim 1, wherein Ar$^1$ is selected from the group consisting of 3-trifluoromethyl-phenyl; 3-difluoromethyl-phenyl; 3-fluoromethyl-phenyl; 3-trifluoromethoxy-phenyl; 3-difluoromethoxy-phenyl; 3-fluoromethoxy-phenyl; 3-fluoro-phenyl; 3-cyanophenyl; 6-trifluoromethyl-pyridin-2-yl; 3-difluoromethyl-pyridin-2-yl; 3-fluoromethyl-pyridin-2-yl; 3-trifluoromethoxy-pyridin-2-yl; 3-difluoromethoxy-pyridin-2-yl; 3-fluoromethoxy-pyridin-2-yl; 3-fluoro-pyridin-2-yl and 3-cyano-pyridin-2-yl.

5. A compound according to claim 1, wherein R$^3$ is selected from the group consisting of CH$_2$OH, CH$_2$CH$_2$OH, CH$_2$CH$_2$OCH$_3$, CH(CH$_3$)CH$_2$OH, CH(CH$_3$)CH$_2$OCH$_3$, C(CH$_3$)$_2$CH$_2$OH, C(CH$_3$)$_2$CH$_2$OCH$_3$, CH$_2$S(=O)$_2$CH$_3$, CH$_2$CH$_2$S(=O)$_2$CH$_3$, C(CH$_3$)$_2$CH$_2$S(=O)$_2$CH$_3$, CH$_2$CH$_2$N(CH$_3$)$_2$, C(CH$_3$)$_2$CH$_2$N(CH$_3$)$_2$, CH$_2$C(=O)N(CH$_3$)$_2$, CH$_2$C(=O)NH(CH$_3$), CH$_2$C(=O)NH$_2$, CH$_2$C(=O)OH, CH$_2$CH$_2$C(=O)N(CH$_3$)$_2$, CH$_2$CH$_2$C(=O)NH(CH$_3$), CH$_2$CH$_2$C(=O)NH$_2$, C(CH$_3$)$_2$CH$_2$C(=O)N(CH$_3$)$_2$, C(CH$_3$)$_2$CH$_2$C(=O)NH(CH$_3$), C(CH$_3$)$_2$CH$_2$C(=O)NH$_2$, CH$_2$C(CH$_3$)$_2$C(=O)NH$_2$, C(CH$_3$)$_2$C(=O)NH$_2$, CH$_2$C(CH$_3$)$_2$C(=O)NH(CH$_3$), CH$_2$C(CH$_3$)$_2$C(=O)NH$_2$, CH$_2$C(CH$_3$)$_2$C(=O)OH, CH$_2$CH$_2$CH$_2$OH, CH$_2$CH$_2$CH$_2$OCH$_3$, CH$_2$CH$_2$CH$_2$S(=O)$_2$CH$_3$, CH$_2$CH$_2$CH$_2$N(CH$_3$)$_2$, CH$_2$CH$_2$CH$_2$C(=O)N(CH$_3$)$_2$, CH$_2$CH$_2$CH$_2$C(=O)NH(CH$_3$), CH$_2$CH$_2$CH$_2$C(=O)NH$_2$, CH$_2$C(CH$_2$)$_2$NH$_2$ ((1-amino-cycloprop-1-yl)methyl), oxetanyl, CH$_2$C(H)(CH$_2$)$_2$O ((oxetan-3-yl)-methyl), CH$_2$C(OH)(CH$_2$)$_2$O ((3-hydroxy-oxetan-3-yl)-methyl) and 1,1-dioxo-thietanyl.

6. A compound according to claim 1, wherein R$^3$ is selected from the group consisting of CH$_2$OH, CH$_2$CH$_2$OH, CH$_2$CH$_2$OCH$_3$, CH(CH$_3$)CH$_2$OH, C(CH$_3$)$_2$CH$_2$OH, CH$_2$S(=O)$_2$CH$_3$, CH$_2$CH$_2$S(=O)$_2$CH$_3$, CH$_2$CH$_2$N(CH$_3$)$_2$, CH$_2$C(=O)OH, CH$_2$C(=O)NH$_2$, CH$_2$C(=O)N(CH$_3$)$_2$, CH$_2$C(=O)NH(CH$_3$), CH$_2$CH$_2$C(=O)NH$_2$, C(CH$_3$)$_2$C(=O)NH$_2$, CH$_2$C(CH$_3$)$_2$C(=O)NH$_2$, CH$_2$CH$_2$CH$_2$OH, CH$_2$CH$_2$CH$_2$OCH$_3$, CH$_2$C(CH$_2$)$_2$NH$_2$ ((1-amino-cycloprop-1-yl)methyl), 3-oxetanyl, CH$_2$C(OH)(CH$_2$)$_2$O ((3-hydroxy-oxetan-3-yl)-methyl) and 1,1-dioxo-thietan-3-yl.

7. A compound according to claim 1, wherein

L is bond; and

R$^5$ is selected from the group consisting of CH$_3$, CH(CH$_3$)$_2$, C(CH$_3$)$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$N(CH$_3$)$_2$, C(CH$_3$)$_2$C(=O)NH$_2$ C(CH$_3$)$_2$C(=O)NH(CH$_3$), C(CH$_3$)$_2$C(=O)N(CH$_3$)$_2$, cyclopropyl, cyclobuytyl and oxetanyl, wherein said cyclopropyl, cyclobuytyl or oxetanyl are unsubstituted or substituted with OH, OCH$_3$ or S(O)$_2$CH$_3$;

or

L is CH$_2$; and

R$^5$ is selected from the group consisting of CH$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH₂S(=O)₂(c-propyl), CH(CH₃)₂, C(CH₃)₃, CFH₂, CHF₂, CF₃, CH₂CF₃, CF₂CH₃, CH₂CFH₂, CH₂CHF₂, CH₂CH₂CF₃, CH₂CH₂OCH₃, CH₂CH₂OH, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N(CH₃)₂, CH₂CH₂C(=O)NH₂, CH₂CH₂C(=O)NH(CH₃), CH₂CH₂C(=O)N(CH₃)₂, C(CH₃)₂OCH₃, C(CH₃)₂OH, C(CH₃)₂S(=O)₂CH₃, C(CH₃)₂S(=O)₂CHF₂, C(CH₃)₂S(=O)₂CF₃, C(CH₃)₂S(=O)₂CFH₂, C(CH₃)₂S(=O)₂CH(CH₃)₂, C(CH₃)₂S(=O)₂(c-propyl), C(CH₃)₂N(CH₃)₂, C(CH₃)₂C(=O)NH₂ C(CH₃)₂C(=O)NH(CH₃), C(CH₃)₂C(=O)N(CH₃)₂, cyclopropyl, cyclobuytyl and oxetanyl, wherein said cyclopropyl, cyclobuytyl or oxetanyl are unsubstituted or substituted with CH₃, OH, NH₂, NH(CH₃), N(CH₃)₂, OCH₃ or S(O)₂CH₃;

or

L is C(CH₃)₂; and

R⁵ is selected from the group consisting of CH(CH₃)₂, C(CH₃)₃, CH₂OH, CH₂OCH₃, CH₂OCFH₂, CH₂OCHF₂, CH₂OCF₃, CH₂S(=O)₂CH₃, CH₂S(=O)₂CHF₂, CH₂S(=O)₂CF₃, CH₂S(=O)₂CFH₂, CH₂S(=O)₂CH(CH₃)₂, CH₂S(=O)₂(c-propyl), CFH₂, CHF₂, CF₃, CH₂CF₃, CF₂CH₃, CH₂CFH₂, CH₂CHF₂, CH₂CH₂CF₃, CH₂CH₂OCH₃, CH₂CH₂OH, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N(CH₃)₂, CH₂CH₂C(=O)NH₂, CH₂CH₂C(=O)NH(CH₃), CH₂CH₂C(=O)N(CH₃)₂, C(CH₃)₂OCH₃, C(CH₃)₂OH, C(CH₃)₂S(=O)₂CH₃, C(CH₃)₂S(=O)₂CHF₂, C(CH₃)₂S(=O)₂CF₃, C(CH₃)₂S(=O)₂CFH₂, C(CH₃)₂S(=O)₂CH(CH₃)₂, C(CH₃)₂S(=O)₂(c-propyl), C(CH₃)₂N(CH₃)₂, C(CH₃)₂C(=O)NH₂ C(CH₃)₂C(=O)NH(CH₃), C(CH₃)₂C(=O)N(CH₃)₂, cyclopropyl, cyclobuytyl and oxetanyl, wherein said cyclopropyl, cyclobuytyl or oxetanyl are unsubstituted or substituted with CH₃, OH, NH₂, NH(CH₃), N(CH₃)₂, OCH₃ or S(O)₂CH₃;

or

L is O; and

R⁵ is selected from the group consisting of CH₃, CH(CH₃)₂, C(CH₃)₃, CFH₂, CHF₂, CF₃, CH₂CF₃, CF₂CH₃, CH₂CFH₂, CH₂CHF₂, CH₂CH₂CF₃, C(CH₃)₂CH₂OCH₃, C(CH₃)₂CH₂OH, CH₂S(=O)₂CH₃, CH₂CH₂N(CH₃)₂, CH₂C(=O)NH₂, CH₂C(=O)NH(CH₃), CH₂C(=O)N(CH₃)₂, CH₂CH₂C(=O)NH₂ CH₂CH₂C(=O)NH(CH₃), CH₂CH₂C(=O)N(CH₃)₂, C(CH₃)₂OCH₃, C(CH₃)₂N (CH₃)₂, C(CH₃)₂C(=O)NH₂ C(CH₃)₂C(=O)NH (CH₃), C(CH₃)₂C(=O)N(CH₃)₂, cyclopropyl, cyclobuytyl and oxetanyl, wherein said cyclopropyl, cyclobuytyl or oxetanyl are unsubstituted or substituted with CH₃, OCH₃ or S(O)₂CH₃;

or

L is S(=O)₂; and

R⁵ is selected from the group consisting of CH₃, CH₂CH₃, CH(CH₃)₂, C(CH₃)₃, CFH₂, CHF₂, CF₃, CH₂CF₃, CF₂CH₃, CH₂CFH₂, CH₂CHF₂, CH₂CH₂CF₃, CH₂CH₂OCH₃, CH₂CH₂OH, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N(CH₃)₂, CH₂CH₂C(=O)NH₂ CH₂CH₂C(=O)NH(CH₃), CH₂CH₂C(=O)N(CH₃)₂, cyclopropyl, cyclobuytyl and oxetanyl, wherein said cyclopropyl, cyclobuytyl or oxetanyl are unsubstituted or substituted with CH₃, OCH₃ or S(O)₂CH₃.

8. A compound according to claim 1, wherein R⁴ is selected from the group consisting of CHF₂, CF₃, CF₂CH₃, CH₂CHF₂, CH₂CF₃, CH(CH₃)₂, C(CH₃)₃, OCF₃, OCHF₂, OCH₂CF₃, O-c-propyl (cyclopropyl-oxy), CH₂OCF₃, C(CH₃)₂OH, S(=O)₂CHF₂, S(=O)₂CF₃, S(=O)₂CH₂CH₂OCH₃, S(=O)₂CH₂CH₂OH, S(=O)₂CH₂CF₃, S(=O)₂CF₂CH₃, S(=O)₂CH₂CHF₂, S(=O)₂—CH(CH₂)₂O (S(=O)₂-oxetan-3-yl), CH₂S(=O)₂CHF₂, CH₂S(=O)₂CF₃, CH₂CH₂S(=O)₂CH₃, C(CH₃)₂S(=O)₂CH₃, cyclopropyl, C(CH₂)₂(CH₃) (1-methyl-cycloprop-1-yl), C(CH₂)₂S(=O)₂CH₃ (1-methylsulfonyl-cycloprop-1-yl), C(OH)(CH₂)₂O (3-hydroxy-oxetan-3-yl) and cyclobutyl.

9. A compound according to claim 7, wherein the compound of general formula (I) is selected from a compound according to general formula (IIIa), (IIIb), (IIIc), (IIId), (IIIe), (IIIf), (IIIg), (IIIh), (IIIj), (IIIk), (IIIm), (IIIn), (IIIn-1), (IIIn-2), (IIIo), (IIIp), (IIIq), (IIIr), (IIIs), (IIIt), (IIIu), (IIIv), (IIIw), (IIIx), (IIIy), (IIIy-1) and (IIIz):

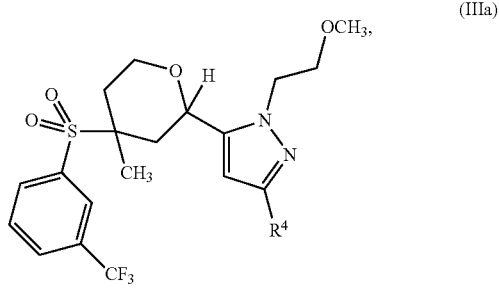

(IIIa)

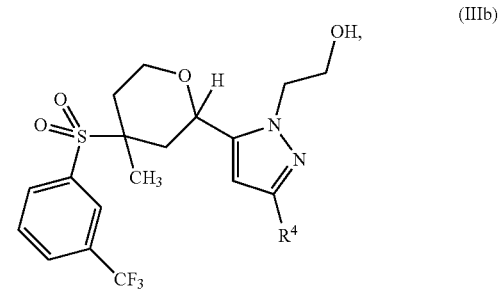

(IIIb)

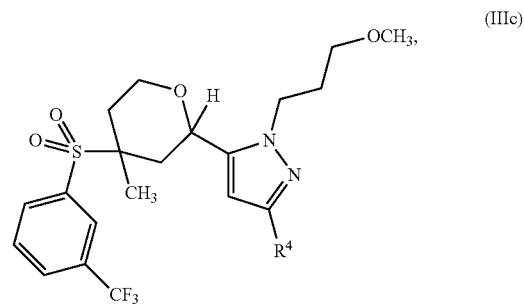

(IIIc)

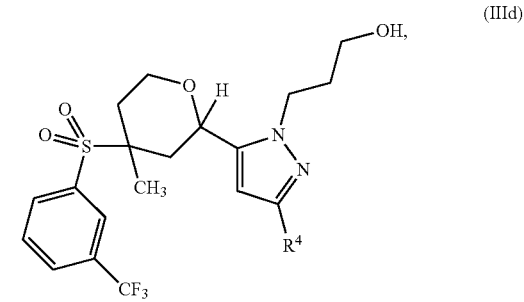

(IIId)

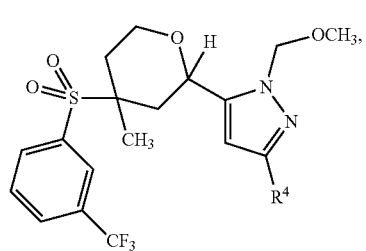 (IIIe)
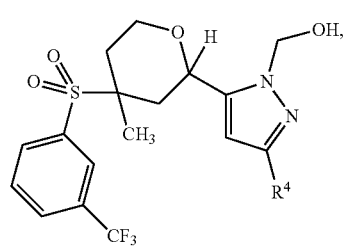 (IIIf)
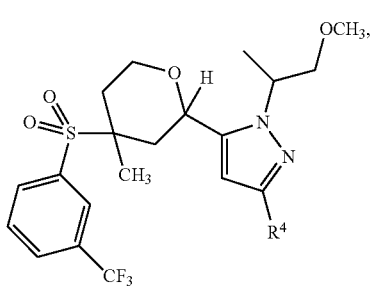 (IIIg)
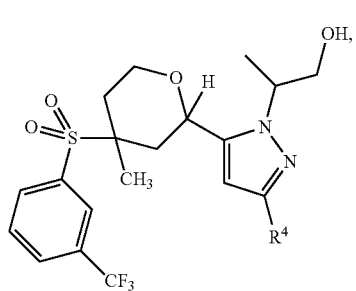 (IIIh)
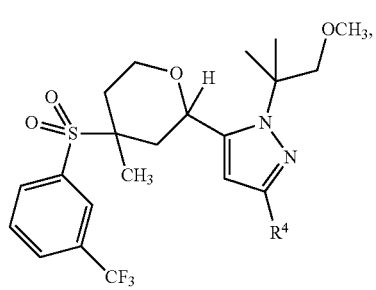 (IIIj)
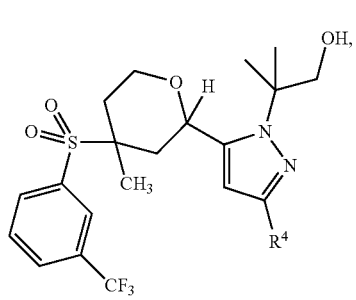 (IIIk)
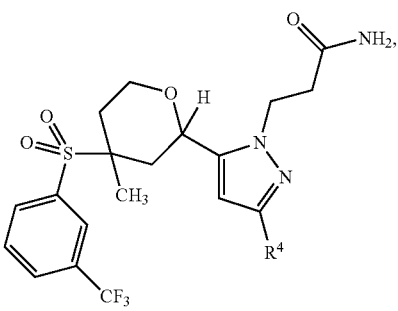 (IIIm)
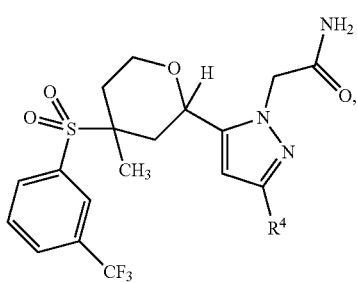 (IIIn)
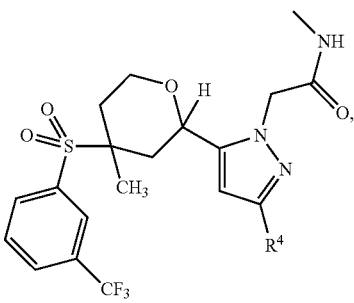 (IIIn-1)
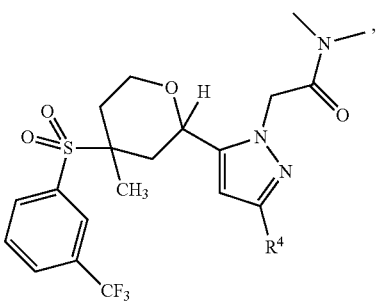 (IIIn-2)
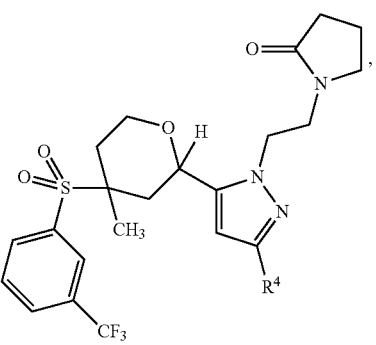 (IIIo)

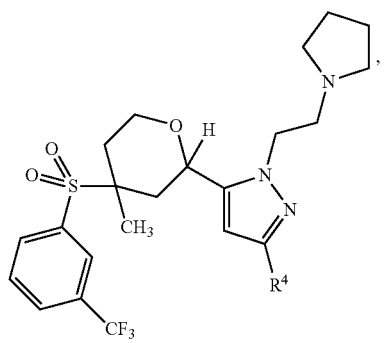
(IIIp)
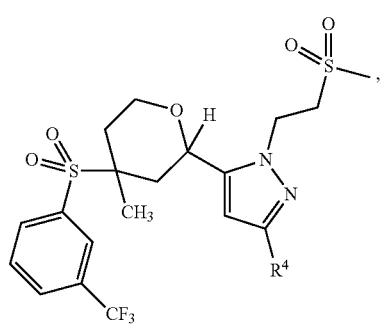
(IIIq)
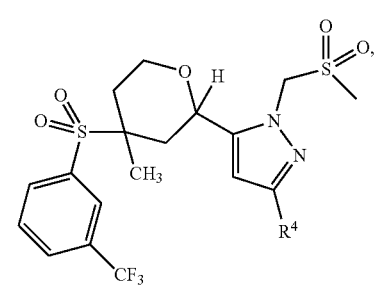
(IIIr)
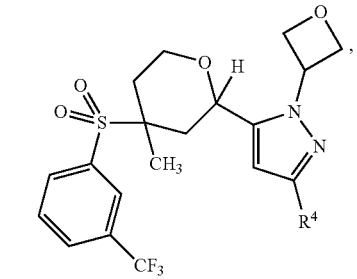
(IIIs)
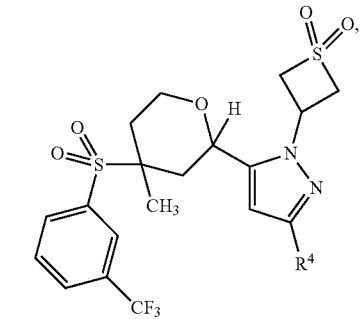
(IIIt)
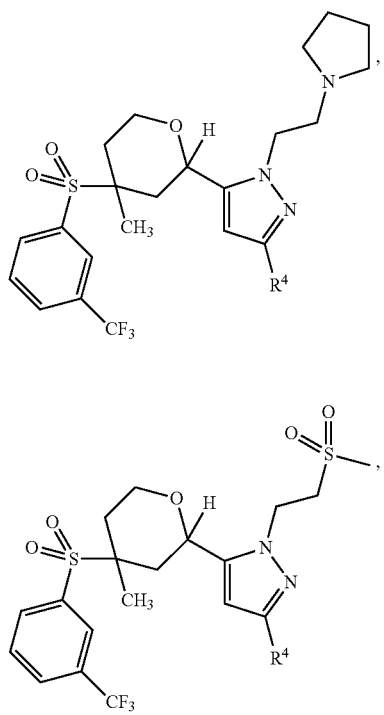
(IIIu)
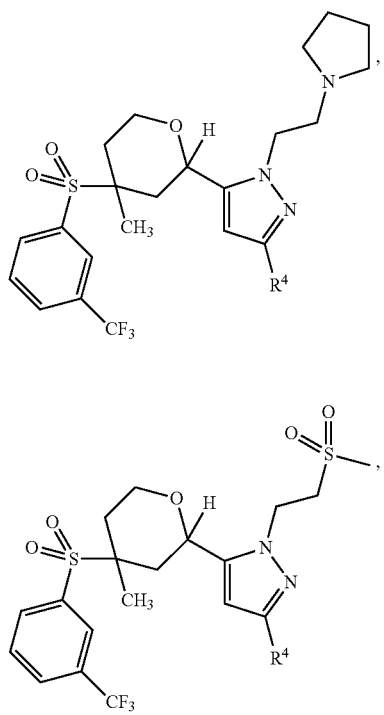
(IIIv)
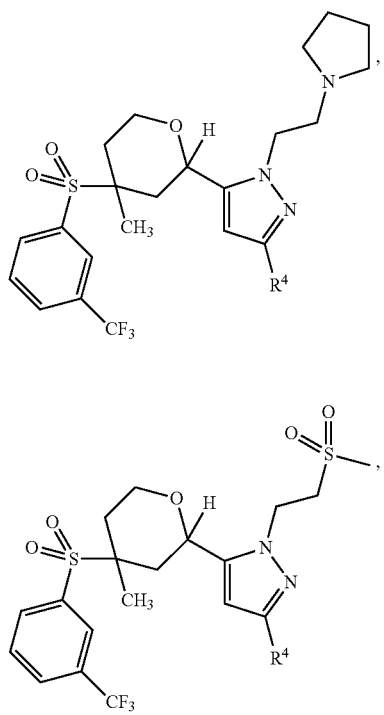
(IIIw)
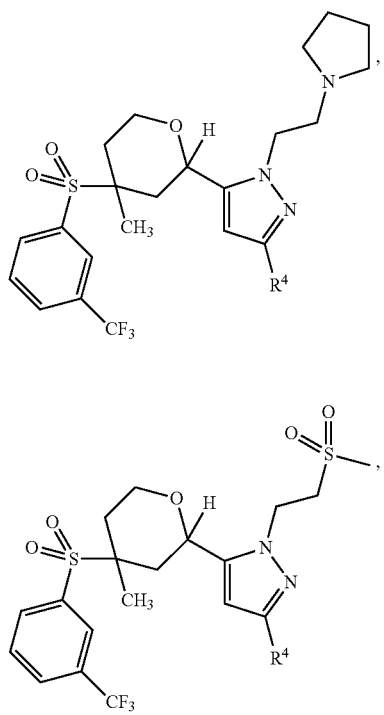
(IIIx)
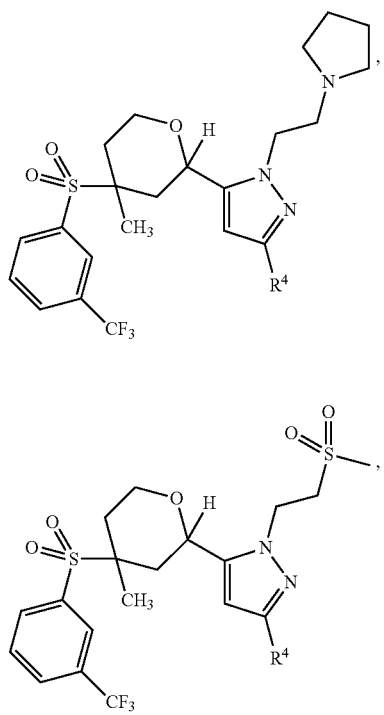
(IIIy)

-continued

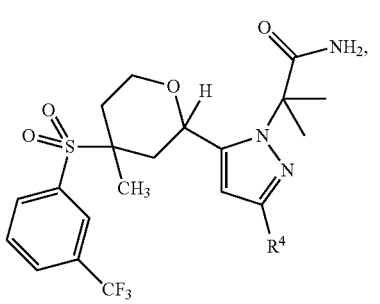

(IIIy-1)

(IIIz)

with the proviso that if the compound of general formula (I) is selected from a compound according to general formula (IIIa), then $R^4$ is not $CF_3$.

10. A compound according to claim 1, wherein the compound of general formula (I) is one diastereomer.

11. A compound according to claim 1, wherein the compound of general formula (I) is one enantiomer.

12. A compound according to claim 1, which is selected from the group consisting of:
1  [5-[4-Methyl-4-[[3-(trifluoromethyl)phenyl]sulfonyl]-tetrahydro-pyran-2-yl]-3-(trifluoromethyl)-1H-pyrazol-1-yl]-methanol;
2  2-[5-[4-Methyl-4-[[3-(trifluoromethyl)phenyl]sulfonyl]-tetrahydro-pyran-2-yl]-3-(trifluoromethyl)-1H-pyrazol-1-yl]-ethanol;
4  2-[3-Methylsulfonyl-5-[4-methyl-4-[[3-(trifluoromethyl)phenyl]sulfonyl]-tetrahydro-pyran-2-yl]-1H-pyrazol-1-yl]-ethanol;
5  3-(Difluoromethyl)-1-(methoxymethyl)-5-(4-methyl-4-((3-(trifluoromethyl)phenyl)sulfonyl)tetrahydro-2H-pyran-2-yl)-1H-pyrazole;
6  2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol;
7  2-Methyl-2-[3-methylsulfonyl-5-[4-methyl-4-[[3-(trifluoromethyl)phenyl]sulfonyl]-tetrahydro-pyran-2-yl]-1H-pyrazol-1-yl]-propan-1-ol;
8  3-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-oxetan-3-ol;
9  3-[5-[4-Methyl-4-[[3-(trifluoromethyl)phenyl]sulfonyl]-tetrahydro-pyran-2-yl]-3-(trifluoromethyl)-1H-pyrazol-1-yl]-propan-1-ol;
10  1-(3-Methoxypropyl)-5-(4-methyl-4-((3-(trifluoromethyl)phenyl)sulfonyl)tetrahydro-2H-pyran-2-yl)-3-(trifluoromethyl)-1H-pyrazole;
11  2-[5-[4-Methyl-4-[[3-(trifluoromethyl)phenyl]sulfonyl]-tetrahydro-pyran-2-yl]-3-(trifluoromethyl)-1H-pyrazol-1-yl]-acetamide;
12  3-[5-[4-Methyl-4-[[3-(trifluoromethyl)phenyl]sulfonyl]-tetrahydro-pyran-2-yl]-3-(trifluoromethyl)-1H-pyrazol-1-yl]-propionamide;
13  2,2-Dimethyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propionamide;
14  Dimethyl-[2-[5-[4-methyl-4-[[3-(trifluoromethyl)phenyl]sulfonyl]-tetrahydro-pyran-2-yl]-3-(trifluoromethyl)-1H-pyrazol-1-yl]-ethyl]-amine;
15  [1-[[5-[4-Methyl-4-[[3-(trifluoromethyl)phenyl]sulfonyl]-tetrahydro-pyran-2-yl]-3-(trifluoromethyl)-1H-pyrazol-1-yl]-methyl]-cyclopropyl]-amine;
16  [1-[[3-Methylsulfonyl-5-[4-methyl-4-[[3-(trifluoromethyl)phenyl]sulfonyl]-tetrahydro-pyran-2-yl]-1H-pyrazol-1-yl]-methyl]-cyclopropyl]-amine;
17  5-[4-Methyl-4-[[3-(trifluoromethyl)phenyl]sulfonyl]-tetrahydro-pyran-2-yl]-1-(oxetan-3-yl)-3-(trifluoromethyl)-1H-pyrazole;
18  1-(Methylsulfonyl-methyl)-5-[4-methyl-4-[[3-(trifluoromethyl)phenyl]sulfonyl]-tetrahydro-pyran-2-yl]-3-(trifluoromethyl)-1H-pyrazole;
19  1-(2-Methylsulfonyl-ethyl)-5-[4-methyl-4-[[3-(trifluoromethyl)phenyl]sulfonyl]-tetrahydro-pyran-2-yl]-3-(trifluoromethyl)-1H-pyrazole;
20  3-[5-[4-Methyl-4-[[3-(trifluoromethyl)phenyl]sulfonyl]-tetrahydro-pyran-2-yl]-3-(trifluoromethyl)-1H-pyrazol-1-yl]-thietane-1,1-dioxide;
21  1-(Methoxymethyl)-5-[4-methyl-4-[[3-(trifluoromethyl)phenyl]sulfonyl]-tetrahydro-pyran-2-yl]-3-(trifluoromethyl)-1H-pyrazole;
22  1-[2-[5-[4-Methyl-4-[[3-(trifluoromethyl)phenyl]sulfonyl]-tetrahydro-pyran-2-yl]-3-(trifluoromethyl)-1H-pyrazol-1-yl]-ethyl]-pyrrolidin-2-one;
23  1-(2-Methoxyethyl)-5-(4-methyl-4-((3-(trifluoromethyl)phenyl)sulfonyl)tetrahydro-2H-pyran-2-yl)-3-(methylsulfonyl)-1H-pyrazole;
24  2-Methyl-3-[5-[4-methyl-4-[[3-(trifluoromethyl)phenyl]sulfonyl]-tetrahydro-pyran-2-yl]-3-(trifluoromethyl)-1H-pyrazol-1-yl]-propan-1-ol;
25  2-[3-(Difluoro-methylsulfonyl)-5-[4-methyl-4-[[3-(trifluoromethyl)phenyl]sulfonyl]-tetrahydro-pyran-2-yl]-1H-pyrazol-1-yl]-ethanol;
26  2-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-propionamide;
28  N,N-Dimethyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide;
29  N-Methyl-2-[5-[4-methyl-4-[[3-(trifluoromethyl)phenyl]sulfonyl]-tetrahydro-pyran-2-yl]-3-(trifluoromethyl)-1H-pyrazol-1-yl]-acetamide;

optionally in the form of a single stereoisomer or a mixture of stereoisomers, in the form of the free compound and/or a physiologically acceptable salt or solvate thereof.

13. A pharmaceutical composition comprising at least one compound according to claim 1 and a pharmaceutically acceptable carrier.

14. A method for the treatment of one or more disorders selected from the group consisting of pain, stroke, mood disorders, epilepsy, schizophrenia, and neurodegenerative disorders, said method comprising administering to a patient in need thereof an effective amount therefor of at least one compound according to claim 1.

15. A method for the treatment of at least one form pain selected from the group consisting of acute pain, chronic pain, visceral pain, headache pain, inflammatory pain and mixed pain, said method comprising administering to a patient in need thereof an effective amount therefor of at least one compound according to claim 1.

* * * * *